US00RE42190E

(19) United States
(12) Reissued Patent
Chen et al.

(10) Patent Number: US RE42,190 E
(45) Date of Reissued Patent: Mar. 1, 2011

(54) METHOD OF IDENTIFYING A COMPOUND FOR INHIBITING OR STIMULATING HUMAN G PROTEIN-COUPLED RECEPTORS

(75) Inventors: Ruoping Chen, San Diego, CA (US); James N. Leonard, San Diego, CA (US)

(73) Assignee: Arena Pharmaceuticals, Inc., San Diego, CA (US)

(21) Appl. No.: 11/657,110

(22) Filed: Jan. 24, 2007

Related U.S. Patent Documents

Reissue of:
(64) Patent No.: 7,108,991
Issued: Sep. 19, 2006
Appl. No.: 10/393,807
Filed: Mar. 21, 2003

U.S. Applications:
(63) Continuation of application No. 10/272,983, filed on Oct. 17, 2002, which is a continuation of application No. 09/417,044, filed on Oct. 12, 1999, now abandoned.
(60) Provisional application No. 60/121,852, filed on Feb. 26, 1999, provisional application No. 60/109,213, filed on Nov. 20, 1998, provisional application No. 60/120,416, filed on Feb. 16, 1999, provisional application No. 60/123,946, filed on Mar. 12, 1999, provisional application No. 60/123,949, filed on Mar. 12, 1999, provisional application No. 60/136,436, filed on May 28, 1999, provisional application No. 60/136,439, filed on May 28, 1999, provisional application No. 60/136,567, filed on May 28, 1999, provisional application No. 60/137,127, filed on May 28, 1999, provisional application No. 60/137,131, filed on May 28, 1999, provisional application No. 60/141,448, filed on Jun. 29, 1999, provisional application No. 60/136,437, filed on May 28, 1999, provisional application No. 60/156,653, filed on Sep. 29, 1999, provisional application No. 60/156,633, filed on Sep. 29, 1999, provisional application No. 60/156,555, filed on Sep. 29, 1999, provisional application No. 60/156,634, filed on Sep. 29, 1999, provisional application No. 60/157,280, filed on Oct. 1, 1999, provisional application No. 60/157,294, filed on Oct. 1, 1999, provisional application No. 60/157,281, filed on Oct. 1, 1999, provisional application No. 60/157,293, filed on Oct. 1, 1999, and provisional application No. 60/157,282, filed on Oct. 1, 1999.

(51) Int. Cl.
*G01N 33/567* (2006.01)
*C12N 5/02* (2006.01)
*C12P 21/00* (2006.01)
*C07H 21/04* (2006.01)

(52) U.S. Cl. ..... 435/7.21; 435/325; 435/69.1; 435/320.1; 530/350; 536/23.5

(58) Field of Classification Search ..... None
See application file for complete search history.

(56) References Cited

U.S. PATENT DOCUMENTS

| | | | |
|---|---|---|---|
| 3,197,368 | A | 7/1965 | Lappe et al. |
| 5,462,856 | A | 10/1995 | Lerner et al. |
| 5,514,578 | A | 5/1996 | Hogness et al. |
| 5,532,157 | A | 7/1996 | Fink |
| 5,573,944 | A | 11/1996 | Kirschner et al. |
| 5,639,616 | A | 6/1997 | Liao et al. |
| 5,750,353 | A | 5/1998 | Kopin et al. |
| 5,891,646 | A | 4/1999 | Barak et al. |
| 5,932,445 | A | 8/1999 | Lal et al. |
| 5,942,405 | A | 8/1999 | Ames et al. |
| 6,051,386 | A | 4/2000 | Lerner et al. |
| 6,221,660 | B1 | 4/2001 | Bonini et al. |
| 6,468,756 | B1 | 10/2002 | Bonini et al. |
| 6,555,339 | B1 | 4/2003 | Liaw et al. |
| 6,555,344 | B1 | 4/2003 | Matsumoto et al. |
| 6,653,086 | B1 | 11/2003 | Behan et al. |
| 7,083,933 | B1 | 8/2006 | Griffin et al. |
| 7,108,991 | B2 | 9/2006 | Chen et al. |
| 2003/0064381 | A1 | 4/2003 | Feder et al. |
| 2003/0125539 | A1 | 7/2003 | Bonini et al. |
| 2003/0139590 | A1 | 7/2003 | Oshishi et al. |
| 2003/0148450 | A1 | 8/2003 | Chen et al. |
| 2003/0180813 | A1 | 9/2003 | Ohishi et al. |
| 2007/0122878 | A1 | 5/2007 | Chen et al. |
| 2008/0199889 | A1 | 8/2008 | Chen et al. |

FOREIGN PATENT DOCUMENTS

| | | |
|---|---|---|
| CA | 2135253 | 5/1996 |
| CA | 2362906 | 8/2000 |
| EP | 0 860 502 | 8/1998 |
| EP | 0860502 | 8/1998 |
| EP | 0 899 332 | 3/1999 |
| EP | 0899332 | 3/1999 |
| EP | 0 913 471 | 5/1999 |
| EP | 0913471 | 5/1999 |
| EP | 0 913 471 A2 | 5/1999 |
| EP | 1075493 | 2/2001 |
| EP | 1092727 A2 | 4/2001 |
| EP | 1 092 727 | 4/2001 |

(Continued)

OTHER PUBLICATIONS

Allenby et al., "Binding of 9–cis–retinoic acid and all–trans–retinoic acid to retinoic acid receptors alpha, beta, and gamma. Retinoic acid receptor gamma binds all–trans–retinoic acid preferentially over 9–cis–retinoic acid," Journal of Biological Chemistry, 269(24):16689–16695 (1994).
Berdyshev et al., "Effects of cannabinoid receptor ligands on LPS–induced pulmonary inflammation in mice," Life Sciences, 63:PL125–129 (1998).
Bhagwandin et al., "Structure and activity of human pancreasin, a novel tryptic serine peptidase expressed primarily by the pancreas," Journal of Biological Chemistry, 278(5):3363–3371 (2003).
Bjarnadottir et al., "Comprehensive repertoire and phylogenetic analysis of the G protein–coupled receptors in human and mouse," Genomics, 88(3):263–273 (2006).
Bowie et al., "Deciphering the message in protein sequences: tolerance to amino acid substitutions," Science, 247(4948): 1306–1310 (1990).

(Continued)

*Primary Examiner*—Robert Landsman
*Assistant Examiner*—Gyan Chandra
(74) *Attorney, Agent, or Firm*—Ropes & Gray LLP; Karen Mangasarian; Raymond M. Doss

(57) ABSTRACT

The invention disclosed in this patent document relates to transmembrane receptors, more particularly to endogenous, human orphan G protein-coupled receptors.

32 Claims, 5 Drawing Sheets

FOREIGN PATENT DOCUMENTS

| | | | |
|---|---|---|---|
| EP | 1 092 727 | A2 | 4/2001 |
| EP | 1338651 | | 8/2003 |
| WO | WO 98/00552 | | 1/1988 |
| WO | WO 93/25677 | | 12/1993 |
| WO | WO 97/11159 | | 3/1997 |
| WO | WO 97/20045 | | 6/1997 |
| WO | WO 97/21731 | | 6/1997 |
| WO | WO 97/24929 | | 7/1997 |
| WO | WO 98/31810 | | 7/1998 |
| WO | WO 98/34948 | | 8/1998 |
| WO | WO 98/38217 | | 9/1998 |
| WO | WO 98/39441 | | 9/1998 |
| WO | WO 98/46995 | | 10/1998 |
| WO | WO 98/50549 | | 11/1998 |
| WO | WO 99/24463 | | 5/1999 |
| WO | WO 99/24569 | | 5/1999 |
| WO | WO 99/25830 | | 5/1999 |
| WO | WO 99/42484 | | 8/1999 |
| WO | WO 99/46378 | | 9/1999 |
| WO | WO 99/52927 | | 10/1999 |
| WO | WO 99/52945 | | 10/1999 |
| WO | WO 99/52946 | | 10/1999 |
| WO | WO 99/55732 | | 11/1999 |
| WO | WO 99/55733 | | 11/1999 |
| WO | WO 99/55734 | | 11/1999 |
| WO | WO 99/64436 | | 12/1999 |
| WO | WO 00/11015 | | 3/2000 |
| WO | WO 00/11166 | | 3/2000 |
| WO | WO 00/11170 | | 3/2000 |
| WO | WO 00/22129 | | 4/2000 |
| WO | WO 00/22131 | | 4/2000 |
| WO | WO 00/23588 | | 4/2000 |
| WO | WO 00/26369 | | 5/2000 |
| WO | WO 00/28028 | | 5/2000 |
| WO | WO 00/31258 | * | 6/2000 |
| WO | WO 00/31258 | A2 | 6/2000 |
| WO | WO 00/42026 | | 7/2000 |
| WO | WO 00/50562 | | 8/2000 |
| WO | WO 00/12707 | | 9/2000 |
| WO | WO 01/32864 | A2 | 5/2001 |
| WO | WO 01/36473 | | 5/2001 |
| WO | WO 01/42288 | A2 | 6/2001 |
| WO | WO 01/87929 | A2 | 11/2001 |
| WO | WO 02/16548 | A2 | 2/2002 |
| WO | WO 02/44362 | A1 | 6/2002 |
| WO | WO 02/44362 | | 6/2002 |
| WO | WO 02/64789 | | 8/2002 |

OTHER PUBLICATIONS

Bowman et al.,(eds) In: Textbook of Pharmacology 2nd Edition, Blackwell Scientific Publications, Lonon, Chapter 29 (1980).

Byrnes et al., "Recent therapeutic advances in thrombotic thrombocytopenic purpura," Seminars in Thrombosis and Hemostasis, 5(3):199–215 (1979).

Cadas et al., "Occurrence and biosynthesis of endogenous cannabinoid precursor, N–arachidonoyl phosphatidylethanolamine, in rat brain," Journal of Neuroscience, 17(4):1226–1242 (1997).

Calignano et al., "Control of pain initiation by endogenous cannabinoids," Nature, 394(6690):277–281 (1998).

Chan et al., "Antisense oligonucleotides: from design to therapeutic application," Clinical and Experimental Pharmacology and Physiology, 33(5–6):533–540 (2006).

Di Marzo et al., "Interactions between synthetic vanilloids and the endogenous cannabinoid system," FEBS Letters 436(6):449–454 (1998).

Di Tomaso et al., "Brain cannabinoids in chocolate," Nature, 382(6593):677–678 (1996).

Elshourbagy et al., "Receptor for the pain modulatory neuropeptides FF and AF is an orphan G protein–coupled receptor," Journal of Biological Chemistry, 275(34), 25965–25971 (2000).

Fernandez et al., "Structure, function, and inhibition of chemokines," Annual Review of Pharmacology and Toxicology, 42:469–499 (2002).

Fujimoto et al., "Phasic effects of glucose, phospholipase $A_2$, and lysophospholipids on insulin secretion," Endocrinology, 120(5):1750–1757 (1987).

Fujimoto et al., "Phasic effects of glucose, p–hydroxymercuribenzoate, and lysophosphatidylcholine on insulin secretion from HIT cells," Diabetes, 38(5):625–628 (1989).

Gudas et al., "Cellular Biology and Biochemistry of the Retinoids," In: The retinoids: Biology, Chemistry and Medicine (Sporn MB; Roberts, AB, Goodman DS eds) 2nd edition, Raven Press, New York, pp. 443–520 (1994).

Hammonds et al., "Regulation and specificity of glucose–stimulated insulin gene expression in human islets of Langerhans," FEBS Letters, 223(1): 131–137 (1987).

Hilier et al., "Generation and analysis of 280,000 human expressed sequence tags," Genome Research, 6(9):807–828 (1996).

Hofmann et al., "Retinoids In Development," In: The retinoids: Biology, chemistry and medicine (Sporn, MB, Roberts, AB, Goodman DS eds) 2nd edition, Raven Press, New York, pp. 387–441 (1994).

Huang et al., "Discovery of human antibodies against the C5aR target using phage display technology," Journal of Molecular Recognition, 18(4):327–333 (2005).

Inagaki et al., "c–Jun represses the human insulin promoter activity that depends on multiple cAMP response elements," PNAS, 89(3):1045–1049 (1992).

Inagaki et al., "Regulation of Human Insulin Gene Expression by a cAMP," Molecular Genetics of Diabetes, 52(10):2528–2532 (1994).

Jaggar et al., "The anti–hyperalgesic actions of the cannabinoid anandamide and the putative CB2 receptor agonist palmitoylethanolamide in visceral and somatic inflammatory pain," Pain, 76(1–2)189–199 (1998).

Jaggar et al., "The endogenous cannabinoid anandamide, but not the CB2 ligand palmitoylethanolamide, prevents the viscero–visceral hyper–reflexia associated with inflammation of the rat urinary bladder," Neuroscience Letters, 253(2):123–126 (1998).

Lowe et al., "Cloning and characterization of human pancreatic lipase cDNA," Journal of Biological Chemistry, 264(33): 20042–20048 (1989).

Lowe et al., "Cloning and characterization of the human colipase cDNA," Biochemistry, 29(3):823–828 (1990).

Lutzlberger et al., "Strategies to identify potential therapeutic target sites in RNA," Handbook of Experimental Pharmacology, 173:243–259 (2006).

Mackril, "Generation, use, and validation of receptor–selective antibodies," Methods in Molecular Biology, 259:47–65 (2004).

Madiraju et al., "G protein–coupled receptors and insulin secretion: 119 and counting," Endocrinology, 148(6):2598–2600 (2007).

Maenhaut et al., "RDC8 codes for an adenosine A2 receptor with physiological constitutive activity," Biochemical and Biophysical Research Communications, 173(3):1169–1178 (1990).

Maldonato et al., "Glucose–induced proinsulin biosynthesis, Role of islet cyclic AMP," Diabetes, 26(6):538–545 (1977).

Manglesdorf et al., "The Retinoid Receptors," In: The retinoids: Biology, chemistry and medicine (Sporn, MD; Roberts, AB; Goodman DS eds) 2nd edition, Raven Press, New York, pp. 319–349 (1994).

Neilson et al., "Control of insulin gene expression in pancreatic beta–cells and in an insulin–producing cell line, RIN–5F cells, I. Effects of glucose and cyclic AMP on the transcription of insulin mRNA," Journal of Biological Chemistry, 260(25):13585–13589 (1985).

Nothacker et al., "From receptor to endogenous ligand," In: Receptors: Structure and Function, 2nd edition, CRC Press, Oxford, pp. 41–63 (2001).

Obermajerova et al., "Biochemical changes in mouse liver after palmitoyl–ethanolamide (PEA) administration," Chemico–biological Interactions, 6(4):219–226 (1973).

Overton et al., "Deorphanization of a G protein–coupled receptor for oleoylethanolamide and its use in the discovery of small–molecule hypophagic agents," Cell Metabolism, 3(3):167–175 (2006).

Overton et al., "GPR119, A novel G protein–coupled receptor target for the treatment of type 2 diabetes and obesity," British Journal of Pharmacology, 1–6 (2007).

Ozaki et a., "Isolation and characterization of a novel human pancreas–specific gene, pancpin, that is down–regulated in pancreatic cancer cells," Genes, Chromosomes and Cancer, 22:179–185 (1998).

Rachman et al., "Normalization of insulin responses to glucose by overnight infusion of glucagon–like peptide I (7–36) amide in patients with NIDDM," Diabetes 45(11):1524–1530 (1996).

Redfern et al., "Gene expression and neuroblastoma cell differentiation in response to retinoic acid: differential effects of 9–cis and all–trans retinoic acid," European Journal of Cancer, 31A(4):486–494 (1995).

Reseland et al., "A novel human chymotrypsin–like digestive enzyme," Journal of Biological Chemistry, 272(12):8099–8104 (1997).

Robertson, "G proteins and modulation of insulin secretion," Diabetes 40:1–6 (1991).

Rock et al., "Comparison of plasma exchange with plasma infusion in the treatment of thrombotic thrombocytopenic purpura," New England Journal of Medicine, 325(6):393–397 (1991).

Soga et al., "Lysophosphatidylcholine enhances glucose–dependent insulin secretion via an orphan G–protein–coupled receptor," Biochemical and Biophysical Research Communications, 326(4):744–751 (2005).

Stedman's Medical Dictionary, 28th Edition, p. 985 (2006).

Sugiura et al., "Enzymatic synthesis of oleamide (cis–9, 10–octadecenoamide), an endogenous sleep–inducing lipid, by rat brain microsomes," Biochemistry and Molecular Biology International, 40(5):931–938 (1996).

Takada et al., "Cloning of cDNAs encoding G protein–coupled receptor expressed in human endothelial cells exposed to fluid shear stress," Biochemical and Biophysical Research Communications, 240(3):737–741 (1997).

Textbook of Diabetes, 2nd Edition, vol. 1 (Pickup and Williams Eds.), Blackwell Science, Chapter 8, pp. 8.5–8.14 (1997).

Textbook of Diabetes, 2nd Edition, vol. 1 (Pickup and Williams Eds.), Blackwell Science, Chapter 9, pp. 9.1–9.15 (1997).

Thomas et al., "Oleamide–induced modulation of 5–hydroxytryptamine receptor–mediated signaling," Annals of the New York Academy of Sciences, 861:183–189 (1998).

Traynor et al., American Society for Pharmacology and Experimental Therapeutics, 47:848–854 (1995).

United States Patent and Trademark Office, Office Action, U.S. Appl. No. 11/894,692, Mar. 24, 2010.

Van Der Stelt et al., "Dioxygenation of N–linoleoyl amides by soybean lipoxygenase–1," FEBS Letters, 411(2–3):287–290 (1997).

Weinhaus et al., "Role of cAMP in upregulation of insulin secretion during the adaptation of islets of Langerhans to pregnancy," Diabetes, 47(9):1426–1435 (1998).

Wells, "Additivity of mutational effects in proteins," Biochemistry, 29(37):8509–8517 (1990).

Welsh et al., "Control of insulin gene expression in pancreatic beta–cells and in an insulin–producing cell line, RIN–5F cells. II. Regulation of insulin mRNA stability," Journal of Biological Chemistry, 260(25):13590–13594 (1985).

Whitcomb et al., "Human pancreatic digestive enzymes," Digestive Diseases and Sciences, 52(1):1–17 (2007).

Wu et al., "CCR5 levels and expression pattern correlate with infectability by macrophage–tropic HIV–1, in vitro," Journal of Experimental Medicine, 185(9):1681–1691 (1997).

Yajima et al., "cAMP enhances insulin secretion by an action on the ATP–sensitive $K^+$ channel–independent pathway of glucose signaling in rat pancreatic islets," Diabetes, 48:1006–1012 (1999).

Yamamoto et al., "Identification of the serum factor required for in vitro activation of macrophages. Role of vitamin D3–binding protein (group specific component, Gc) in lysophospholipid activation of mouse peritoneal macrophages," Journal of Immunology, 147(1):273–280 (1991).

Yang et al., "Lessons on autoimmune diabetes from animal models," Clinical Science, 110(6):627–639 (2006).

ATCC database search on insulinoma; downloaded Aug. 16, 2004.

ATCC database search on pancreas & beta cell; downloaded Aug. 16, 2004.

ATCC No. CRL –2055 on NIT–1 cell line; downloaded Aug. 17, 2004.

ATCC No. CRL –2057 on RIN–m cell line; downloaded Aug. 17, 2004.

ATCC No. CRL –2058 on RIN–5F cell line; downloaded Aug. 17, 2004.

ATCC No. CRL –2059 on RIN–14B cell line, downloaded Aug. 17, 2004.

U.S. Appl. No. 09/416,760, filed Oct. 12, 1999, Chen et al.

Alla, S.A et al., "Extracellular domains of the bradykinin B2 receptor involved in ligand binding and agonist sensing defined by anti–peptide antibodies," *J. Biol. Chem.,* 1996, 271, 1748–1755.

Advenier, C., et al., "Effects on the isolated human bronchus of SR 48968, a potent and selective nonpeptide antagonist of the neurokinin A ($NK_2$) receptors," Am. Rev. Respir. Dis., 1992, 146 (5 Pt. 1) 1177–1181.

Brier, "In situ hybridization with RNA probes," *Methods Mol Biol* (1999) 95:107–117.
Broun, P., et al., "Catalytic Plasticity of Fatty Acid Modification Enzymes Underlying Chemical Diversity of Plant Lipids," *Science,* 282:1315–1317, (Nov. 13, 1998).
Burstein, E.S. et al., "Constitutive activation of chimeric m2/m5 muscarinic receptors and delineation of G–protein coupling selectivity domains," *Biochem. Pharmacol.,* (1996), 51(4), 539–544.
Burstein, E.S. et al., "Amino acid side chains that define muscarinic receptor/G–protein coupling. Studies of the third intracellular loop," *J. Biol. Chem.,* (1996), 271(6), 2882–2885.
Burstein, E.s. et al., "Constitutive activation of muscannic receptors by the G–protein $G_9$" *FEBS Lett.,* (1995), 362(8), 261–263.
Burt, et al., "Agonist occupation of an alpha–2A–adrenoeceptor –Gi1–alpha fusion protein results in activation of both receptor linked and endogenous Gi proteins," *J. Biol. Chem.* (1997) 283:10367–10375.
Bylund, D., "International union of pharmacology nomenclature of adrenoceptors," *Pharmacol. Rev.,* (1994), 46, 121–136.
Casey, C. et al., "Constitutively active mutant 5–$HT_{2A}$ antagonists," Soc. Neurosci., 1996, Abstract #699.10.
Cheatham, B. et al., "Substitution of the erbB–2 oncoprotein transmembrane domain activates the insulin receptor and modulates the action of insulin–receptor substrate 1," *Proc. Natl. Acad. Sci. USA,* 1993, 90, 7336–7340.
Chen, J. et al., "Tethered Ligand Library for Discovery of Peptide Agonists," *J. Biol. Chem.,* 1995, 270, 23398–23401.
Chen, T.A. et al., "Microbial hydroxylation and glucuronidation of the angiotensin II (All) receptor antagonist MK 954," *J. Antibiot.* (*Tokyo*), 1993, 46(1) 131–134.
Chen, W. et al., "A colorimetric assay for measuring activation of $G_s$– and $G_q$– coupled signaling pathways," *Anal. Biochem.,* 1995, 226(2), 349–354.
Chidiac, P. et al., "Inverse agonist activity of β–adrenergic antagonists," *J. Pharm. Exp. Ther.* 1994, 45, 490–499.
Clozel, M. et al., "In vivo pharmacology of Ro 46–2005, the first synthetic nonpeptide endothelin receptor antagonist: implications for endothelin physiology," *J. Cardiovas. Pharmacol.,* 1993, 22(Suppl. 8), S377–S379.
Collesi, C. et al., "A splicing variant of the RON transcript induces constitutive tyrosine kinase activity and an invasive phenotype," *Mol. Cell. Biol.,* 1996, 16(2), 5518–5526.
Cooper, C.S. et al., "Molecular cloning of a new transforming gene from a chemically transformed human cell line," *Nature* 1984, 3–11, 29–33.
De Dois, I. et al., "Effect of L–364,718 (CCK Receptor Antagonist) on Exocrine Pancreatic Secretion of Hydrocortison–Treated Rate," *Pancreas,* 1994, 9(2), 212–218.
Desbios–Mouthon, C. et al., "Deletion of $Asn^{281}$ in the αsubunit of the human insulin receptor causes constitutive activation of the receptor and insulin desensitization," *J. Clin. Endocrinol. Metab.,* 1996, 81 (2), 719–727.
DiRenzo, M.F. et al., "Overexpression of the c–MET/HGF receptor gene in human thyroid carcinomas," *Oncogene,* 1992, 7, 2549–2553.
DiRenzo, M.F. et al., "Expression of the Met/HGF receptor in normal and neoplastic human tissues," *Oncogene,* 1991, 6(11), 1997–2003.
Doerks et al., "Protein annotation detective work for function prediction," *Trends Genet.* (1998), 14(6):248–50.
Drucker, Daniel, "Enhancing Incretin Action for the Treatment of type 2 Diabetes," *Diabetes Care,* vol. 26, No. 10, p. 2929–2940 2003.
Duprez, L. et al., "Germline mutations of the thyrotropin receptor gene cause non–antomimmune autosomal dominant hyperethyroidism," *Naature Genetics,* (1994), 7, 396–401.
Eggericksx, D. et al., "Molecular Cloning of an Orphan G–Protein–Coupled Receptor that Constitutively Activates Adenylate–Cyclase," *Biochem. J.,* (1995), 309, 837–843.
Evans, B.E. et al., "Orally Active, Nonpeptide Oxytocin Antagonists," *J. Med. Chem.,* (1992), 35, 3919–3927.
Fehmann et al., "Cell and molecular biology of the incretin hormones glucagon–like peptide–I and glucose–dependent insulin releasing polypeptide," *End. Rev.* (1995) 16:390–410.
Feighner, et al., "Receptor for Motilin Identified in the Human Gastrointestinal System," *Science,* American Association for the Advancement of Science, U.S. vol. 284, No. 5423, Jun. 25, 1999, 2184–2188.
Fischman et al., "Rapid detection of Parkinson's disease by SPECT with altropane; a selective ligand for dopamine transporters," *Synapse* (1998) 28(2):128–141.
Forman, et al., "Androstane metabolites bind to and deactivate the nuclear receptor CAR–beta," *Nature* (1998) 395:612–615.
Fu, M. et al., "Functional autoimmune epitope on $\alpha_1$ ~adrenergic receptors in patients with malignant hypertension," *Lancet,* (1994), 344, 1660–1663.
Furitsu, T. et al., "Identification of Mutations in the Coding Sequence of the Protooncogene c–kit in a Human Mast Cell leukemia Cell Line Causing Ligand–independent Activation of c–kit in a Human Mast Cell Leukemia Cell Line Causing Ligand–independent Activation of c–kit Product," *J. Clin. Invest.,* 1993, 92, 1736–1744.
Alexander, W.S. et al., "Point mutations within the dimmer interface homology domain of c–Mpl induce constitutive receptor activity and tumorigenicity," *EMBO J.,* 1995, 14(22), 5569–5578.
Arvanitikis, L. et al., "Human herpesvirus KSHV encloses a constitutively active G–protein–coupled receptor linked to cell proliferation," *Nature,* 1997, 385, 347–349.
Barker, E.L., et al., "Constitutively active 5–$hydroxytryptamine_{2c}$ receptors reveal novel inverse agonist activity of receptor ligands," *J. Biol. Chem.,* 1994, 269(16). 11687–11690.
Baxter G., "5–$HT_2$ receptors a family re–united?" *Trends Pharmacol. Sci.,* 1995, 16, 105–110.
Bentley, "Genomic sequence information should be release immediately and freely to the public," The Sanger Institute Human Genome Project, Policy Forum, *Science* (1996) 274:533–534.
Besmer, P. et al., "A new acute transforming feline retrovirus and relationship of its oncogene v–kit with the protein kinase gene family," *Nature* (1986) 320, 415–421.
Bergsma, er al., "Cloning nad characterization of a human angiotensin II type 1 receptor," *Biochem. Biophs. Res. Comm.* (1992) 183:989–995.
Berridge, "Inositol triphosphate and calcium signaling," *Nature* (1993) 361:315–325.
Bertin, et al., "Cellular signaling by an agonist activated receptor/Ge–alpha protein," *Proc. Natl. Acad. Sci. USA.* (1994) 91 8827–8831.

Besmer, P. et al., "A new acute transforming feline retrovirus and relationship of its oncognene *v–kit* with the protein kinase gene family," *Nature* (1986) 320, 415–421.

Bhathena, et al., "Insulin, glucagon and somatostatin secretion by cultured rat islet cell tumor and its clones," *Proc. Soc. Exptal. Biol. Med.* (1984) 175:35–38.

Blaszczyk, "Motor deficiency in Parkinson's disease," *Acta Neurobiol Exp* (1998) 58:79–93.

Blin, N. et al., "Mapping of single amino acid residues required for selective activation of $G_{9/11}$ by the m3 muscarinic acetylcholine receptor," *J. Biol. Chem.,* 1995, 270, 17741–17748.

Bond, R.A. et al., "Inverse agonists and G–protein–coupled receptors," in Receptor–Based Drug Design, Leff, P. (ed.), New York, M. Dekker, 1998, 363–377.

Boone, C. et al., "Mutations that alter the third cytoplasmic loop of the a–factor receptor lead to a constitutive and hypersensitive phenotype," *Proc. Natl. Acad. Sci. U.S.A.* 1993, 90(21), 9921–9925.

Gantz, I. et al., "Molecular Cloning of a Novel Melanocortin Receptor," *J. Biol. Chem.,* 1993, 268(11), 8246–8250.

Gantz, et al., "Molecular cloning expression and gene localization of a fourth melanocortin receptor," *J. Biol. Chem.,* (1993) 268:15174–15178.

Gellai, M. et al., "Nonpeptide Endothelin Receptor Antagonists V: Prevention and Reversal of Acute Renal Failure in the Rat by SB–209670," *J. Pharm. Exp. Therap.,* 1995, 275(1), 200–206.

Gether and Kobilka, "G Protein–coupled Receptors," *Journal of Biological Chemistry* (1998), vol. 273 No. 29.

Gitter, B. et al., "Pharmacological Characterization of LY303870; A Novel Potent and Selective Nonpeptide Substance P (Neurokinin–1) Receptor Antagonist," *J. Pharm. Exp. Therp.,* 1995, 275(2), 737–744.

Gouilleux–Gruart, V. et al., "STAT–Related Transcription Factors are Constitutively Activated in Peripheral Blood Cells from Acute Leukemia Patients," *Blood,* 1996, 87(5), 1692–1697.

Gracheck et al., *Annual Rep. Med. Chem.* (1993) 28:161–166.

Groblewski, et al., "Mutation of asn111 in the third transmembrane domain of the At1a angiotensin II receptor induces its constitutive activation," *J. Biol. Chem.* (1997) 272:1822–1826.

Hansson, J.H. et al., "Hypertension caused by a truncated epithelia sodium channel γ subunit: genetic heterogeneity of Liddle syndrome," *Nat. Genet.,* 1995, 11(1), 76–82.

Hasegawa, H. et al., Two Isoforms of the Prostaglandin E. Receptor EP3 Subtype Different in Agonist–independent Constitutive Activity, *J. Biol. Chem.,* 1996, 271(4), 1857–1860.

Hegyi et al., "The relationship between protein structure and function: a comprehensive survey with application to the yeast genome," *J. Mol. Biol.* (1999) 288:147–164.

Heiber, M. et al., "Isolation of Three Novel Human Genes Encoding G Protein–Coupled Receptors," *DNA and Cell Biology,* 1995, 14(1), 25–35.

Hendler, Fl. et al., Human Squamous Cell Lung Cancers Express Increased Epidermal Growth Factor Receptors, *J. Clin. Invest.,* 1984, 74, 647–651.

Herrick–Davis, K. et al., "Constitutively Active 5HT2C Serotonin Receptor Created by Site–Directed Mutagenesis," *Soc. Neurosci,* (1996) Abstract No. 699.18.

Hieble, J., "International union of pharmacology X. Recommendation for nomenclature of 1–adrenoceptors," *Pharm Rev,* 1995, 47, 267–270.

Hill, S., "Distribution Properties, and Functional Characteristics of Three Classes of Histamine Receptor," *Am. Soc. Pharm. Exp. Therap.,* 1990, 42(1), 45–83.

Hillier L., et al., "Generation and analysis of 280000 human expressed sequence tags", *EMBL Database Accession Number H67224,* 1995, abstract.

Hirsh, et al., "Neuronal vulnerability in Parkinson's disease," *J. Neural Transm. Suppl.* (1997) 50:79–88.

Hogger, P. et al., "Activating and Inactiving Mutations in — and C–terminal i3 Loop Junctions of Muscarinic Acetylcholine Hm1 Receptors," *J. Biol. Chem.,* 1995, 270(13), 7405–7410.

Howard, A.D. et al., "A Receptor in Pituitary and Hypothalamus That Functions in Growth Hormone Release," *Science,* 1996, 273, 974–977.

Hulley, et al., "Inhibitors of type IV phosphodiesterases reduce the toxicity of MPTP in Substantia nigra neurons in vivo," *Eur. J. Neurosci* (1995) 7:2431–2440.

Iismaa, T.P. et al., "Isolation and Chromosomal Localization of a Novel Human G–Protein–Coupled Receptor (GPR3) Expressed Predominantly in the Central Nervous System," *Genomics,* 1994, 24, 391–394.

Ikeda, H. et al., "Expression and Functional Role of the Proto–oncogene c–kit in Acute Myeloblastic Leukemia Cells," *Blood,* 1991, 78(11), 2962–2968.

Imura, R. et al., "Inhibition by HS–142–1, a novel nonpeptide atrial natriuretic peptide antagonist of microbial origin, of atrial natriuretic peptide–induced relaxation of isolated rabbit aorta through the blockade of guanylyl cyclase–linked receptors," *Mol. Pharm.,* (1992), 42, 982–990.

Itoh, H. et al., "Molecular cloning and sequence determination of cDNAs for a subunits of the guanine nucleotide–proteins $G_s$, $G_i$, and $G_o$ from rat brain," *Proc. Natl. Acad. Sci. USA,* (1986), 83, 3776–3780.

Jakubik, J. et al., "Constitutive activity of the $M_1$–$M_4$ subtypes of muscarinic receptors in transfected CHO cells and of muscarinic receptors in the heart cells revealed by negative antagonists," FEBS Letts., 1995, 377, 275–279.

Jayawickreme et al. "Gene expression systems in the development of high–throughput screens," *Current Opinion in Biotechnology* (1997) 629–634.

Jensen et al., "mRNA Profiling of Rat Islet Tumors Reveals Nkx 6.1 as a βCell–specific Homeodomain Transcription Factor," *J. Biol. Chem.,* 1996, 271(31), 18749–18758.

Ji et al., "G–Protein–Coupled Receptors," *J. Biol. Chem.* (1998) 273:17299–17302.

Johnson and Bressler, "New Pharmacologic Approaches", Chap. 59 in Ellenberg and Rifkin's Diabetes Milletus, 5$^{th}$ ed., Appleton and Lange, publishers, 1990, pp. 1293–1294.

Karpe et al., "The nicotinic acid receptor—a new mechanism for an old drug," *The Lancet* (2004) 363:1892–1894.

Karen–Kulju McKee, et al., "Cloning and Characterization of Two Human G Protein–Coupled Receptor Genes (GPR38 and GPR39) Related to the Growth Hormone Secretagogue and Neurotensin Receptors," *Genomics,* Academic Press, San Diego, Us, vol. 46, No. 3, 1997, pp. 423–434.

Kasuya, et al., Three–dimensional structure analysis of PROSITE patterns, *J. Mol. Biol.* (1999) 286: 1673–1691.

Kenakin, T., "Are Receptors Promiscuous? Intrinsic Efficacy as a Transduction Phenomenon," *Life Sciences,* (1988), 43, 1095–1101.

Kieffer, Timothy, "GIP or not GIP? That is the question," *TRENDS in Pharmacological Sciences* (2003) vol. 24, No. 3, 110–112.

Kjelsberg, MA., et al., "Constitutive activation of the $\alpha_{1B}$–adrenergic receptor by all amino acid substitutions at a single site," *J. Biol. Chem.,* (1992), 267(3), 1430–1433.

Knapp, R., et al., "Molecular biology and pharmacology of cloned opioid receptors," *FASEB J.* (1996), 9, 516–525.

Koike et al., "Human type 2 angiotensin II receptor gene cloned, mapped to the X chromosome, and its mRNA is expressed in the human lung," *Biochem. Biophys. Res. Comm.* (1994) 203:1842–1850.

Konig et al., "Method for Identifying Ligands That Bind to Cloned $G_5$– or $G_1$– Coupled Receptors," *Mol. Cell. Neuro.,* (1991) 2, 331–337.

Kosugi, S. et al., "Characterization of heterogeneous mutations causing constitutive activation of the luteinizing hormone receptor in familial male precocious puberty," *Human Mol. Genetics,* 1995, 4(2), 183–186.

Kosugi, S. et al., "Identification of Thyroid–Stimulating Antibody–Specific Interaction Sites in the N–Terminal Region of the Thyrotropin Receptor," *Mol. Endocrinology,* 1993, 7, 114–130.

Kraus, M. et al., "Demonstration of ligand–dependent signaling by the erbB–3 tyrosine kinase and its constitutive activation in human breast tumor cells," *Proc. Natl. Acad. Sci. USA,* 1993, 90, 2900–2904.

Kudlacz, E. et al., "In Vitro and In Viro Characterizatoin of MDL 105,212A, a Nonpeptide NK–1/NK–2 Tachykinin Receptor Antagonist," *J. Pharm. Exp. Therap.,* 1996, 277(2), 840–851.

Kuriu, A., et al., "Proliferation of Human Myeloid Leukemia Cell Line Associated with the Tyrosine–Phosphorylation and Activation of the Proto–oncogene c–kit Product," *Blood,* 1991, 78(11), 2834–2840.

Kyaw, et al., "Cloning characterization and mapping of human hmolog of mouse T–cell death–associated gene," *DNA Cell Biol.* (1998) 17:493–500.

Labbé–Jullié, C. et al., "Effect of the nonpeptide neurotensin antagonist, SR 48692, and two enantiomeric analogs, SR 48527 and Sr 49711, on neurotension binding and contractile responses in guinea pig ileum and colon," *J. Pharm. Exp. Therap.,* (1994), 271(1), 267–276.

Lambert "Signal transduction; G proteins and second messengers," *Br J Anaesth* (1993) 71:86–95.

Latronico, A. et al., "A novel mutation of the luteinizing hormone receptor gene causing male gonadotropin–independent precocious puberty," *J Clin. Endocrinol. Metabl.,* (1995), 80(8), 2490–2494.

Laue, L. et al., "Genetic heterogeneity of constitutively activating mutations of the human luteinizing hormone receptor in familial male–limited precocious puberty," *Proc. Natl. Acad. Sci USA* 1995, 92, 1905–1910.

Lazareno "Measurement of agonist–stimulated [35S]GTP gamma S binding to cell membranes," *methods Mol Bio* (1999) 106:231–245.

Leenders et al., "The nigrostriatal dopaminergic system assessed in vivo by positron emission tomography in healthy volunteer subjects and patients with Parkinson's disease," *Arch Neurol* (1990) 47(12):1290–1298.

Lefkowitz, R., et al., "Constitutive activity of receptors coupled to guanine nuceleotide regulatory proteins," *Trends Pharmacol. Sci.,* (1993), 14, 303–307.

Leonard, J. et al., "The LIM family transcription factor Isl–1 requires camp response element binding protein to promote somatostatin expression in pancreatic islet cells," *Proc. Natl. Acad. Sci. USA,* 1992, 89, 6247–6251.

Leurs, R., et al., "Agonist–independent regulation of constitutively active G–protein–coupled receptors," *TIBS,* 23 418–422, (Nov. 1998).

Libermann, T. et al., "Amplification, enhanced expression and possible rearrangement of EGF receptor gene in primary human brain turnours of glial origin," *Nature,* (1985), 313, 144–147.

Liu, C. et al., "Overexpression of c–met proto–oncogene but not epidermal growth factor receptor or c–erbB–2 in primary human colorectal carcinomas," *Oncogene,* (1992), 7, 181–185.

Liu, J. et al., "Molecular mechanisms involved in muscarinic acetylcholine receptor–mediated G protein activation studied by insertion mutagenesis," *J. Biol. Chem.,* (1996) 271(11), 6172–6178.

Lonardo, F. et al., "The normal erbB–2 product is an atypical receptor–like tyrosine kinase with constitutive activity in the absence of a ligand," *New Biologist,* 1990, 2(11), 992–1003.

Lovlie, R. et al., "The $Ca^{2+}$–sensing receptor gene (PCAR1) mutation T151M in isolated autosomal dominant hypoparathyroidism," *Hum. Gent,* (1996), 98, 129–133.

Lu et al., "The role of the free cytosolic calcium level in β–cell signal transduction by gastric inhibitory polypeptide and glucagons–like peptide I(7–37*)," *Endocrinology* (1993) 132(1):94–100.

Major et al. "Challenges of high throughput screening against cell surface receptors," *J. of Receptor and Signal Transduction Res.* (1995) 15:596–607.

Mann, J. et al., "Increased serotonin$_2$ and β–adrenergic receptor binding in the frontal cortices of suicide victims," *Arch. Gen. Psychiatry,* (1986), 43, 954–959.

Marchese, A. et al., "Cloning of Human Genes Encoding Novel G Protein–Coupled Receptors," *Genomics,* 1994, 23, 609–618.

Marks, D.L. et al., "Simultaneous Visualization of Two Cellular Mrna Species in Individual Neurons by Use of a New Double in Situ Hybridization Method," *Mol. & Cell. Neuro.,* (1992), 3, 395–405.

Martone, R.L. et al., "Human CRF receptor chimeras, Mapping of ligand binding determinants," 26$^{th}$ Meeting of the Society of Neuroscience, Washington, D.C. Nov. 16–21, (1996), Abstract No. 609.8.

Magnusson, Y. et al., "Autoimmunity in idiopathic dilated cardiomyopathy," *Circulation,* (1994), 89, 2760–2767.

Matsumoto, et al., "An evolutionarily conserved G–protein coupled receptor family, SREB, expressed in the central nervous system," *Biochem. Biophys. Res. Comm.* (2000) 272:576–582.

Matsuoka, I., et al., "Identification of Novel members of G–protein coupled receptor subfamily", *Biochemical and Biophysical Research Communications* 1993, 194. (whole document).

Matus–Leibovitch, N. et al., "Truncation of the thyrotropin–releasing hormone receptor carboxyl tail causes constitutive activity and leads to impaired responsiveness in Xenopus Oocytes and AtT20 Cells," *J. Biol. Chem.,* 1995, 270(3), 1041–1047.

Montastruc et al., "New directions in the drug treatment of Parkinson's disease," *Drugs & Aging* (1996) 9(3):169–184.

Munzy D., et al., "Homo sapiens chromosome 2p 13.3, clone RPCI1111–433J6—sequencing in progress—100 unordered pieces." *EMBL Database Accession Number AC006087,* 1998.

Murdoch et al., "Chemokine receptors and their role in inflammation and infectious diseases," *Blood* (2000) 95:3032–3043.

Myles, G.M. et al., "Tyrosine 569 in the c–Fms juxtamembrane domain is essential for kinase acitivity and macrophage colony–stimulating factor–dependent internalization," *Mol. Cell. Biol.* (1994), 14(7) 4843–4854.

Nanevicz, T. et al., "Thrombin receptor activating mutations," *J. Biol. Chem.,* (1996) 271(2), 702–706.

Natali, P.G. et al., "Expression of the c–Met/HGF receptor in human melanocytic neoplasms demonstration of the relationship to malignant melanoma tumour progression," *Br. J. Cancer,* (1993), 68, 746–749.

Neilson, K.M. et al., "Constitutive activation of fibroblast growth factor receptor–2 by a point mutation associated with Crouzon syndrome," *J. Biol. Chem.,* (1995), 270(44), 26037–26040.

Ng, D.H.W. et al., "Point Mutation in the Second Phosphatase Domain of CD45 Abrogates Tyrosine Phosphatase Activity," *Biochemical and Biophysical Research Communications,* 206(1):302–309, (Jan. 5,(1995).

Nicholas, J.G. et al., (eds.), "Indirect Mechanisms of Synaptic Transmission," in *From Neuron To Brain,* 3rd Edition, Sinauer Associates, Inc., (1992).

Noda, et al. "The active state of the AT1 angiotensin receptor is generated by angiotensin II induction," *Biochemistry* (1996) 35: 16435–16442.

Oda, S. et al., "Pharmacological profile of HS–142–1, a novel noneptide atrial natriuretic peptide (ANP) antagonist of microbial origin. II. Restoration by HS–142–1 of ANP–induced inhibition of aldosterone production in adrenal glomerulosa cells," *J. Pharm. Exp. Ther.,* 1992, 263(1), 241–245.

O'Dowd, B. et al., "Cloning and chromosomal mapping of four putative novel human G–protein–coupled receptor genes," *Gene,* 1997, 187. 75–81.

O'Dowd, B.F. et al., "Site–directed mutagenesis of the cytoplasmic domains of the human β2–adrenergic receptor," *J. Biol. Chem.,* 1988, 263(31), 15985–15992.

O'Dowd B.F., et al., "Discovery of Three Novel G–Protein–Coupled Receptor Genes", *Genomics* 1998, 47, pp. 310–313 (whole document).

Oerks, et al., "Protein annotation detective work for function prediction," Trends Genet: (1998) 14:248–250.

Offermanns, S. et al., "$G_{\alpha 15}$ and $G_{\alpha 18}$ Couple a Wide Variety of Receptors to Phospholipase C," *J. Biol. Chem.* 1995, 270 15175–15180.

Oslo et al., (eds.), in Remington's Pharmaceutical Sciences, 16th Edition, Mack Publishing Co., 1980.

Paikowitz, A.D. et al., "Structural evolution and pharmacology of a novel series of triacid angiotensin II receptor antagonists," *J. Med. Chem.,* 1994, 37, 4508–4521.

Palyha, O.C. et al., "Ligand activation domain of human orphan growth hormone (GH) secretagogue receptor (GHS–R) conserved from Pufferfish to humans," *Molecular Endocrinology,* Baltimore, M.D., U.S., vo. 14, No. 1, Jan. 2000m p. 160–169.

Parent, J. et al., "Mutations of two adjacent amino acids generate inactive and constitutively active forms of the human platelet–activating factor receptor," *J. Biol. Chem.,* 1996, 261(14), 7949–7955.

Parfitt, A.M. et al., "Hypercalcemia due to constitutive activity of the parathyroid hormone (PTH)PTH–related peptide receptor: comparison with primary hyperpatathyroidism," *J. Clin. Endocr. Metabl.,* 1996, 81, 3584–3588.

Parma, J. et al., "Somatic mutations in the thyrotopin receptor gene cause hyperfunctioning thyroid adenomas," *Nature* 1993, 365, 649–651.

Pauwels, et al., "Review Amino acid domains involved in constitutive activation of G–protein–coupled receptors," *Mol. Neurobiol.* (1996), 17 109–135.

Pei, G. et al., "A constitutive active mutant $\beta_2$–adrenergic receptor is constitutively desensitized and phosphorylated," *Proc. Natl. Acad. Sci. USA,* 1994, 91, 2699–2702.

Pendley, C.E. et al., "The gastrin/cholecystokinin–B receptor antagonist L–365,260 reduces basal acid secretion and prevents gastrointestinal damage induced by aspirin. ethanol and cysteamine in the rat," *J. Pharmacol. Exp. Ther.* 1993, 265(3), 1348–1354.

Peroutka, S., "Serotonin receptor subtypes. Their evolution and clinical relevance," *CNS Drugs,* 1995, 4 (Suppl. 1), 18–27.

Pettibone, D.J. et al., "Development and pharmacological assessment of novel peptide and nonpeptide oxytocin antagonists," *Regul. Pept.,* 1993, 45, 289–293.

Prat, M.P. et al., "The receptor encoded by the human c–Met oncogene is expressed in hepatocytes, epithelial cells and solid tumors," *Int. J. Cancer,* 1991, 49, 323–328.

Prezeua, L. et al., "Changes in the carboxy–terminal domain of metabotropic glutamate receptor 1 by alternate splicing generate receptors with differing agonist–independent activity," *Mol. Pharmacol.,* 1996, 49, 422–429.

Probst et al., "Sequence alignment of the G–protein coupled receptor superfamily," *DNA and Cell Biology* (1992) 11(1):1–20.

Rakovska, A. et al., "Effect of loxiglumide (CR 1505) on CCK–induced contractions and $^3$H–acetylcholine release from guinea–pig gallbladder," *Neuropeptides;* 1993, 25(5), 271–276.

Ren, Q. et al., "Constitutive active mutants of the $\alpha_2$–adrenergic receptor," *J. Biol. Chem.,* 1993, 268, 16483–16487.

Reppert, et al., "Cloning of a melatonin–related receptor from human pituitary," *FEBS Lett.* (1996) 386:219–225.

Reynolds, E.E. et al., "Pharmacological characterization of PD 156707, an orally active $ET_A$ receptor antagonist," *J. Pharmacol. Exp Ther,* 1995, 273(3), 1410–1417.

Robbins, L.S. et al., "Pigmentation phenotypes of variant extension locus alleles result from point mutations that alter MSH receptor function," *Cell,* 1993, 72, 827–834.

Rong, S. et al., "Met expression and sarcoma tumorigenicity," *Cancer* 1993, 53(22), 5355–5360.

Sakurai T. et al., "Orexins and Orexin Receptors: A Family of Hypothalamic Neuropeptides and G Protein–Coupled Receptors that Regulate Feeding Behavior," *Cell,* 92,573–585.

Salomon, Y. et al., "A highly sensitive adenylate cyclase assay," *Anal. Biochem.,* 1974, 58, 541–548.

Samama, Pa, et al., "A mutation–induced activation state of the β2–adrenergic receptor," *J. Biol. Chem.,* 1993, 268(7), 4625–4636.

Sautel, M. et al., "Neuropeptide Y and the nonpeptide antagonist BIBP 3226 share an overlapping binding site at the human Y1 receptor," *Am. Soc. Pharm. Exp. Ther.,* 1996, 50, 285–292.

Sawutz, D.G. et al., "Pharmacology and structure–activity relationships of the nonpeptide bradykinin receptor antagonist WIN 64338," *Can. J. Physiol. Pharmacol.,* 1995, 73, 805–811.

Scheer, A. et al., "The activation process of the $\alpha_{1B}$–adrenergic receptor: Potential role of protonation and hydrophobicity of a highly conserved aspartate," *Proc. Natl. Acad. Sci. USA,* 1997, 94, 808–813.

Scheer, A. et al., "Constitutively active Gprotein–coupled receptors: potential mechanisms of receptor activation," *J. Receptor Signal Transduction Res.* (1997) 17:57–73.

Schwinn, D.A. et al., "Cloning and pharmacological characterization of human Alpha–1 adrenergic receptors: sequence–corrections and direct comparison with other species homologues." *J. Pharmacol.* 1995, 272(1), 134–142.

Schild, L. et al., "A mutation in the epithelial sodium channel causing Liddle disease increases channel activity in the *Xenopus laevis* oocyte expression system," *Proc. Natl. Acad Sci USA,* 1995, 92, 5699–5703.

Seeman, P. et al., "Dopamine receptor pharmacology," *Trends Pharmacol. Sci.,* 1994, 15, 264–270.

Seeman, P. et al., "Dopamine D4 receptors elevated in schizophrenia," *Nature,* 1993, 365, 441–445.

Seifert, et al., "Different effects of G alpha splice variants on beta2 adrenoreceptor–mediated signalling," *J. Biol. Chem.* (1998) 273:5109–5116.

Serradeil–Le Gale, C. et al., "Biochemical and pharmacological properties of SR 49059, a new potent, nonpeptide antagonist of rat and hum vasopressin $V_{1a}$ receptors," *J. Clin. Invest.,* 1993, 92, 224–231.

Sharif, M. et al., "Malignant transformation by G Protein–coupled hormone receptors," *Mol. Cell. Endocrinology. Mol. Cell. Endocrinology.* 1994, 100, 115–119.

Showers, M.O. et al., "Activation of the erythropoietin receptor by the Friend spleen focus–forming virus gp55 glycoprotein induces constitutive protein tyrosine phosphorylation," *Blood,* 1992, 80(12), 3070–3078.

Shyrock et al., "Inverse agonists and neutral antagonists of recombinant human A1 adenosine receptors stably expressed in Chinese hamster ovary cells," *Mol. Pharmacol,* (1998) 53: 886–893.

Skinner, R.H. et al., "Direct measurement of the binding of RAS to neurofibromin using scintillation proximity assay," *Anal. Biochem.* 1994, 223, 259–265.

Skolnick, et al., "Structural genomics and its importance for gene function analysis," *Nature Biotechnol.* (2000) 18:283–287.

Slamon, D.J. et al., "Human breast cancer correlation of relapse and survival with amplication of the HER–2/neu oncogene," *Science,* 1987, 235, 177–181.

Slamon, D. et al., "Studies of the HER–*2Ineu proto oncogene* in human breast and ovarian cancer," *Science,* 1989, 244 707–712.

Smith D.R., "Sequencing of hum. chromosome 10", *EMBL Database Accession Number AC005849,* (1998).

Smith et al., "Assays of Cycle Nucleotides: A Review of Current Techniques," *App. Biochem Biotechnol* (1993) 41:189–218.

Song, Z. H. et al., "Molecular Cloning and Chromosomal Localization of Human Genes Encoding Three Closely Related G Protein–Coupled Receptors," *Genomics.* 1995, 28, 347–349.

Sonnhammer et al., "A hidden Markov model for predicting transmembrane helices in protein sequences," *Proc. Int. Conf. Intell. Syst. Mol. Biol.* (1998) 6:175–82.

Spiegel, A.M., "Defects in G protein–coupled signal transduction in human disease" *Ann. Rev. Physiol.,* 1995, 58, 143–170.

Stadel, et al., "Orphan G. Protein–Coupled Receptors: A neglected opportunity for pioneer drug discovery", *Trends in Pharm. Sciences,* 1997, 18, pp. 430–437.

Standaert and Young, Treatment of Central Nervous System Degenerative Disorders, Chapter 22, Section III, Drugs Acting on the Central Nervous System, in Goodman and Gilman's Pharmacological Basis of Therapeutics, 9th, ed. (1995) pp. 503–519.

Strausberg R., "National Cancer Institute, Cancer Genome Anatomy Project", *EMBL Database Accession Number AI090920,* 1998. (Abstract).

Strausberg R., "National Cancer Institute, Cancer Genome Anatomy Project", *EMBL Database Accessin Number AA804531,* 1998. (abstract).

Strausberg R., "National Cancer Institute, Cancer Genome Project", *EMBL Database Accession Number AI131555,* 1998. (abstract).

Suzuki, M. et al., "Regulatable Promoters for Use in Gene Therapy Applications: Modification of the 5–Flanking Region of the CFTR Gene with Multiple Camp Response Elements to support Basal, Low–Level Gene Expression that can be Upregulated by Exogenous Agents that Raise Intracellular Levels of Camp," *Human Gene Therapy,* 1996, 7, 1883–1893.

ter Laak, A. et al., "Modelling and mutation studies on the histamine H1–receptor agonist binding site reveal different binding modes for $H_1$–agonists. $Asp^{116}$ (TM3) has a constitutive role in receptor stimulation," *J. Computer–Aided Mol. Design,* 1995, 9, 319–330.

Thorens, "Expression cloning of the pancreatic beta cell receptor for the gluco–incretin hormone glucagon–like peptide 1," *Proc. Natl. Acad. Sci.* (1992) 89:8641–8645.

Thorens, "Glucagon–like peptide–1 and control of insulin secretion," *Diabete Metabolisme* (1995) 21:311–318.

Tiberi, M. et al., "High agonist–independent activity is a distinguishing feature of the dopamine D1B receptor subtype," *J. Biol. Chem.,* 1994, 269(45), 27925–27931.

Tsujimura, T. et al., "Constitutive activation of c–kit in FMA3 murine mastocytoma cells caused by deletion of seven amino acids at the juxtamembrane domain," *Blood,* 1996, 87(1), 273–283.

Usdin et al., "Gastric inhibitory polypeptide receptor, a member of the secretin–vasoactive intestinal peptide receptor family, is widely distributed in peripheral organs and the brain*," *Endocrinology* (1993) 133(6):2861–2870.

Volz, et al., "Molecular cloning, functional expression, and signal transduction of the GIP–reseptor cloned from a human insulinoma," *FEBS Lett.* (1995) 373:23–29.

Wang, Z. et al., "Constitutive μ opioid receptor activation as a regulatory mechanism underlying narcotic tolerance and dependence," *Life Sci.,* 1994, 54(20), 339–350.

Watowich, S.S. et al., "Homodimerization and constitutive activation of the erythropietin receptor," *Proc. Natl. Acad. Sci USA,* 1992, 89, 2140–2144.

Watson, S. and Arkinstall, S., *The G–Protein Linked Receptor Facts Book,* pp. 223–230, (1994).
Weber–Nordt, R.M. et al., "Constitutive activation of STAT proteins in primary lymphoid and myeloid leukemia cells and in Epstein–Barr virus (EBV)–related lymphoma cell lines," *Blood,* 1996, 83(3), 809–816.
Webster, M.K. et al., Constructive activation of fibroblast growth factor receptor 3 by the transmembrane point mutation found in achodronplasia, *EMBO J.,* 1996, 15, 520–527.
Wei et al., "Tissue–specific expression of the human receptor for glucagons–like peptide–I: brain, heart and pancreatic forms have the same deduced amino acid sequences," *FEBS Letters* (1995) 358:219–224.
Weng et al., "A DNA damage and stress inducible G protein– coupled receptor blocks cells in G2/M", *Proceedings of the National Acad of Sciences of USA* 1998, 95 whole document.
Wenzel–Seifert, et al., "High constitutive activity of the human formyl peptide receptor," *J. Biol.Chem.,* (1998) 273: 24181–24189.
Williams, S., "Human DNA Sequence From close 417022 on Chromosome 6q16.1–16.3.", *EMBL Database Entry HS417022,* 1998, pp. 1–34.
Wilson, et al., "Orphan G–protein–coupled receptors: the next generation of drug targets?," *Br. J. Pharmacol,* (1998) 126:1387–1392.
Wise, et al., "Rescue of functional interactions between the alpha–2A adrenoreceptor and acylation–resistant forms of Gi1–alpha by expressing the proteins from chimeric open reading frames," *J. Biol. Chem.* (1997) 272: 24673–24678.
Wollheim and Biden, "Second messenger function of inositol 1,4,5–triphosphate. Early changes in inositol phosphates, cytosolic Ca2+, and insulin release in carbamycholine–stimulated RINm5F cells," *J. Biol Chem.* (1986), 261: 8314–8319.
Xu, Y. et al., "Identification of Human OGR1, a Novel G. Protein–Coupled Receptor That Maps to Chromosome 14," *Genomincs,* 1996, 35, 397–402.
Xu, Y. et al., "Characterization of epidermal growth factor receptor gene expression in malignant and normal human cells lines," *Proc. Natl. Acad. Sci. USA,* 1984, 81, 7308–7312.
Yamada, K. et al., "Substitution of the insulin receptor transmembrane domain with the c–neu/erb B2 transmembrane domain constitutively activates the insulin receptor kinas in vitro," *J. Biol. Chem.,* 1992, 267(18), 12452–12461.
Zadina et al., "Endomorphins: novel endogenous μ–opiate receptor agonists in regions of high μ–opiate receptor density," *Annals New York Academy of Sciences* (1999) 897: 136–144.
Zhang, S. et al., "Identification of Dynorphins as Endogenous Ligands for an Opioid Receptor–Like Orphan Receptor," *J. Biol. Chem.,* 1995, 270, 22772–22776.
Zhang "Inositol 1,4,5–triphosphate mass assay," *Methods Mol Bio* (1998) 105:77–87.
Zhen, Z. et al., "Structural and functional domains critical for constitutive activation of the HGF–receptor (Met)," *Oncogene,* 1994, 9, 1691–1697.
The Sanger Institute: Data Release Policy, www.sanger.ac.uk, May 24, 2002.
Genbank Acc. #AL035423, update version of Feb. 12, 1999.
Genbank Acc. #AL035423, update version of Feb. 24, 1999.
Genbank Acc. #AL035423, update version of Feb. 27, 1999.
Genbank Acc. #AL035423, update version of Apr. 21, 1999.
Genbank Acc. #AL035423, update version of Nov. 23, 1999.
Sequence Revision History for Genbank Acc. #AL035423.Arena Pharmaceuticals, Inc. Announces Initiation of Phase 1 Clinical Trial of Arena Type 2 Diabetes Drug Candidate in Collaboration With Ortho–McNeil, Feb. 7, 2006, http://biz.yahoo.com/prnews/060207/latu106.html?.v=39, (3pp.).
Fehmann et al., End. Rev. 16: 390–410, 1995.*
U.S. Appl. No. 09/170,496, filed Oct. 13, 1998, Liaw et al.*
U.S. Appl. No. 09/364,425, filed Jul. 30, 1999, Behan et al.*
Doerks, et al., TIG, vol. 14, No. 6, Jun. 1998, pp. 248–250.*

* cited by examiner

| | 1 | 2 | 3 | 4 | 5 | 6 | 7 | 8 |
|---|---|---|---|---|---|---|---|---|
| A | | Amygdala | Caudate Nucleus | Cerebellum | Cerabral Cortex | Frontal Cortex | Hippocampus | Medulla Oblongata |
| B | Occipital Cortex | Putamen | Substantia Nigra | Temporal Cortex | Thalamus | Accumbens | Spinal Cord | |
| C | Heart | Aorta | Skeletal Muscle | Colon | Bladder | Uterus | Prostate | Stomach |
| D | Testis | Ovary | Pancreas | Pituitary | Adrenal Gland | Thyroid | Salivary Gland | Mammary Gland |
| E | Kidney | Liver | Small Intestine | Spleen | Thymus | Peripheral Leukocyte | Lymph Node | Bone Marrow |
| F | Appendix | Lung | Trachea | Placenta | | | | |
| G | Fetal Brain | Fetal Heart | Fetal Kidney | Fetal Liver | Fetal Spleen | Fetal Thymus | Fetal Lung | |
| H | | | | | | | | |

*FIG. 1A*

| | 1 | 2 | 3 | 4 | 5 | 6 | 7 | 8 | 9 | 10 | 11 | 12 |
|---|---|---|---|---|---|---|---|---|---|---|---|---|
| A | | Cerebellum Left | Substantia Nigra | Heart | Esophagus | Colon Transverse | Kidney | Lung | Liver | Leukemia HL-60 | Fetal Brain | |
| B | Cerebral Cortex | Cerebellum Right | Accumbens | Aorta | Stomach | Colon Desending | Skeletal Muscle | Placenta | Pancreas | HeLa S3 | Fetal Heart | |
| C | Frontal Cortex | Corpus Callosum | Thalamus | Atrium Left | Duodenum | Rectum | Spleen | Bladder | Adrenal Gland | Leukemia K562 | Fetal Kidney | |
| D | Parietal Lobe | Amygdala | Pituitary Gland | Atrium Right | Jejunum | | Thymus | Uterus | Thyroid | Leukemia MOLT-4 | Fetal Liver | |
| E | Occipital Cortex | Claudete Nucleus | Spinal Cord | Ventricle Left | Ileum | | Peripheral Leukocyte | Prostate | Salivary Gland | Burkitt's Lymphoma Raji | Fetal Spleen | |
| F | Temporal Cortex | Hippocampus | | Ventricle Right | Ilocecum | | Lymph Node | Testis | Mammary Gland | Burkitt's Lymphoma Daudi | Fetal Thymus | |
| G | Paracentral Gyrus of Cerebral Cortex | Medulla Oblongata | | Inter Ventricular Septum | Appendix | | Bone Marrow | Ovary | | Colorectal Adenocarcinoma SW480 | Fetal Lung | |
| H | Pons | Putamen | | Apex of the Heart | Colon Ascending | | Trachea | | | Lung Carcinoma A549 | | |

*FIG. 1B*

METHOD OF IDENTIFYING A COMPOUND FOR INHIBITING OR STIMULATING HUMAN G PROTEIN-COUPLED RECEPTORS

Matter enclosed in heavy brackets [ ] appears in the original patent but forms no part of this reissue specification; matter printed in italics indicates the additions made by reissue.

This application is a continuation of *Application* Ser. No. 10/272,983, filed Oct. 17, 2002, which is a continuation of *Application* Ser. No. 09/417,044, filed Oct. 12, 1999, now abandoned, and claims priority benefit of Provisional Application [Ser.] No. 60/121,852 filed Feb. 26, 1999, [Ser.] *Provisional Application* No. 60/109,213, filed Nov. 20, 1998, [Ser.] *Provisional Application* No. 60/120,416, filed Feb. 16, 1999, [Ser.] *Provisonal Application* No. 60/123,946, filed Mar. 12, 1999, [Ser.] *Provisional Application* No. 60/123,949, filed Mar. 12, 1999, [Ser.] *Provisonal Application* No. 60/136,436, filed May 28, 1999, [Ser.] *Provisional Application* No. 60/136,439, [field] *filed* May 28, 1999, [Ser.] *Provisional Application* No. 60/136,567, [file] *filed* May 28, 1999, [Ser.] *Provisional Application* No. 60/137,127, filed May 28, 1999, [Ser.] *Provisional Application* No. 60/137,131, filed May 28, 1999, [Ser.] *Provisional Application* No. 60/141,448, filed Jun. 29, 1999, [Ser.] *Provisional Application* No. 60/136,437, filed May 28, 1999, [Ser.] *Provisional Application* No. 60/156,653, filed Sep. 29, 1999, [Ser.] *Provisional Application* No. [60/156,333] *60/156,633*, filed Sep. [28] *29*, 1999, [Ser.] *Provisional Application* No. 60/156,555, filed Sep. 29, 1999, [Ser.] *Provisional Application* No. 60/156,634, filed Sep. 29, 1999, [Ser.] *Provisional Application* No. 60/157,280, filed Oct. 1, 1999, [Ser.] *Provisional Application* No. 60/157,294, filed Oct. 1, 1999, [Ser.] *Provisional Application* No. 60/157,281, filed Oct. 1, 1999, [Ser.] *Provisional Application No.* 60/157,293, filed Oct. 1, 1999, and [Ser.] *Provisional Application* No. 60/157,282, filed Oct. 1, 1999, the entirety of each of which is incorporated herein by reference. This patent application is related to U.S. [Ser.] *Application* No. 09/170,496, filed Oct. 13, 1999, and U.S. [Ser.] *Application* No. 09/416,760, filed Oct. 12, 1999, both being incorporated herein by reference in their entirety. This patent application is also related to U.S. [Ser.] *Application* No. 09/364,425, filed Jul. 30, 1999, which is incorporated herein by reference in its entirety.

FIELD OF THE INVENTION

The invention disclosed in this patent document relates to transmembrane receptors, and more particularly to endogenous, orphan, human G protein-coupled receptors ("GPCRs").

BACKGROUND OF THE INVENTION

Although a number of receptor classes exist in humans, by far the most abundant and therapeutically relevant is represented by the G protein-coupled receptor (GPCR or GPCRs) class. It is estimated that there are some 100,000 genes within the human genome, and of these, approximately 2% or 2,000 genes, are estimated to code for GPCRs. Receptors, including GPCRs, for which the endogenous ligand has been identified are referred to as "known" receptors, while receptors for which the endogenous ligand has not been identified are referred to as "orphan" receptors. GPCRs represent an important area for the development of pharmaceutical products: from approximately 20 of the 100 known GPCRs, 60% of all prescription pharmaceuticals have been developed.

This distinction is not merely semantic, particularly in the case of GPCRs. Thus, the orphan GPCRs are to the pharmaceutical industry what gold was to California in the late $19^{th}$ century—an opportunity to drive growth, expansion, enhancement and development.

GPCRs share a common structural motif. All these receptors have seven sequences of between 22 to 24 hydrophobic amino acids that form seven alpha helices, each of which spans the membrane (each span is identified by number, i.e., transmembrane-1 (TM-1), transmembrane-2 (TM-2), etc.). The transmembrane helices are joined by strands of amino acids between transmembrane-2 and transmembrane-3, transmembrane-4 and transmembrane-5, and transmembrane-6 and transmembrane-7 on the exterior, or "extracellular" side, of the cell membrane (these are referred to as "extracellular" regions 1, 2 and 3 (EC-1, EC-2 and EC-3), respectively). The transmembrane helices are also joined by strands of amino acids between transmembrane-1 and transmembrane-2, transmembrane-3 and transmembrane-4, and transmembrane-5 and transmembrane-6 on the interior, or "intracellular" side, of the cell membrane (these are referred to as "intracellular" regions 1, 2 and 3 (IC-1, IC-2 and IC-3), respectively). The "carboxy" ("C") terminus of the receptor lies in the intracellular space within the cell, and the "amino" ("N") terminus of the receptor lies in the extracellular space outside of the cell.

Generally, when an endogenous ligand binds with the receptor (often referred to as "activation" of the receptor), there is a change in the conformation of the intracellular region that allows for coupling between the intracellular region and an intracellular "G-protein." It has been reported that GPCRs are "promiscuous" with respect to G proteins, i.e., that a GPCR can interact with more than one G protein. See, Kenakin, T, 43 Life Sciences 1095 (1988). Although other G proteins exist, currently, Gq, Gs, Gi, and Go are G proteins that have been identified. Endogenous ligand-activated GPCR coupling with the G-protein begins a signaling cascade process (referred to as "signal transduction"). Under normal conditions, signal transduction ultimately results in cellular activation or cellular inhibition. It is thought that the IC-3 loop as well as the carboxy terminus of the receptor interact with the G protein.

Under physiological conditions, GPCRs exist in the cell membrane in equilibrium between two different conformations: an "inactive" state and an "active" state. A receptor in an inactive state is unable to link to the intracellular signaling transduction pathway to produce a biological response. Changing the receptor conformation to the active state allows linkage to the transduction pathway (via the G-protein) and produces a biological response. A receptor may be stabilized in an active state by an endogenous ligand or a compound such as a drug.

SUMMARY OF THE INVENTION

Disclosed herein are human endogenous orphan G protein-coupled receptors.

BRIEF DESCRIPTION OF THE DRAWINGS

FIGS. 1A and 1B provide reference "grids" for certain dot-blots provided herein (see also, FIGS. 2A and 2B, respectively).

DETAILED DESCRIPTION

Figure 2A:
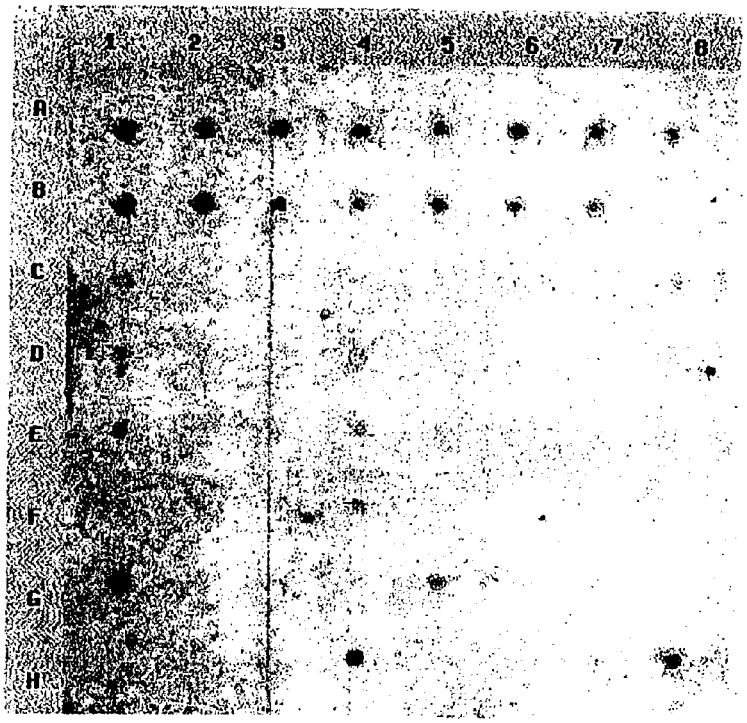
FIGS. 2A and 2B provide reproductions of the results of certain dot-blot analyses resulting from hCHN3 and hCHN8, respectively (see also, FIGS. 1A and 1B, respectively).

The scientific literature that has evolved around receptors has adopted a number of terms to refer to ligands having various effects on receptors. For clarity and consistency, the following definitions will be used throughout this patent document. To the extent that these definitions conflict with other definitions for these terms, the following definitions shall control:

AMINO ACID ABBREVIATIONS used herein are set out in Table 1:

TABLE 1

| | | |
|---|---|---|
| ALANINE | ALA | A |
| ARGININE | ARG | R |
| ASPARAGINE | ASN | N |
| ASPARTIC ACID | ASP | D |
| CYSTEINE | CYS | C |
| GLUTAMIC ACID | GLU | E |
| GLUTAMINE | GLN | Q |
| GLYCINE | GLY | G |
| HISTIDINE | HIS | H |
| ISOLEUCINE | ILE | I |
| LEUCINE | LEU | L |
| LYSINE | LYS | K |
| METHIONINE | MET | M |
| PHENYLALANINE | PHE | F |
| PROLINE | PRO | P |
| SERINE | SER | S |
| THREONINE | THR | T |
| TRYPTOPHAN | TRY | W |
| TYROSINE | TYR | Y |
| VALINE | VAL | V |

COMPOSITION means a material comprising at least one component.

ENDOGENOUS shall mean a material that a mammal naturally produces. ENDOGENOUS in reference to, for example and not limitation, the term "receptor," shall mean that which is naturally produced by a mammal (for example, and not limitation, a human) or a virus. By contrast, the term NON-ENDOGENOUS in this context shall mean that which is not naturally produced by a mammal (for example, and not limitation, a human) or a virus.

HOST CELL shall mean a cell capable of having a Plasmid and/or Vector incorporated therein. In the case of a prokaryotic Host Cell, a Plasmid is typically replicated as a autonomous molecule as the Host Cell replicates (generally, the Plasmid is thereafter isolated for introduction into a eukaryotic Host Cell); in the case of a eukaryotic Host Cell, a Plasmid is integrated into the cellular DNA of the Host Cell such that when the eukaryotic Host Cell replicates, the Plasmid replicates. Preferably, for the purposes of the invention disclosed herein, the Host Cell is eukaryotic, more preferably, mammalian, and most preferably selected from the group consisting of 293, 293T and COS-7 cells.

LIGAND shall mean an endogenous, naturally occurring molecule specific for an endogenous, naturally occurring receptor.

*MUTANT or MUTATION in reference to an endogenous receptor's nucleic acid and/or amino acid sequence shall mean a specified change or changes to such endogenous sequences such that a mutated form of an endogenous, non-constitutively activated receptor evidences constitutive activation of the receptor. In terms of equivalents to specific sequences, a subsequent mutated form of a human receptor is considered to be equivalent to a first mutation of the human receptor if (a) the level of constitutive activation of the subsequent mutated form of the receptor is substantially the same as that evidenced by the first mutation of the receptor; and (b) the percent sequence (amino acid and/or nucleic acid) homology between the subsequent mutated form of the receptor and the first mutation of the receptor is at least about 80%, more preferably at least about 90% and most preferably at least 95%. Ideally, and owing to the fact that the most preferred mutation disclosed herein for achieving constitutive activation includes a single amino acid and/or codon change between the endogenous and the non-endogenous forms of the GPCR, the percent sequence homology should be at least 98%.*

NON-ORPHAN RECEPTOR shall mean an endogenous naturally occurring molecule specific for an endogenous naturally occurring ligand wherein the binding of a ligand to a receptor activates an intracellular signaling pathway.

ORPHAN RECEPTOR shall mean an endogenous receptor for which the endogenous ligand specific for that receptor has not been identified or is not known.

PLASMID shall mean the combination of a Vector and cDNA. Generally, a Plasmid is introduced into a Host Cell for the purposes of replication and/or expression of the cDNA as a protein.

VECTOR sin reference to cDNA shall mean a circular DNA capable of incorporating at least one cDNA and capable of incorporation into a Host Cell.

The order of the following sections is set forth for presentational efficiency and is not intended, nor should be construed, as a limitation on the disclosure or the claims to follow.

Identification of Human GPCRs

The efforts of the Human Genome project have led to the identification of a plethora of information regarding nucleic acid sequences located within the human genome; it has been the case in this endeavor that genetic sequence information has been made available without an understanding or recognition as to whether or not any particular genomic sequence does or may contain open-reading frame information that translate human proteins. Several methods of identifying nucleic acid sequences within the human genome are within the purview of those having ordinary skill in the art. For example, and not limitation, a variety of GPCRs, disclosed herein, were discovered by reviewing the GenBank™ database, while other GPCRs were discovered by utilizing a nucleic acid sequence of a GPCR, previously sequenced, to conduct a BLAST™ search of the EST database. Table A, below, lists the disclosed endogenous orphan GPCRs along with a GPCR's respective homologous GPCR:

TABLE A

| Disclosed Human Orphan GPCRs | Accession Number Identified | Open Reading Frame (Base Pairs) | Percent Homology To Designated GPCR | Reference To Homologous GPCR (Accession No.) |
|---|---|---|---|---|
| hARE-3 | AL033379 | 1,260 bp | 52.3% LPA-R | U92642 |
| hARE-4 | AC006087 | 1,119 bp | 36% P2Y5 | AF000546 |
| hARE-5 | AC006255 | 1,104 bp | 32% Oryzias latipes | D43633 |
| hGPR27 | AA775870 | 1,128 bp | | |
| hARE-1 | AI090920 | 999 bp | 43% KIAA0001 | D13626 |
| hARE-2 | AA359504 | 1,122 bp | 53% GPR27 | |
| hPPR1 | H67224 | 1,053 bp | 39% EBI1 | L31581 |
| hG2A | AA754702 | 1,113 bp | 31% GPR4 | L36148 |
| hRUP3 | AI035423 | 1,005 bp | 30% Drosophila melanogaster | 2133653 |
| hRUP4 | AI307658 | 1,296 bp | 32% pNPGPR 28% and 29% Zebra fish Ya and Yb, respectively | NP_004876 AAC41276 and AAB94616 |
| hRUP5 | AC005849 | 1,413 bp | 25% DEZ 23% FMLPR | Q99788 P21462 |
| hRUP6 | AC005871 | 1,245 bp | 48% GPR66 | NP_006047 |
| hRUP7 | AC007922 | 1,173 bp | 43% H3R | AF140538 |
| hCHN3 | EST 36581 | 1,113 bp | 53% GPR27 | |
| hCHN4 | AA804531 | 1,077 bp | 32% thrombin | 4503637 |
| hCHN6 | EST 2134670 | 1,503 bp | 36% edg-1 | NP_001391 |
| hCHN8 | EST 764455 | 1,029 bp | 47% KIAA0001 | D13626 |
| hCHN9 | EST 1541536 | 1,077 bp | 41% LTB4R | NM_000752 |
| hCHN10 | EST 1365839 | 1,055 bp | 35% P2Y | NM_002563 |

Receptor homology is useful in terms of gaining an appreciation of a role of the disclosed receptors within the human body. Additionally, such homology can provide insight as to possible endogenous ligand(s) that may be natural activators for the disclosed orphan GPCRs.

B. Receptor Screening

Techniques have become more readily available over the past few years for endogenous-ligand identification (this, primarily, for the purpose of providing a means of conducting receptor-binding assays that require a receptor's endogenous ligand) because the traditional study of receptors has always proceeded from the a priori assumption (historically based) that the endogenous ligand must first be identified before discovery could proceed to find antagonists and other molecules that could affect the receptor. Even in cases where an antagonist might have been known first, the search immediately extended to looking for the endogenous ligand. This mode of thinking has persisted in receptor research even after the discovery of constitutively activated receptors. What has not been heretofore recognized is that it is the active state of the receptor that is most useful for discovering agonists, partial agonists, and inverse agonists of the receptor. For those diseases which result from an overly active receptor or an under-active receptor, what is desired in a therapeutic drug is a compound which acts to diminish the active state of a receptor or enhance the activity of the receptor, respectively, not necessarily a drug which is an antagonist to the endogenous ligand. This is because a compound that reduces or enhances the activity of the active receptor state need not bind at the same site as the endogenous ligand. Thus, as taught by a method of this invention, any search for therapeutic compounds should start by screening compounds against the ligand-independent active state.

As is known in the art, GPCRs can be "active" in their endogenous state even without the binding of the receptor's endogenous ligand thereto. Such naturally-active receptors can be screened for the direct identification (i.e., without the need for the receptor's endogenous ligand) of, in particular, inverse agonists. Alternatively, the receptor can be "activated" via, e.g., mutation of the receptor to establish a non-endogenous version of the receptor that is active in the absence of the receptor's endogenous ligand.

Screening candidate compounds against an endogenous or non-endogenous, constitutively activated version of the human orphan GPCRs disclosed herein can provide for the direct identification of candidate compounds which act at this cell surface receptor, without requiring use of the receptor's endogenous ligand. By determining areas within the body where the endogenous version of human GPCRs disclosed herein is expressed and/or over-expressed, it is possible to determine related disease/disorder states which are associated with the expression and/or over-expression of the receptor; such an approach is disclosed in this patent document.

With respect to creation of a mutation that may evidence constitutive activation of human orphan GPCRs disclosed herein is based upon the distance from the proline residue at which is presumed to be located within TM6 of the GPCR typically nears the TM6/IC3 interface (such proline residue appears to be quite conserved). By mutating the amino acid residue located 16 amino acid residues from this residue (presumably located in the IC3 region of the receptor) to, most preferably, a lysine residue, such activation may be obtained. Other amino acid residues may be useful in the mutation at this position to achieve this objective.

C. Disease/Disorder Identification and/or Selection

Preferably, the DNA sequence of the human orphan GPCR can be used to make a probe for (a) dot-blot analysis against tissue-mRNA, and/or (b) RT-PCR identification of the expression of the receptor in tissue samples. The presence of a receptor in a tissue source, or a diseased tissue, or the presence of the receptor at elevated concentrations in diseased tissue compared to a normal tissue, can be preferably utilized to identify a correlation with a treatment regimen, including but not limited to, a disease associated with that disease. Receptors can equally well be localized to regions of organs by this technique. Based on the known functions of the specific tissues to which the receptor is localized, the putative functional role of the receptor can be deduced.

As the data below indicate, RUP3 is expressed within the human pancreas, suggesting that RUP3 may play a role in insulin regulation and/or glucagon regulation. Accordingly, candidate compounds identified using a constitutively activated form of RUP3 may be useful for understanding the role of RUP3 in diabetes and/or as therapeutics for diabetes.

D. Screening of Candidate Compounds

1. Generic GPCR Screening Assay Techniques

When a G protein receptor becomes constitutively active (i.e., active in the absence of endogenous ligand binding thereto), it binds to a G protein (e.g., Gq, Gs, Gi, Go) and stimulates the binding of GTP to the G protein. The G protein then acts as a GTPase and slowly hydrolyzes the GTP to GDP, whereby the receptor, under normal conditions, becomes deactivated. However, constitutively activated receptors continue to exchange GDP to GTP. A non-hydrolyzable analog of GTP, [$^{35}$S]GTPγS, can be used to monitor enhanced binding to membranes which express constitutively activated receptors. It is reported that [$^{35}$S] GTPγS can be used to monitor G protein coupling to membranes in the absence and presence of ligand. An example of this monitoring, among other examples well-known and available to those in the art, was reported by Traynor and Nahorski in 1995. The preferred use of this assay system is for initial screening of candidate compounds because the system is generically applicable to all G protein-coupled receptors regardless of the particular G protein that interacts with the intracellular domain of the receptor.

2. Specific GPCR Screening Assay Techniques

Once candidate compounds are identified using the "generic" G protein-coupled receptor assay (i.e., an assay to select compounds that are agonists, partial agonists, or inverse agonists), further screening to confirm that the compounds have interacted at the receptor site is preferred. For example, a compound identified by the "generic" assay may not bind to the receptor, but may instead merely "uncouple" the G protein from the intracellular domain.

a. Gs and Gi.

Gs stimulates the enzyme adenylyl cyclase. Gi (and Go), on the other hand, inhibit this enzyme. Adenylyl cyclase catalyzes the conversion of ATP to cAMP; thus, constitutively activated GPCRs that couple the Gs protein are associated with increased cellular levels of cAMP. On the other hand, constitutively activated GPCRs that couple the Gi (or Go) protein are associated with decreased cellular levels of cAMP. See, generally, "Indirect Mechanisms of Synaptic Transmission," Chpt. 8, From Neuron To Brain (3rd Ed.) Nichols, J. G. et al eds. Sinauer Associates, Inc. (1992). Thus, assays that detect cAMP can be utilized to determine if a candidate compound is, e.g., an inverse agonist to the receptor (i.e., such a compound would decrease the levels of cAMP). A variety of approaches known in the art for measuring cAMP can be utilized; a most preferred approach relies upon the use of anti-cAMP antibodies in an ELISA-based format. Another type of assay that can be utilized is a whole cell second messenger reporter system assay. Promoters on genes drive the expression of the proteins that a particular gene encodes. Cyclic AMP drives gene expression by promoting the binding of a cAMP-responsive DNA binding protein or transcription factor (CREB) which then binds to the promoter at specific sites called cAMP response elements and drives the expression of the gene. Reporter systems can be constructed which have a promoter containing multiple cAMP response elements before the reporter gene, e.g., β-galactosidase or luciferase. Thus, a constitutively activated Gs-linked receptor causes the accumulation of cAMP that then activates the gene and expression of the reporter protein. The reporter protein such as β-galactosidase or luciferase can then be detected using standard biochemical assays (Chen et al. 1995).

Go and Gq.

Gq and Go are associated with activation of the enzyme phospholipase C, which in turn hydrolyzes the phospholipid $PIP_2$, releasing two intracellular messengers: diacycloglycerol (DAG) and inistol 1,4,5-triphoisphate ($IP_3$). Increased accumulation of $IP_3$ is associated with activation of Gq- and Go-associated receptors. See, generally, "Indirect Mechanisms of Synaptic Transmission," Chpt. 8, From Neuron To Brain (3rd Ed.) Nichols, J. G. et al eds. Sinauer Associates, Inc. (1992). Assays that detect $IP_3$ accumulation can be utilized to determine if a candidate compound is, e.g., an inverse agonist to a Gq- or Go-associated receptor (i.e., such a compound would decrease the levels of IP3). Gq-dependent receptors can also been examined using an API reporter assay in that Gq-dependent phospholipase C causes activation of genes containing API elements; thus, activated Gq-associated receptors will evidence an increase in the expression of such genes, whereby inverse agonists thereto will evidence a decrease in such expression, and agonists will evidence an increase in such expression. Commercially available assays for such detection are available.

3. GPCR Fusion Protein

The use of an endogenous, constitutively activated orphan GPCR, or a non-endogenous, constitutively activated orphan GPCR, for screening of candidate compounds for the direct identification of inverse agonists, agonists and partial agonists provides a unique challenge in that, by definition, the receptor is active even in the absence of an endogenous ligand bound thereto. Thus, it is often useful that an approach be utilized that can enhance the signal obtained by the activated receptor. A preferred approach is the use of a GPCR Fusion Protein.

Generally, once it is determined that a GPCR is or has been constitutively activated, using the assay techniques set forth above (as well as others), it is possible to determine the predominant G protein that couples with the endogenous GPCR. Coupling of the G protein to the GPCR provides a signaling pathway that can be assessed. Because it is most preferred that screening take place by use of a mammalian expression system, such a system will be expected to have endogenous G protein therein. Thus, by definition, in such a system, the constitutively activated orphan GPCR will continuously signal. In this regard, it is preferred that this signal be enhanced such that in the presence of, e.g., an inverse agonist to the receptor, it is more likely that it will be able to more readily differentiate, particularly in the context of screening, between the receptor when it is contacted with the inverse agonist.

The GPCR Fusion Protein is intended to enhance the efficacy of G protein coupling with the GPCR. The GPCR Fusion Protein is preferred for screening with a non-endogenous, constitutively activated GPCR because such an approach increases the signal that is most preferably utilized in such screening techniques, although the GPCR Fusion Protein can also be (and preferably is) used with an endogenous, constitutively activated GPCR. This is important in facilitating a significant "signal to noise" ratio; such a significant ratio is import preferred for the screening of candidate compounds as disclosed herein.

The construction of a construct useful for expression of a GPCR Fusion Protein is within the purview of those having ordinary skill in the art. Commercially available expression vectors and systems offer a variety of approaches that can fit the particular needs of an investigator. The criteria of importance for such a GPCR Fusion Protein construct is that the GPCR sequence and the G protein sequence both be in-frame (preferably, the sequence for the GPCR is upstream of the G protein sequence) and that the "stop" codon of the GPCR must be deleted or replaced such that upon expression of the GPCR, the G protein can also be expressed. The GPCR can be linked directly to the G protein, or there can be spacer residues between the two (preferably, no more than about 12, although this number can be readily ascertained by one of ordinary skill in the art). We have a preference (based upon convenience) of use of a spacer in that some restriction sites that are not used will, effectively, upon expression, become a spacer. Most preferably, the G protein that couples to the GPCR will have been identified prior to the creation of the GPCR Fusion Protein construct. Because there are only a few G proteins that have been identified, it is preferred that a construct comprising the sequence of the G protein (i.e., a universal G protein construct) be available for insertion of an endogenous GPCR sequence therein; this provides for efficiency in the context of large-scale screening of a variety of different endogenous GPCRs having different sequences.

E. Other Utility

Although a preferred use of the human orphan GPCRs disclosed herein may be for the direct identification of candidate compounds as inverse agonists, agonists or partial agonists (preferably for use as pharmaceutical agents), these versions of human GPCRs can also be utilized in research settings. For example, in vitro and in vivo systems incorporating GPCRs can be utilized to further elucidate and understand the roles these receptors play in the human condition, both normal and diseased, as well as understanding the role of constitutive activation as it applies to understanding the signaling cascade. The value in human orphan GPCRs is that its utility as a research tool is enhanced in that by determining the location(s) of such receptors within the body, the GPCRs can be used to understand the role of these receptors in the human body before the endogenous ligand therefor is identified. Other uses of the disclosed receptors will become apparent to those in the art based upon, inter alia, a review of this patent document.

Although a preferred use of the non-endogenous versions of the human RUP3 disclosed herein may be for the direct identification of candidate compounds as inverse agonists, agonists or partial agonists (preferably for use as pharmaceutical agents), this version of human RUP3 can also be utilized in research settings. For example, in vitro and in vivo systems incorporating RUP3 can be utilized to further elucidate the roles RUP3 plays in the human condition, particularly with respect to the human pancreas, both nonnal and diseased (and in particular, diseases involving regulation of insulin or glucagon, e.g., diabetes), as well as understanding the role of constitutive activation as it applies to understanding the signaling cascade. A value in non-endogenous human RUP3 is that its utility as a research tool is enhanced in that, because of its unique features, non-endogenous RUP3 can be used to understand the role of RUP3 in the human body before the endogenous ligand therefor is identified. Other uses of the disclosed receptors will become apparent to those in the art based upon, inter alia, a review of the patent document.

EXAMPLES

The following examples are presented for purposes of elucidation, and not limitation, of the present invention. While specific nucleic acid and amino acid sequences are disclosed herein, those of ordinary skill in the art are credited with the ability to make minor modifications to these sequences while achieving the same or substantially similar results reported below. Unless otherwise indicated below, all nucleic acid sequences for the disclosed endogenous orphan human GPCRs have been sequenced and verified. For purposes of equivalent receptors, those of ordinary skill in the art will readily appreciate that conservative substitutions can be made to the disclosed sequences to obtain a functionally equivalent receptor.

Example 1

Endogenous Human GPCRs

1. Identification of Human GPCRs

Several of the disclosed endogenous human GPCRs were identified based upon a review of the GenBank database information. While searching the database, the following cDNA clones were identified as evidenced below.

| Disclosed Human Orphan GPCRs | Accession Number | Complete DNA Sequence (Base Pairs) | Open Reading Frame (Base Pairs) | Nucleic Acid SEQ ID. NO. | Amino Acid SEQ ID. NO. |
|---|---|---|---|---|---|
| hARE-3 | AL033379 | 111,389 bp | 1,260 bp | 1 | 16 |
| hARE-4 | AC006087 | 226,925 bp | 1,119 bp | 3 | 4 |
| hARE-5 | AC006255 | 127,605 bp | 1,104 bp | 5 | 6 |
| hRUP3 | AL035423 | 140,094 bp | 1,005 bp | 7 | 8 |
| hRUP5 | AC005849 | 169,144 bp | 1,413 bp | 9 | 10 |
| hRUP6 | AC005871 | 218,807 bp | 1,245 bp | 11 | 12 |
| hRUP7 | AC007922 | 158,858 bp | 1,173 bp | 13 | 14 |

Other disclosed endogenous human GPCRs were identified by conducting a BLAST search of EST database (dbest) using the following EST clones as query sequences. The following EST clones identified were then used as a probe to screen a human genomic library.

| Disclosed Human Orphan GPCRs | Query (Sequence) | EST Clone/ Accession No. Identified | Open Reading Frame (Base Pairs) | Nucleic Acid SEQ ID. NO. | Amino Acid SEQ ID. NO. |
|---|---|---|---|---|---|
| hGPCR27 | Mouse GPCR27 | AA775870 | 1,125 bp | 15 | 16 |
| hARE-1 | TDAG | 1689643 AI090920 | 999 bp | 17 | 18 |
| hARE-2 | GPCR27 | 68530 AA359504 | 1,122 bp | 19 | 20 |
| hPPR1 | Bovine PPR1 | 238667 H67224 | 1,053 bp | 21 | 22 |
| hG2A | Mouse 1179426 | See Example 2(a) below | 1,113 bp | 23 | 24 |
| hCHN3 | N.A. | EST 36581 (full length) | 1,113 bp | 25 | 26 |
| hCHN4 | TDAG | 1184934 AA804531 | 1,077 bp | 27 | 28 |
| hCHN6 | N.A. | EST 2134670 (full length) | 1,503 bp | 29 | 30 |
| hCHN8 | KIAA0001 | EST 76445 | 1,029 bp | 31 | 32 |
| hCHN9 | 1365839 | EST 1541536 | 1,077 bp | 33 | 34 |
| hCHN10 | Mouse EST 1365839 | Human 1365839 | 1,005 bp | 35 | 36 |
| hRUP4 | N.A. | AI307658 | 1,296 bp | 37 | 39 |

N.A. = "not applicable"

2. Full Length Cloning a. hG2A (Seq. Id. Nos. 23 & 24)

Mouse EST clone 1179426 was used to obtain a human genomic clone containing all but three amino acid hG2A coding sequences. The 5'end of this coding sequence was obtained by using 5'RACE™, and the template for PCR was Clontech's Human Spleen Marathon-ready™ cDNA. The disclosed human G2A was amplified by PCR using the G2A cDNA specific primers for the first and second round PCR as shown in SEQ. ID. NO.: 39 and SEQ. ID. NO.: 40 as follows:

5'-CTGTGTACAGCAGTTCGCAGAGTG-3'(SEQ. ID. NO.: 39; $1^{st}$ round PCR)

5'-GAGTGCCAGGCAGAGCAGGTAGAC-3'(SEQ. ID. NO.: 40; second round PCR).

PCR was performed using Advantage™ GC Polymerase Kit (Clontech; manufacturing instructions will be followed), at 94° C. for 30 sec followed by 5 cycles of 94° C. for 5 sec and 72° C. for 4 min; and 30 cycles of 94° for 5 sec and 70° for 4 min. An approximate 1.3 Kb PCR fragment was purified from agarose gel, digested with Hind III and Xba I and cloned into the expression vector pRC/CMV2 (Invitrogen). The cloned-insert was sequenced using the T7 Sequenase™ kit (USB Amersham; manufacturer instructions will be followed) and the sequence was compared with the presented sequence. Expression of the human G2A will be detected by probing an RNA dot blot (Clontech; manufacturer instructions will be followed) with the $P^{32}$-labeled fragment.

b. hCHN9 (Seq. Id. Nos. 33 & 34)

Sequencing of the EST clone 1541536 indicated that hCHN9 is a partial cDNA clone having only an initiation codon; ie., the termination codon was missing. When hCHN9 was used to "blast" against the data base (nr), the 3' sequence of hCHN9 was 100% homologous to the 5' untranslated region of the leukotriene B4 receptor cDNA, which contained a termination codon in the frame with hCHN9 coding sequence. To determine whether the 5' untranslated region of LTB4R cDNA was the 3' sequence of hCHN9, PCR was performed using primers based upon the 5' sequence flanking the initiation codon found in hCHN9 and the 3' sequence around the termination codon found in the LTB4R 5' untranslated region. The 5' primer sequence utilized was as follows:

5'-CCCGAATTCCTGCTFGCTCCCAGCTTGGCCC-3' SEQ. ID. NO.: 41; sense) and

5'-TGTGGATCCTGCTGTCAAAGGTCCCATTCCGG-3' (SEQ. ID. NO.: 42; antisense).

PCR was performed using thymus cDNA as a template and rTth polymerase (Perkin Elmer) with the buffer system provided by the manufacturer, 0.25 uM of each primer, and 0.2 mM of each 4 nucleotides. The cycle condition was 30 cycles of 94° C. for 1 min, 65° C. for 1 min and 72° C. for 1 min and 10 sec. A 1.1 kb fragment consistent with the predicted size was obtained from PCR. This PCR fragment was subcloned into pCMV (see below) and sequenced (see, SEQ. ID. NO.: 33).

c. hRUP4 (Seq. Id. Nos. 37 & 38)

The full length hRUP4 was cloned by RT-PCR with human brain cDNA (Clontech) as templates:

5'-TCACAATGCTAGGTGTGGTC-3' (SEQ. ID. NO.: 43; sense) and

5'-TGCATAGACAATGGGATTACAG-3' (SEQ. ID. NO.: 44; antisense).

PCR was performed using TaqPlus™ Precision™ polymerase (Stratagene; manufacturing instructions will be followed) by the following cycles: 94° C. for 2 min; 94° C. 30 sec; 55° C. for 30 sec, 72° C. for 45 sec, and 72° C. for 10 min. Cycles 2 through 4 were repeated 30 times.

The PCR products were separated on a 1% agarose gel and a 500 bp PCR fragment was isolated and cloned into the pCRII-TOPO vector (Invitrogen) and sequenced using the T7 DNA Sequenase™ kit (Amsham) and the SP6/T7 primers (Stratagene). Sequence analysis revealed that the PCR fragment was indeed an alternatively spliced form of AI307658 having a continuous open reading frame with similarity to other GPCRs. The completed sequence of this PCR fragment was as follows:

```
5'-TCACAATGCTAGGTGTGGTCTGGCTGGTG (SEQ. ID. NO.: 45)
GCAGTCATAGTAGGATCACCATGTGGCACGTG
CAACAACTTGAGATCAAATCTGACTTCCTATA
TGAAAAGGAACACATCTGCTGCTTAGAAGAGT
GGACCAGCCCTGTGCACCAGAAGATCTACACC
ACCTTCATCCTTGTCATCCTCTTCCTCCTGCC
TCTTATGGTGATGCTTATTCTGTACGTAAAAT
TGGTTATGAACTTTGGATAAAGAAAAGAGTTG
GGGATGGTTCAGTGCTTCGAACTATTCATGGA
AAAGAAATGTCCAAAATAGCCAGGAAGAAGAA
ACGAGCTGTCATTATGATGGTGACAGTGGTGG
CTCTCTTTGCTGTGTGCTGGGCACCATTCCAT
GTTGTCCATATGATGATTGAATACAGTAATTT
TGAAAAGGAATATGATGATGTCACAATCAAGA
TGATTTTTGATATCGTGCAAATTATTGGATTT
```

-continued

```
TCCAACTCCATCTGTAATCCCATTGTCTATGC
A-3'
```

Based on the above sequence, two sense oligonucleotide primer sets:

```
(SEQ. ID. NO.: 46; oligo 1)
5'-CTGCTTAGAAGAGTGGACCAG-3'
(SEQ. ID. NO.: 47; oligo 7)
5'-CTGTGCACGAGAAGATCTACAC-3'
```

and two antisense oligonucleotide primer sets:

```
(SEQ. ID. NO.: 48; oligo 3)
5'-CAAGGATGAAGGTGGTGTAGA-3'
(SEQ. ID. NO.: 49; oligo 4)
5'-GTGTAGATCTTCTGGTGCACAGG-3'
```

were used for 3'-and 5'-race PCR with a human brain Marathon-Ready™ cDNA (Clontech, Cat# 7400-1) as template, according to manufacture's instructions. DNA fragments generated by the RACE PCR were cloned into the pCRII-TOPO™ vector (Invitrogen) and sequenced using the SP6/T7 primers (Stratagene) and some internal primers. The 3' RACE product contained a poly(A) tail and a completed open reading frame ending at a TAA stop codon. The 5' RACE product contained an incomplete 5' end; i.e., the ATG initiation codon was not present.

Based on the new 5' sequence, oligo 3 and the following primer:

5'-GCAATGCAGGTCATAGTGAGC-3' (SEQ. ID. NO.: 50; oligo 5)

were used for the second round of 5' RACE PCR and the PCR products were analyzed as above. A third round of 5' RACE PCR was carried out utilizing antisense primers:

5'-TGGAGCATGGTGACGGGAATGCAGAAG-3' (SEQ. ID. NO.: 51; oligo 6) and

5'-GTGATGAGCAGGTCACTGAGCGCCAAG-3' (SEQ. ID. NO.: 52; oligo7).

The sequence of the 5' RACE PCR products revealed the presence of the initiation codon ATG, and further round of 5' RACE PCR did not generate any more 5' sequence. The completed 5' sequence was confirmed by RT-PCR using sense primer 5'-GCAATGCAGGCGCTTAACATFAC-3' (SEQ. ID. NO.: 53; oligo 8)

and oligo 4 as primers and sequence analysis of the 650 bp PCR product generated from human brain and heart cDNA templates (Clontech, Cat# 7404-1). The completed 3' sequence was confirmed by RT-PCR using oligo 2 and the following antisense primer:

5'-TTGGGTTACAATCTGAAGGGCA-3' (SEQ. ID. NO.: 54; oligo 9)

and sequence analysis of the 670 bp PCR product generated from human brain and heart cDNA templates. (Clontech, Cat# 7404-1).

d. hRUP5 (Seq. Id. Nos. 9 & 10)

The full length hRUP5 was cloned by RT-PCR using a sense primer upstream from ATG, the initiation codon (SEQ. ID. NO.: 55), and an antisense primer containing TCA as the stop codon (SEQ. ID. NO.: 56), which had the following sequences:

5'-ACTCCGTGTCCAGCAGGACTCTG-3' (SEQ. ID. NO.: 55)

5'-TGCGTGTTCCTGGACCCTCACGTG-3' (SEQ. ID. NO.: 56)

and human peripheral leukocyte cDNA (Clontech) as a template. Advantage cDNA polymerase (Clontech) was used for the amplification in a 50 ul reaction by the following cycle with step 2 through step 4 repeated 30 times: 94° C. for 30 sec: 94° for 15 sec; 69° for 40 sec; 72° C. for 3 min; and 72° C. from 6 min. A 1.4 kb PCR fragment was isolated and cloned with the pCRII-TOPO™ vector (Invitrogen) and completely sequenced using the T7 DNA Sequenase™ kit (Amsham). See, SEQ. ID. NO.: 9.

e. hRUP6 (Seq. Id. Nos. 11 & 12)

The full length hRUP6 was cloned by RT-PCR using primers:

(SEQ. ID. NO.: 57)
5'-CAGGCCTTGGATTTTAATGTCAGGGATGG-3' and (SEQ. ID. NO.: 58)
5'-GGAGAGTCAGCTCTGAAAGAATTCAGG-3';

and human thymus Marathon-Ready™ cDNA (Clontech) as a template. Advantage cDNA polymerase (Clontech, according to manufacturer's instructions) was used for the amplification in a 50 ul reaction by the following cycle: 94° C. for 30sec; 94° C. for 5 sec; 66° C. for 40sec; 72° C. for 2.5 sec and 72° C. for 7 min. Cycles 2 through 4 were repeated 30 times. A 1.3 Kb PCR fragment was isolated and cloned into the pCRII-TOPO™ vector (Invitrogen) and completely sequenced (see, SEQ. ID. NO.: 11) using the ABI Big Dye Terminator™ kit (P.E. Biosystem).

f. hRUP7 (Seq. Id. Nos. 13 & 14)

The full length RUP7 was cloned by RT-PCR using primers:

(SEQ. ID. NO.: 59; sense)
5'-TGATGTGATGCCAGATACTAATAGCAC-3'
and (SEQ. ID. NO.: 60; antisense)
5'-CCTGATTCATTTAGGTGAGATTGAGAC-3' and human peripheral leukocyte cDNA (Clontech) as a template. Advantage™ cDNA polymerase (Clontech) was used for the amplification in a 50 ul reaction by the following cycle with step 2 to step 4 repeated 30 times: 94° C. for 2 minutes; 94° C. for 15 seconds; 60° C. for 20 seconds; 72° C. for 2 minutes; 72° C. for 10 minutes. A 1.25 Kb PCR fragment was isolated and cloned into the pCRII-TOPO™ vector (Invitrogen) and completely sequenced using the ABI Big Dye Terminator™ kit (P.E. Biosystem). See, SEQ. ID. NO.: 13.

g. hARE-5 (Seq. Id. Nos. 5 & 6)

The full length hARE-5 was cloned by PCR using the hARE5 specific primers 5'-CAGCGCAGGGTGAAGCCTGAGAGC-3' SEQ. ID. NO.: 69 (sense, 5' of initiation codon ATG) and 5'-GGCACCTGCTGTGACCTGTGCAGG-3' SEQ. ID. NO.: 70 (antisense, 3' of stop codon TGA) and human genomic DNA as template. TaqPlus Precision™ DNA polymerase (Stratagene) was used for the amplification by the following cycle with step 2 to step 4 repeated 35 times: 96° C., 2 minutes; 96° C., 20 seconds; 58° C., 30 seconds; 72° C, 2 minutes; and 72° C., 10 minutes A 1.1 Kb PCR fragment of predicated size was isolated and cloned into the pCRII-TOPO™ vector (Invitrogen) and completely sequenced (SEQ. ID. NO.: 5) using the T7 DNA Sequenase™ kit (Amsham).

h. hARE-4 (Seq. Id. Nos.: 3 & 4)

The full length hARE-4 was cloned by PCR using the hARE-4 specific primers 5'-CTGGTGTGCTCCATGGCATCCC-3' SEQ.ID.NO.:67 (sense, 5' of initiation condon ATG) and 5'-GTAAGCCTCCCAGAACAGAGG-3' SEQ. ID. NO.: 68 (antisense, 3' of stop codon TGA) and human genomic DNA as template. Taq DNA polymerase (Stratagene) and 5% DMSO was used for the amplification by the following cycle with step 2 to step 3 repeated 35 times: 94° C., 3 minutes; 94° C., 30 seconds; 59° C., 2 minutes; 72° C., 10 minute A 1.12 Kb PCR fragment of predicated size was isolated and cloned into the pCRII-TOPO™ vector (Invitrogen) and completely sequenced (SEQ. ID. NO.: 3) using the T7 DNA Sequenase™ kit (Amsham).

i. hARE-3 (Seq. Id. Nos.: 1 & 2)

The full length hARE-3 was cloned by PCR using the hARE-3 specific primers 5'-gatcaagcttCCATCCTACTGAAACCATGGTC-3' SEQ.ID.NO65 (sense, lower case nucleotides represent Hind III overhang, ATG as initiation codon) and 5'-gatcagatctCAGTT CCAATATTCACACCACCGTC-3' SEQ. ID. NO.: 66 (antisense, lower case nucleotides represent Xba I overhang, TCA as stop codon) and human genomic DNA as template. TaqPlus Precision™ DNA polymerase (Stratagene) was used for the amplification by the following cycle with step 2 to step 4 repeated 35 times: 94° C., 3 minutes; 94° C., 1 minute; 55° C., 1 minute; 72° C., 2 minutes; 72° C., 10 minutes.

A 1.3 Kb PCR fragment of predicated size was isolated and digested with Hind III and Xba I, cloned into the pRC/CMV2 vector (Invitrogen) at the Hind III and Xba I sites and completely sequenced (SEQ. ID. NO.: 1) using the T7 DNA Sequenase™ kit (Amsham).

j. hRUP3 (Seq. Id. Nos.: 7 & 8)

The full length hRUP3 was cloned by PCR using the hRUP3 specific primers 5'-GTCCTGCCACTTCGAGACATGG-3' SEQ. ID.NO.:71 (sense, ATG as intiation codon) and 5'-GAAACTTCTCTCTGCCCTTACCGTC-3'

SEQ.ID.NO.:72 (antisense, 3' of stop codon TAA) and human genomic DNA as template. TaqPlus Precision™ DNA polymerase (Stratagene) was used for the amplification by the following cycle with step 2 to step 4 repeated 35 times: 94° C., 3 minutes; 94° C., 1 minute; 58° C., 1 minute; 72° C., 2 minutes: 72° C., 10 minutes A 1.0 Kb PCR fragment of predicated size was isolated and cloned into the pCRII-TOPO™ vector (Invitrogen) and completely sequenced (SEQ. ID. NO.: 7)using the T7 DNA sequenase kit (Amsham).

Example 2

Receptor Expression

Although a variety of cells are available to the art for the expression of proteins, it is most preferred that mammalian cells be utilized. The primary reason for this is predicated upon practicalities, i.e., utilization of, e.g., yeast cells for the expression of a GPCR, while possible, introduces into the protocol a non-mammalian cell which may not (indeed, in the case of yeast, does not) include the receptor-coupling, genetic-mechanism and secretary pathways that have evolved for mammalian systems—thus, results obtained in non-mammalian cells, while of potential use, are not as preferred as that obtained from mammalian cells. Of the mammalian cells, COS-7, 293 and 293T cells are particularly preferred, although the specific mammalian cell utilized can be predicated upon the particular needs of the artisan. The general procedure for expression of the disclosed GPCRs is as follows.

On day one, $1\times10^7$293T cells per 150 mm plate were plated out. On day two, two reaction tubes will be prepared (the proportions to follow for each tube are per plate): tube A will be prepared by mixing 20 μg DNA (e.g., pCMV vector, pCMV vector with receptor cDNA, etc.) in 1.2 ml serum free DMEM (Irvine Scientific, Irvine, Calif.); tube B will be prepared by mixing 120 μl lipofectamine (Gibco BRL) in 1.2 ml serum free DMEM. Tubes A and B are admixed by inversions (several times), followed by incubation at room temperature for 30–45 min. The admixture can be referred to as the "transfection mixture". Plated 293T cells are washed with 1×PBS, followed by addition of 10 ml serum free DMEM. 2.4 ml of the transfection mixture will then be added to the cells, followed by incubation for 4 hrs at 37° C./5% $CO_2$. The transfection mixture was then be removed by aspiration, followed by the addition of 25 ml of DMEM/10% Fetal Bovine Serum. Cells will then be incubated at 37° C./5% $CO_2$. After 72hr incubation, cells can then be harvested and utilized for analysis.

Example 3

Tissue Distribution of the Disclosed Human GPCRs

Several approaches can be used for determination of the tissue distribution of the GPCRs disclosed herein.

1. Dot-Blot Analysis

Figure 2B:
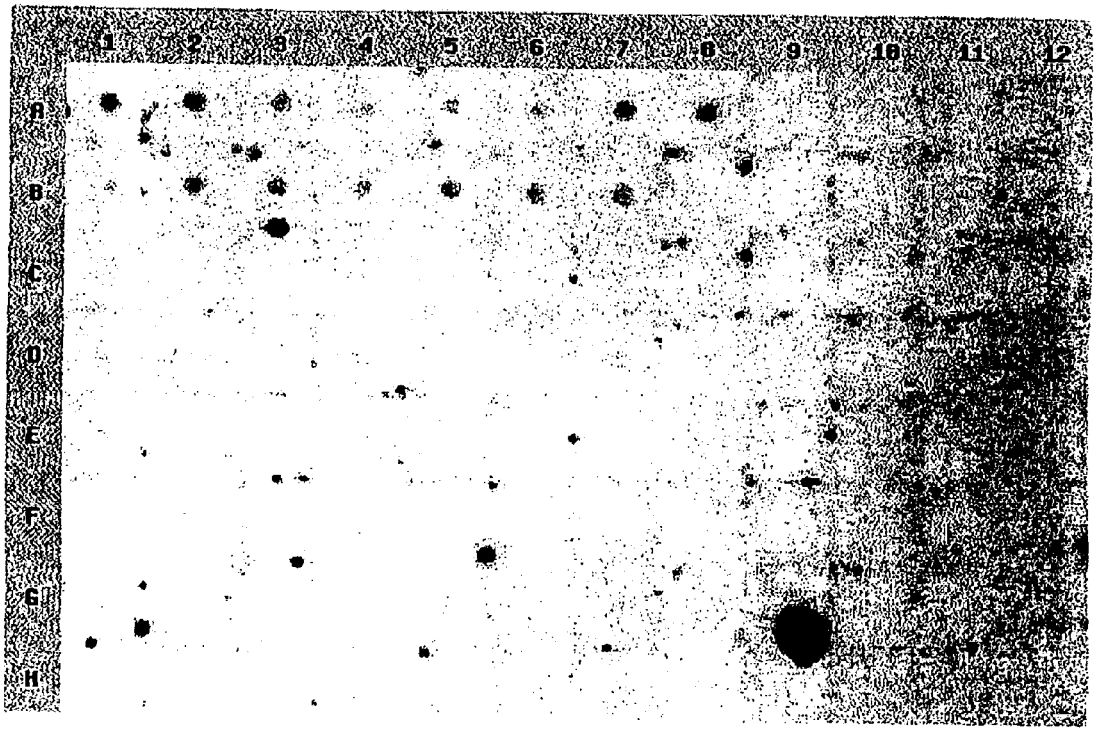

Using a commercially available human-tissue dot-blot format, endogenous orphan GPCRs were probed for a determination of the areas where such receptors are localized. cDNA fragments from the GPCRs of Example 1 (radiolabelled) were (or can be) used as the probe: radiolabeled probe was (or can be) generated using the complete receptor cDNA (excised from the vector) using a Prime-It II™ Random Primer Labeling Kit (Stratagene, #300385), according to manufacturer's instructions. A human RNA Master Blot™ (Clontech, #7770-1) was hybridized with the endogenous human GPCR radiolabeled probe and washed under stringent conditions according manufacturer's instructions. The blot was exposed to Kodak BioMax™ Autoradiography film overnight at −80° C. Results are summarized for several receptors in Table B and C (see FIGS. 1A and 1B for a grid identifying the various tissues and their locations, respectively). Exemplary dot-blots are provided in FIGS. 2A and 2B for results derived using hCHN3 and hCHN8, respectively.

TABLE B

| ORPHAN GPCR | Tissue Distribution (highest levels, relative to other tissues in the dot-blot |
|---|---|
| hGPCR27 | Fetal brain, Putamen, Pituitary gland, Caudate nucleus |
| hARE-1 | Spleen, Peripheral leukocytes, Fetal spleen |
| hPPR1 | Pituitary gland, Heart, salivary gland, Small intestine, Testis |
| hRUP3 | Pancreas |
| hCHN3 | Fetal brain, Putamen, Occipital cortex |
| hCHN9 | Pancreas, Small intestine, Liver |
| hCHN10 | Kidney, Thyroid |

TABLE C

| ORPHAN GPCR | Tissue Distribution (highest levels, relative to other tissues in the dot-blot |
|---|---|
| hARE-3 | Cerebellum left, Cerebellum right, Testis, Accumbens |
| hGPCR3 | Corpus collusum, Caudate nucleus, Liver, Heart, Inter-Ventricular Septum |
| hARE-2 | Cerebellum left, Cerebellum right, Substantia |
| hCHN8 | Cerebellum left, Cerebellum right, Kidney, Lung |

To ascertain the tissue distribution of hRUP3 mRNA, RT-PCR was performed using hRUP3-specific primers and human multiple tissue cDNA panels (MTC, Clontech) as templates. Taq DNA polymerase (Stratagene) was utilized for the PCR reaction, using the following reaction cycles in a 40 ul reaction: 94° C. for 2 min; 94° C. for 15 sec; 55° C. for 30 sec; 72° C. for 1 min: 72° C., for 10 min. Primers were as follows:

```
                    (SEQ. ID. NO.: 61; sense)
5'-GACAGGTACCTTGCCATCAAG-3'

                    (SEQ. ID. NO.: 62; antisense)
5'-CTGCACAATGCCAGTGATAAGG-3'.
```

Figure 3:
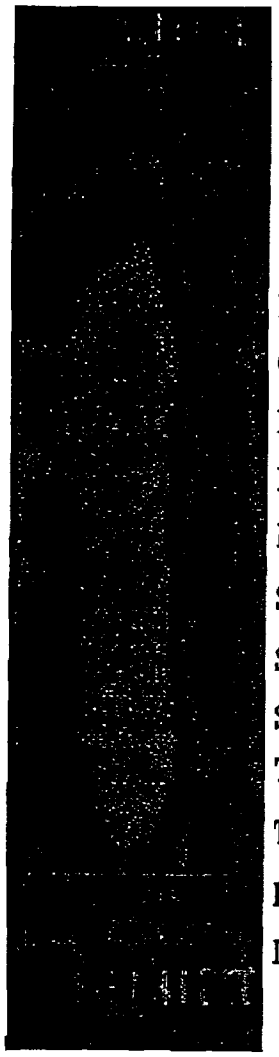
FIG. 3 provides a reproduction of the results of RT-PCR analysis of hRUP3.

20 ul of the reaction was loaded onto a 1% agarose gel: results are set forth in FIG. 3.

As is supported by the data of FIG. 3, of the 16 human tissues in the cDNA panel utilized (brain, colon, heart, kidney, lung, ovary, pancreas, placenta, prostate, skeleton, small intestine, spleen, testis, thymus leukocyte, and liver) a single hRUP3 band is evident only from the pancreas. Additional comparative analysis of the protein sequence of hRUP3 with other GPCRs suggest that hRUP3 is related to GPCRs having small molecule endogenous ligand such that it is predicted that the endogenous ligand for hRUP3 is a small molecule.

b. hRUP4

RT-PCR was performed using hRUP4 oligo's 8 and 4 as primers and the human multiple tissue cDNA panels (MTC, Clontech) as templates. Taq DNA polymerase (Stratagene) was used for the amplification in a 40 ul reaction by the following cycles: 94° C. for 30 seconds, 94° C. for 10 seconds, 55° C. for 30 seconds, 72° C. for 2 minutes, and 72° C. for 5 minutes with cycles 2 through 4 repeated 30 times.

Figure 4:
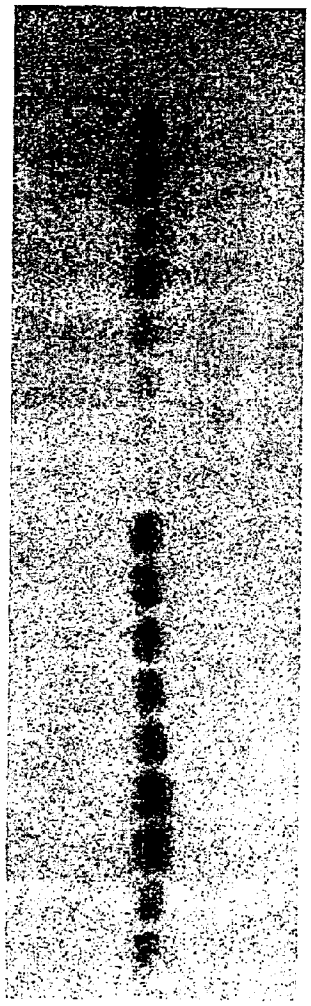
FIG. 4 provides a reproduction of the results of RT-PCR analysis of hRUP4.

20 ul of the reaction were loaded on a 1% agarose gel to analyze the RT-PCR products, and hRUP4 mRNA was found expressed in many human tissues, with the strongest expression in heart and kidney. (see, FIG. 4). To confirm the authenticity of the PCR fragments, a 300 bp fragment derived from the 5' end of hRUP4 was used as a probe for the Southern Blot analysis. The probe was labeled with $^{32}$P-dCTP using the Prime-It II™ Random Primer Labeling Kit (Stratagene) and purified using the ProbeQuant™ G-50 micro columns (Amersham). Hybridization was done overnight at 42° C. following a 12 hr pre-hybridization. The blot was finally washed at 65° C. with 0.1×SSC. The Southern blot did confirm the PCR fragments as hRUP4.

c. hRUP5

RT-PCR was performed using the following hRUP5 specific primers:

```
                    (SEQ. ID. NO.: 63; sense)
5'-CTGACTTCTTGTTCCTGGCAGCAGCGG-3'

                    (SEQ. ID. NO.: 64; antisense)
5'-AGACCAGCCAGGGCACGCTGAAGAGTG-3'
```

and the human multiple tissue cDNA panels (MTC, Clontech) as templates. Taq DNA polymerase (Stratagene) was used for the amplification in a 40 ul reaction by the following cycles: 94° C. for 30 sec, 94° C. for 10 sec, 62° C. for 1.5 min, 72° C. for 5 min, and with cycles 2 through 3 repeated 30 times. 20 ul of the reaction were loaded on a 1.5% agarose gel to analyze the RT-PCR products, and hRUP5 mRNA was found expressed only in the peripheral blood leukocytes (data not shown).

d. hRUP6

RT-PCR was applied to confirm the expression and to determine the tissue distribution of hRUP6. Oligonucleotides used, based on an alignment of AC005871 and GPR66 segments, had the following sequences:

(SEQ. ID. NO.: 73; sense)
5'-CCAACACCAGCATCCATGGCATCAAG-3', (SEQ. ID. NO.: 74; antisense)
5'-GGAGAGTCAGCTCTGAAAGAATTCAGG-3' and the human multiple tissue cDNA panels (MTC, Clontech) were used as templates. PCR was performed using TaqPlus Precision™ polymerase (Stratagene; manufacturing instructions will be followed) in a 40 ul reaction by the following cycles: 94° C. for 30 sec; 94° C. 5 sec; 66° C. for 40 sec, 72° C. for 2.5 min, and 72° C. for 7 min. Cycles 2 through 4 were repeated 30 times.

Figure 5:
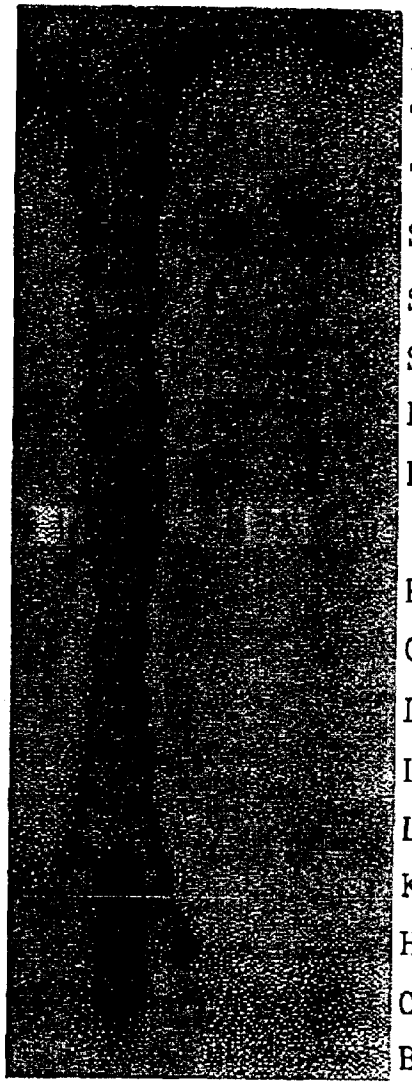
FIG. 5 provides a reproduction of the results of RT-PCR analysis of hRUP6.
Figure 6:
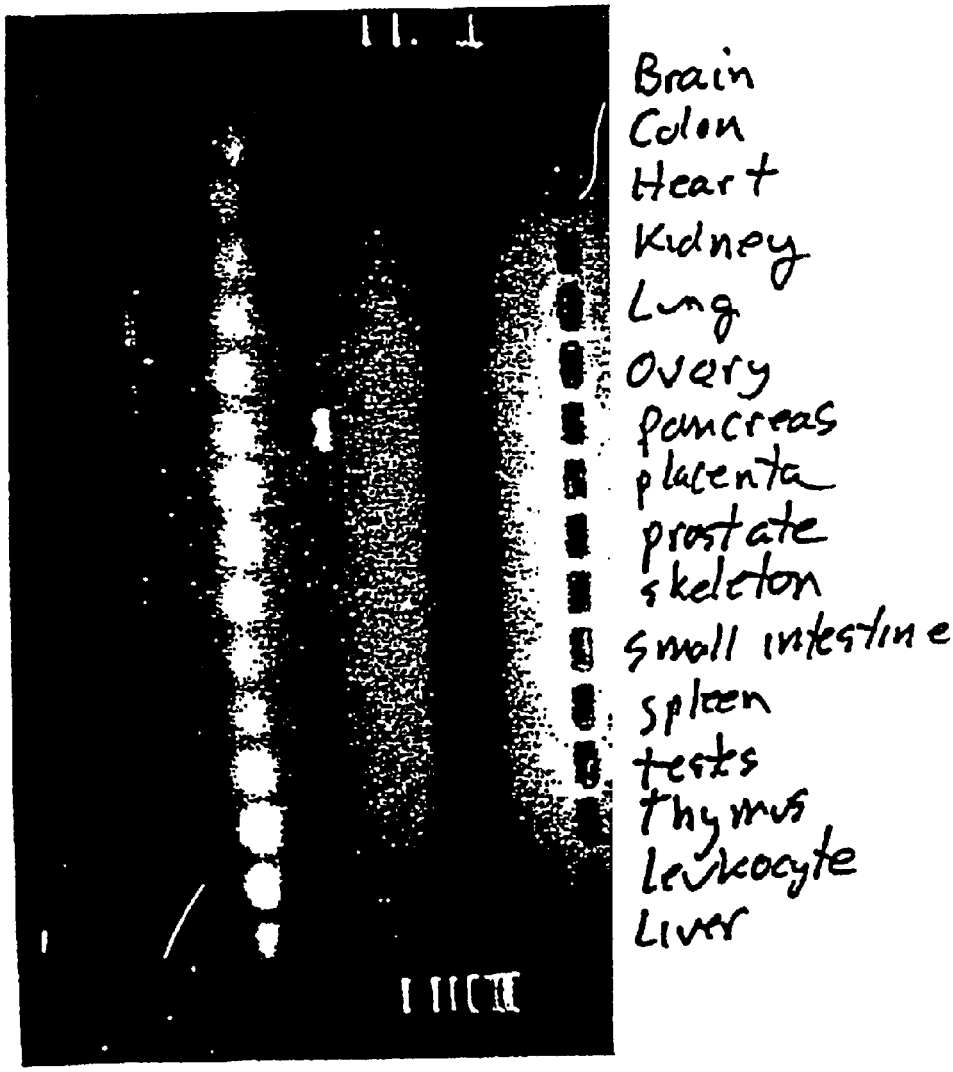
FIG. 6 is a reproduction of a photograph of the results of the tissue distribution of RUP3 using multiple tissue (human) cDNA. Based upon these tissues, the data support the position that RUP3 is expressed only in the pancreas.

20 ul of the reaction were loaded on a 1.2% agarose gel to analyze the RT-PCR products, and a specific 760 bp DNA fragment representing hRUP6 was expressed predominantly in the thymus and with less expression in the heart, kidney, lung, prostate small intestine and testis. (see, FIG. 5).

It is intended that each of the patents, applications, and printed publications mentioned in this patent document be hereby incorporated by reference in their entirety.

As those skilled in the art will appreciate, numerous changes and modifications may be made to the preferred embodiments of the invention without departing from the spirit of the invention. It is intended that all such variations fall within the scope of the invention and the claims that follow.

Although a variety of Vectors are available to those in the art, for purposes of utilization for both endogenous and non-endogenous human GPCRs, it is most preferred that the Vector utilized be pCMV. This vector was deposited with the American Type Culture Collection (ATCC) on Oct. 13, 1998 (10801 University Blvd., Manassas, Va. 20110-2209 USA) under the provisions of the Budapest Treaty for the International Recognition of the Deposit of Microorganisms for the Purpose of Patent Procedure. The DNA was tested by the ATCC and determined to be. The ATCC has assigned the following deposit number to pCMV: ATCC #203351.

SEQUENCE LISTING

<160> NUMBER OF SEQ ID NOS: 74

<210> SEQ ID NO 1
<211> LENGTH: 1260
<212> TYPE: DNA
<213> ORGANISM: Homo sapiens

<400> SEQUENCE: 1 atggtcttct cggcagtgtt gactgcgttc cataccggga catccaacac aacatttgtc 60 gtgtatgaaa acacctacat gaatattaca ctccctccac cattccagca tcctgacctc 120 agtccattgc ttagatatag ttttgaaacc atggctccca ctggtttgag ttccttgacc 180 gtgaatagta cagctgtgcc cacaacacca gcagcattta agagcctaaa cttgcctctt 240 cagatcaccc tttctgctat aatgatattc attctgtttg tgtcttttct tgggaacttg 300 gttgtttgcc tcatggttta ccaaaaagct gccatgaggt ctgcaattaa catcctcctt 360 gccagcctag cttttgcaga catgttgctt gcagtgctga acatgccctt tgccctggta 420 actattctta ctacccgatg gatttttggg aaattcttct gtagggtatc tgctatgttt 480 ttctggttat ttgtgataga aggagtagcc atcctgctca tcattagcat agataggttc 540 cttattatag tccagaggca ggataagcta aacccatata gagctaaggt tctgattgca 600 gtttcttggg caacttcctt ttgtgtagct tttcctttag ccgtaggaaa ccccgacctg 660 cagatacctt cccgagctcc ccagtgtgtg tttgggtaca caaccaatcc aggctaccag 720 gcttatgtga ttttgatttc tctcatttct ttcttcatac ccttcctggt aatactgtac 780 tcatttatgg gcatactcaa cacccttcgg cacaatgcct tgaggatcca tagctaccct 840 gaaggtatat gcctcagcca ggccagcaaa ctgggtctca tgagtctgca gagacctttc 900 cagatgagca ttgacatggg ctttaaaaca cgtgccttca ccactatttt gattctcttt 960 gctgtcttca ttgtctgctg ggccccattc accacttaca gccttgtggc aacattcagt 1020 aagcactttt actatcagca caactttttt gagattagca cctggctact gtggctctgc 1080 tacctcaagt ctgcattgaa tccgctgatc tactactgga ggattaagaa attccatgat 1140 gcttgcctgg acatgatgcc taagtccttc aagtttttgc cgcagctccc tggtcacaca 1200 aagcgacgga tacgtcctag tgctgtctat gtgtgtgggg aacatcggac ggtggtgtga 1260

-continued

<210> SEQ ID NO 2
<211> LENGTH: 419
<212> TYPE: PRT
<213> ORGANISM: Homo sapiens

<400> SEQUENCE: 2

Met Val Phe Ser Ala Val Leu Thr Ala Phe His Thr Gly Thr Ser Asn
1 5 10 15

Thr Thr Phe Val Val Tyr Glu Asn Thr Tyr Met Asn Ile Thr Leu Pro
20 25 30

Pro Pro Phe Gln His Pro Asp Leu Ser Pro Leu Leu Arg Tyr Ser Phe
35 40 45

Glu Thr Met Ala Pro Thr Gly Leu Ser Ser Leu Thr Val Asn Ser Thr
50 55 60

Ala Val Pro Thr Thr Pro Ala Ala Phe Lys Ser Leu Asn Leu Pro Leu
65 70 75 80

Gln Ile Thr Leu Ser Ala Ile Met Ile Phe Ile Leu Phe Val Ser Phe
85 90 95

Leu Gly Asn Leu Val Val Cys Leu Met Val Tyr Gln Lys Ala Ala Met
100 105 110

Arg Ser Ala Ile Asn Ile Leu Leu Ala Ser Leu Ala Phe Ala Asp Met
115 120 125

Leu Leu Ala Val Leu Asn Met Pro Phe Ala Leu Val Thr Ile Leu Thr
130 135 140

Thr Arg Trp Ile Phe Gly Lys Phe Phe Cys Arg Val Ser Ala Met Phe
145 150 155 160

Phe Trp Leu Phe Val Ile Glu Gly Val Ala Ile Leu Leu Ile Ile Ser
165 170 175

Ile Asp Arg Phe Leu Ile Ile Val Gln Arg Gln Asp Lys Leu Asn Pro
180 185 190

Tyr Arg Ala Lys Val Leu Ile Ala Val Ser Trp Ala Thr Ser Phe Cys
195 200 205

Val Ala Phe Pro Leu Ala Val Gly Asn Pro Asp Leu Gln Ile Pro Ser
210 215 220

Arg Ala Pro Gln Cys Val Phe Gly Tyr Thr Thr Asn Pro Gly Tyr Gln
225 230 235 240

Ala Tyr Val Ile Leu Ile Ser Leu Ile Ser Phe Phe Ile Pro Phe Leu
245 250 255

Val Ile Leu Tyr Ser Phe Met Gly Ile Leu Asn Thr Leu Arg His Asn
260 265 270

Ala Leu Arg Ile His Ser Tyr Pro Glu Gly Ile Cys Leu Ser Gln Ala
275 280 285

Ser Lys Leu Gly Leu Met Ser Leu Gln Arg Pro Phe Gln Met Ser Ile
290 295 300

Asp Met Gly Phe Lys Thr Arg Ala Phe Thr Thr Ile Leu Ile Leu Phe
305 310 315 320

Ala Val Phe Ile Val Cys Trp Ala Pro Phe Thr Thr Tyr Ser Leu Val
325 330 335

Ala Thr Phe Ser Lys His Phe Tyr Tyr Gln His Asn Phe Phe Glu Ile
340 345 350

Ser Thr Trp Leu Leu Trp Leu Cys Tyr Leu Lys Ser Ala Leu Asn Pro
355 360 365

Leu Ile Tyr Tyr Trp Arg Ile Lys Lys Phe His Asp Ala Cys Leu Asp
370 375 380

```
Met Met Pro Lys Ser Phe Lys Phe Leu Pro Gln Leu Pro Gly His Thr
385                 390                 395                 400

Lys Arg Arg Ile Arg Pro Ser Ala Val Tyr Val Cys Gly Glu His Arg
                405                 410                 415

Thr Val Val


<210> SEQ ID NO 3
<211> LENGTH: 1119
<212> TYPE: DNA
<213> ORGANISM: Homo sapiens

<400> SEQUENCE: 3

atgttagcca acagctcctc aaccaacagt tctgttctcc cgtgtcctga ctaccgacct     60

acccaccgcc tgcacttggt ggtctacagc ttggtgctgg ctgccgggct ccccctcaac    120

gcgctagccc tctgggtctt cctgcgcgcg ctgcgcgtgc actcggtggt gagcgtgtac    180

atgtgtaacc tggcggccag cgacctgctc ttcaccctct cgctgcccgt tcgtctctcc    240

tactacgcac tgcaccactg gcccttcccc gacctcctgt gccagacgac gggcgccatc    300

ttccagatga acatgtacgg cagctgcatc ttcctgatgc tcatcaacgt ggaccgctac    360

gccgccatcg tgcacccgct gcgactgcgc cacctgcggc ggccccgcgt ggcgcggctg    420

ctctgcctgg gcgtgtgggc gctcatcctg gtgtttgccg tgcccgccgc ccgcgtgcac    480

aggccctcgc gttgccgcta ccgggacctc gaggtgcgcc tatgcttcga gagcttcagc    540

gacgagctgt ggaaaggcag gctgctgccc ctcgtgctgc tggccgaggc gctgggcttc    600

ctgctgcccc tggcggcggt ggtctactcg tcgggccgag tcttctggac gctggcgcgc    660

cccgacgcca cgcagagcca gcggcggcgg aagaccgtgc gcctcctgct ggctaacctc    720

gtcatcttcc tgctgtgctt cgtgccctac aacagcacgc tggcggtcta cgggctgctg    780

cggagcaagc tggtggcggc cagcgtgcct gcccgcgatc gcgtgcgcgg ggtgctgatg    840

gtgatggtgc tgctggccgg cgccaactgc gtgctggacc cgctggtgta ctactttagc    900

gccgagggct tccgcaacac cctgcgcggc ctgggcactc cgcaccgggc caggacctcg    960

gccaccaacg ggacgcgggc ggcgctcgcg caatccgaaa ggtccgccgt caccaccgac   1020

gccaccaggc cggatgccgc cagtcagggg ctgctccgac cctccgactc ccactctctg   1080

tcttccttca cacagtgtcc ccaggattcc gccctctga                          1119


<210> SEQ ID NO 4
<211> LENGTH: 372
<212> TYPE: PRT
<213> ORGANISM: Homo sapiens

<400> SEQUENCE: 4

Met Leu Ala Asn Ser Ser Ser Thr Asn Ser Ser Val Leu Pro Cys Pro
  1               5                  10                  15

Asp Tyr Arg Pro Thr His Arg Leu His Leu Val Val Tyr Ser Leu Val
             20                  25                  30

Leu Ala Ala Gly Leu Pro Leu Asn Ala Leu Ala Leu Trp Val Phe Leu
         35                  40                  45

Arg Ala Leu Arg Val His Ser Val Val Ser Val Tyr Met Cys Asn Leu
     50                  55                  60

Ala Ala Ser Asp Leu Leu Phe Thr Leu Ser Leu Pro Val Arg Leu Ser
 65                  70                  75                  80

Tyr Tyr Ala Leu His His Trp Pro Phe Pro Asp Leu Leu Cys Gln Thr
```

-continued

```
                85                  90                  95

Thr Gly Ala Ile Phe Gln Met Asn Met Tyr Gly Ser Cys Ile Phe Leu
            100                 105                 110

Met Leu Ile Asn Val Asp Arg Tyr Ala Ala Ile Val His Pro Leu Arg
        115                 120                 125

Leu Arg His Leu Arg Arg Pro Arg Val Ala Arg Leu Leu Cys Leu Gly
    130                 135                 140

Val Trp Ala Leu Ile Leu Val Phe Ala Val Pro Ala Ala Arg Val His
145                 150                 155                 160

Arg Pro Ser Arg Cys Arg Tyr Arg Asp Leu Glu Val Arg Leu Cys Phe
                165                 170                 175

Glu Ser Phe Ser Asp Glu Leu Trp Lys Gly Arg Leu Leu Pro Leu Val
            180                 185                 190

Leu Leu Ala Glu Ala Leu Gly Phe Leu Leu Pro Leu Ala Ala Val Val
        195                 200                 205

Tyr Ser Ser Gly Arg Val Phe Trp Thr Leu Ala Arg Pro Asp Ala Thr
    210                 215                 220

Gln Ser Gln Arg Arg Arg Lys Thr Val Arg Leu Leu Leu Ala Asn Leu
225                 230                 235                 240

Val Ile Phe Leu Leu Cys Phe Val Pro Tyr Asn Ser Thr Leu Ala Val
                245                 250                 255

Tyr Gly Leu Leu Arg Ser Lys Leu Val Ala Ala Ser Val Pro Ala Arg
            260                 265                 270

Asp Arg Val Arg Gly Val Leu Met Val Met Val Leu Leu Ala Gly Ala
        275                 280                 285

Asn Cys Val Leu Asp Pro Leu Val Tyr Tyr Phe Ser Ala Glu Gly Phe
    290                 295                 300

Arg Asn Thr Leu Arg Gly Leu Gly Thr Pro His Arg Ala Arg Thr Ser
305                 310                 315                 320

Ala Thr Asn Gly Thr Arg Ala Ala Leu Ala Gln Ser Glu Arg Ser Ala
                325                 330                 335

Val Thr Thr Asp Ala Thr Arg Pro Asp Ala Ala Ser Gln Gly Leu Leu
            340                 345                 350

Arg Pro Ser Asp Ser His Ser Leu Ser Ser Phe Thr Gln Cys Pro Gln
        355                 360                 365

Asp Ser Ala Leu
    370


<210> SEQ ID NO 5
<211> LENGTH: 1107
<212> TYPE: DNA
<213> ORGANISM: Homo sapiens

<400> SEQUENCE: 5

atggccaact ccacagggct gaacgcctca gaagtcgcag gctcgttggg gttgatcctg      60

gcagctgtcg tggaggtggg ggcactgctg ggcaacggcg cgctgctggt cgtggtgctg     120

cgcacgccgg gactgcgcga cgcgctctac ctggcgcacc tgtgcgtcgt ggacctgctg     180

gcggccgcct ccatcatgcc gctgggcctg ctggccgcac cgccgcccgg gctgggccgc     240

gtgcgcctgg gccccgcgcc atgccgcgcc gctcgcttcc tctccgccgc tctgctgccg     300

gcctgcacgc tcggggtggc cgcacttggc ctggcacgct accgcctcat cgtgcacccg     360

ctgcggccag gctcgcggcc gccgcctgtg ctcgtgctca ccgccgtgtg ggccgcggcg     420

ggactgctgg gcgcgctctc cctgctcggc ccgccgcccg caccgccccc tgctcctgct     480
```

-continued

```
cgctgctcgg tcctggctgg gggcctcggg cccttccggc cgctctgggc cctgctggcc    540

ttcgcgctgc ccgccctcct gctgctcggc gcctacggcg gcatcttcgt ggtggcgcgt    600

cgcgctgccc tgaggccccc acggccggcg cgcgggtccc gactccgctc ggactctctg    660

gatagccgcc tttccatctt gccgccgctc cggcctcgcc tgcccggggg caaggcggcc    720

ctggccccag cgctggccgt gggccaattt gcagcctgct ggctgcctta tggctgcgcg    780

tgcctggcgc ccgcagcgcg ggccgcggaa gccgaagcgg ctgtcacctg ggtcgcctac    840

tcggccttcg cggctcaccc cttcctgtac gggctgctgc agcgccccgt gcgcttggca    900

ctgggccgcc tctctcgccg tgcactgcct ggacctgtgc gggcctgcac tccgcaagcc    960

tggcacccgc gggcactctt gcaatgcctc cagagacccc cagagggccc tgccgtaggc   1020

ccttctgagg ctccagaaca gacccccgag ttggcaggag ggcggagccc cgcataccag   1080

gggccacctg agagttctct ctcctga                                       1107
```

<210> SEQ ID NO 6
<211> LENGTH: 368
<212> TYPE: PRT
<213> ORGANISM: Homo sapiens

<400> SEQUENCE: 6

```
Met Ala Asn Ser Thr Gly Leu Asn Ala Ser Glu Val Ala Gly Ser Leu
  1               5                  10                  15

Gly Leu Ile Leu Ala Ala Val Val Glu Val Gly Ala Leu Leu Gly Asn
             20                  25                  30

Gly Ala Leu Leu Val Val Val Leu Arg Thr Pro Gly Leu Arg Asp Ala
         35                  40                  45

Leu Tyr Leu Ala His Leu Cys Val Val Asp Leu Leu Ala Ala Ala Ser
     50                  55                  60

Ile Met Pro Leu Gly Leu Leu Ala Ala Pro Pro Pro Gly Leu Gly Arg
 65                  70                  75                  80

Val Arg Leu Gly Pro Ala Pro Cys Arg Ala Ala Arg Phe Leu Ser Ala
                 85                  90                  95

Ala Leu Leu Pro Ala Cys Thr Leu Gly Val Ala Ala Leu Gly Leu Ala
            100                 105                 110

Arg Tyr Arg Leu Ile Val His Pro Leu Arg Pro Gly Ser Arg Pro Pro
        115                 120                 125

Pro Val Leu Val Leu Thr Ala Val Trp Ala Ala Ala Gly Leu Leu Gly
    130                 135                 140

Ala Leu Ser Leu Leu Gly Pro Pro Pro Ala Pro Pro Pro Ala Pro Ala
145                 150                 155                 160

Arg Cys Ser Val Leu Ala Gly Gly Leu Gly Pro Phe Arg Pro Leu Trp
                165                 170                 175

Ala Leu Leu Ala Phe Ala Leu Pro Ala Leu Leu Leu Leu Gly Ala Tyr
            180                 185                 190

Gly Gly Ile Phe Val Val Ala Arg Arg Ala Ala Leu Arg Pro Pro Arg
        195                 200                 205

Pro Ala Arg Gly Ser Arg Leu Arg Ser Asp Ser Leu Asp Ser Arg Leu
    210                 215                 220

Ser Ile Leu Pro Pro Leu Arg Pro Arg Leu Pro Gly Gly Lys Ala Ala
225                 230                 235                 240

Leu Ala Pro Ala Leu Ala Val Gly Gln Phe Ala Ala Cys Trp Leu Pro
                245                 250                 255
```

-continued

```
Tyr Gly Cys Ala Cys Leu Ala Pro Ala Ala Arg Ala Ala Glu Ala Glu
            260                 265                 270

Ala Ala Val Thr Trp Val Ala Tyr Ser Ala Phe Ala Ala His Pro Phe
        275                 280                 285

Leu Tyr Gly Leu Leu Gln Arg Pro Val Arg Leu Ala Leu Gly Arg Leu
    290                 295                 300

Ser Arg Arg Ala Leu Pro Gly Pro Val Arg Ala Cys Thr Pro Gln Ala
305                 310                 315                 320

Trp His Pro Arg Ala Leu Leu Gln Cys Leu Gln Arg Pro Pro Glu Gly
                325                 330                 335

Pro Ala Val Gly Pro Ser Glu Ala Pro Glu Gln Thr Pro Glu Leu Ala
            340                 345                 350

Gly Gly Arg Ser Pro Ala Tyr Gln Gly Pro Pro Glu Ser Ser Leu Ser
        355                 360                 365


<210> SEQ ID NO 7
<211> LENGTH: 1008
<212> TYPE: DNA
<213> ORGANISM: Homo sapiens

<400> SEQUENCE: 7

atggaatcat ctttctcatt tggagtgatc cttgctgtcc tggcctccct catcattgct     60

actaacacac tagtggctgt ggctgtgctg ctgttgatcc acaagaatga tggtgtcagt    120

ctctgcttca ccttgaatct ggctgtggct gacaccttga ttggtgtggc catctctggc    180

ctactcacag accagctctc cagcccttct cggcccacac agaagaccct gtgcagcctg    240

cggatggcat ttgtcacttc ctccgcagct gcctctgtcc tcacggtcat gctgatcacc    300

tttgacaggt accttgccat caagcagccc ttccgctact tgaagatcat gagtgggttc    360

gtggccgggg cctgcattgc cgggctgtgg ttagtgtctt acctcattgg cttcctccca    420

ctcggaatcc ccatgttcca gcagactgcc tacaaagggc agtgcagctt ctttgctgta    480

tttcaccctc acttcgtgct gaccctctcc tgcgttggct tcttcccagc catgctcctc    540

tttgtcttct tctactgcga catgctcaag attgcctcca tgcacagcca gcagattcga    600

aagatggaac atgcaggagc catggctgga ggttatcgat ccccacggac tcccagcgac    660

ttcaaagctc tccgtactgt gtctgttctc attgggagct ttgctctatc ctggaccccc    720

ttccttatca ctggcattgt gcaggtggcc tgccaggagt gtcacctcta cctagtgctg    780

gaacggtacc tgtggctgct cggcgtgggc aactccctgc tcaacccact catctatgcc    840

tattggcaga aggaggtgcg actgcagctc taccacatgg ccctaggagt gaagaaggtg    900

ctcacctcat tcctcctctt tctctcggcc aggaattgtg gcccagagag gcccagggaa    960

agttcctgtc acatcgtcac tatctccagc tcagagtttg atggctaa                1008


<210> SEQ ID NO 8
<211> LENGTH: 335
<212> TYPE: PRT
<213> ORGANISM: Homo sapiens

<400> SEQUENCE: 8

Met Glu Ser Ser Phe Ser Phe Gly Val Ile Leu Ala Val Leu Ala Ser
  1               5                  10                  15

Leu Ile Ile Ala Thr Asn Thr Leu Val Ala Val Ala Val Leu Leu Leu
            20                  25                  30

Ile His Lys Asn Asp Gly Val Ser Leu Cys Phe Thr Leu Asn Leu Ala
        35                  40                  45
```

-continued

```
Val Ala Asp Thr Leu Ile Gly Val Ala Ile Ser Gly Leu Leu Thr Asp
     50                  55                  60

Gln Leu Ser Ser Pro Ser Arg Pro Thr Gln Lys Thr Leu Cys Ser Leu
 65                  70                  75                  80

Arg Met Ala Phe Val Thr Ser Ser Ala Ala Ala Ser Val Leu Thr Val
                 85                  90                  95

Met Leu Ile Thr Phe Asp Arg Tyr Leu Ala Ile Lys Gln Pro Phe Arg
            100                 105                 110

Tyr Leu Lys Ile Met Ser Gly Phe Val Ala Gly Ala Cys Ile Ala Gly
        115                 120                 125

Leu Trp Leu Val Ser Tyr Leu Ile Gly Phe Leu Pro Leu Gly Ile Pro
    130                 135                 140

Met Phe Gln Gln Thr Ala Tyr Lys Gly Gln Cys Ser Phe Phe Ala Val
145                 150                 155                 160

Phe His Pro His Phe Val Leu Thr Leu Ser Cys Val Gly Phe Phe Pro
                165                 170                 175

Ala Met Leu Leu Phe Val Phe Phe Tyr Cys Asp Met Leu Lys Ile Ala
            180                 185                 190

Ser Met His Ser Gln Gln Ile Arg Lys Met Glu His Ala Gly Ala Met
        195                 200                 205

Ala Gly Gly Tyr Arg Ser Pro Arg Thr Pro Ser Asp Phe Lys Ala Leu
    210                 215                 220

Arg Thr Val Ser Val Leu Ile Gly Ser Phe Ala Leu Ser Trp Thr Pro
225                 230                 235                 240

Phe Leu Ile Thr Gly Ile Val Gln Val Ala Cys Gln Glu Cys His Leu
                245                 250                 255

Tyr Leu Val Leu Glu Arg Tyr Leu Trp Leu Leu Gly Val Gly Asn Ser
            260                 265                 270

Leu Leu Asn Pro Leu Ile Tyr Ala Tyr Trp Gln Lys Glu Val Arg Leu
        275                 280                 285

Gln Leu Tyr His Met Ala Leu Gly Val Lys Lys Val Leu Thr Ser Phe
    290                 295                 300

Leu Leu Phe Leu Ser Ala Arg Asn Cys Gly Pro Glu Arg Pro Arg Glu
305                 310                 315                 320

Ser Ser Cys His Ile Val Thr Ile Ser Ser Ser Glu Phe Asp Gly
                325                 330                 335


<210> SEQ ID NO 9
<211> LENGTH: 1413
<212> TYPE: DNA
<213> ORGANISM: Homo sapiens

<400> SEQUENCE: 9

atggacacta ccatggaagc tgacctgggt gccactggcc acaggccccg cacagagctt      60

gatgatgagg actcctaccc ccaaggtggc tgggacacgg tcttcctggt ggccctgctg     120

ctccttgggc tgccagccaa tgggttgatg gcgtggctgg ccggctccca ggcccggcat     180

ggagctggca cgcgtctggc gctgctcctg ctcagcctgg ccctctctga cttcttgttc     240

ctggcagcag cggccttcca gatcctagag atccggcatg ggggacactg gccgctgggg     300

acagctgcct gccgcttcta ctacttccta tggggcgtgt cctactcctc cggcctcttc     360

ctgctggccg ccctcagcct cgaccgctgc ctgctggcgc tgtgcccaca ctggtaccct     420

gggcaccgcc cagtccgcct gcccctctgg gtctgcgccg gtgtctgggt gctggccaca     480
```

-continued

```
ctcttcagcg tgccctggct ggtcttcccc gaggctgccg tctggtggta cgacctggtc    540

atctgcctgg acttctggga cagcgaggag ctgtcgctga ggatgctgga ggtcctgggg    600

ggcttcctgc ctttcctcct gctgctcgtc tgccacgtgc tcacccaggc cacagcctgt    660

cgcacctgcc accgccaaca gcagcccgca gcctgccggg gcttcgcccg tgtggccagg    720

accattctgt cagcctatgt ggtcctgagg ctgccctacc agctggccca gctgctctac    780

ctggccttcc tgtgggacgt ctactctggc tacctgctct gggaggccct ggtctactcc    840

gactacctga tcctactcaa cagctgcctc agccccttcc tctgcctcat ggccagtgcc    900

gacctccgga ccctgctgcg ctccgtgctc tcgtccttcg cggcagctct ctgcgaggag    960

cggccgggca gcttcacgcc cactgagcca cagacccagc tagattctga gggtccaact   1020

ctgccagagc cgatggcaga ggcccagtca cagatggatc ctgtggccca gcctcaggtg   1080

aaccccacac tccagccacg atcggatccc acagctcagc cacagctgaa ccctacggcc   1140

cagccacagt cggatcccac agcccagcca cagctgaacc tcatggccca gccacagtca   1200

gattctgtgg cccagccaca ggcagacact aacgtccaga cccctgcacc tgctgccagt   1260

tctgtgccca gtccctgtga tgaagcttcc ccaaccccat cctcgcatcc taccccaggg   1320

gcccttgagg acccagccac acctcctgcc tctgaaggag aaagccccag cagcaccccg   1380

ccagaggcgg ccccgggcgc aggccccacg tga                                1413
```

<210> SEQ ID NO 10
<211> LENGTH: 468
<212> TYPE: PRT
<213> ORGANISM: Homo sapiens

<400> SEQUENCE: 10

```
Met Asp Thr Thr Met Glu Ala Asp Leu Gly Ala Thr Gly His Arg Pro
  1               5                  10                  15

Arg Thr Glu Leu Asp Asp Glu Asp Ser Tyr Pro Gln Gly Gly Trp Asp
             20                  25                  30

Thr Val Phe Leu Val Ala Leu Leu Leu Leu Gly Leu Pro Ala Asn Gly
         35                  40                  45

Leu Met Ala Trp Leu Ala Gly Ser Gln Ala Arg His Gly Ala Gly Thr
     50                  55                  60

Arg Leu Ala Leu Leu Leu Leu Ser Leu Ala Leu Ser Asp Phe Leu Phe
 65                  70                  75                  80

Leu Ala Ala Ala Ala Phe Gln Ile Leu Glu Ile Arg His Gly Gly His
                 85                  90                  95

Trp Pro Leu Gly Thr Ala Ala Cys Arg Phe Tyr Tyr Phe Leu Trp Gly
            100                 105                 110

Val Ser Tyr Ser Ser Gly Leu Phe Leu Leu Ala Ala Leu Ser Leu Asp
        115                 120                 125

Arg Cys Leu Leu Ala Leu Cys Pro His Trp Tyr Pro Gly His Arg Pro
    130                 135                 140

Val Arg Leu Pro Leu Trp Val Cys Ala Gly Val Trp Val Leu Ala Thr
145                 150                 155                 160

Leu Phe Ser Val Pro Trp Leu Val Phe Pro Glu Ala Ala Val Trp Trp
                165                 170                 175

Tyr Asp Leu Val Ile Cys Leu Asp Phe Trp Asp Ser Glu Glu Leu Ser
            180                 185                 190

Leu Arg Met Leu Glu Val Leu Gly Gly Phe Leu Pro Phe Leu Leu Leu
        195                 200                 205
```

-continued

```
Leu Val Cys His Val Leu Thr Gln Ala Thr Arg Thr Cys His Arg Gln
    210                 215                 220

Gln Gln Pro Ala Ala Cys Arg Gly Phe Ala Arg Val Ala Arg Thr Ile
225                 230                 235                 240

Leu Ser Ala Tyr Val Val Leu Arg Leu Pro Tyr Gln Leu Ala Gln Leu
                245                 250                 255

Leu Tyr Leu Ala Phe Leu Trp Asp Val Tyr Ser Gly Tyr Leu Leu Trp
            260                 265                 270

Glu Ala Leu Val Tyr Ser Asp Tyr Leu Ile Leu Leu Asn Ser Cys Leu
        275                 280                 285

Ser Pro Phe Leu Cys Leu Met Ala Ser Ala Asp Leu Arg Thr Leu Leu
    290                 295                 300

Arg Ser Val Leu Ser Ser Phe Ala Ala Ala Leu Cys Glu Glu Arg Pro
305                 310                 315                 320

Gly Ser Phe Thr Pro Thr Glu Pro Gln Thr Gln Leu Asp Ser Glu Gly
                325                 330                 335

Pro Thr Leu Pro Glu Pro Met Ala Glu Ala Gln Ser Gln Met Asp Pro
            340                 345                 350

Val Ala Gln Pro Gln Val Asn Pro Thr Leu Gln Pro Arg Ser Asp Pro
        355                 360                 365

Thr Ala Gln Pro Gln Leu Asn Pro Thr Ala Gln Pro Gln Ser Asp Pro
    370                 375                 380

Thr Ala Gln Pro Gln Leu Asn Leu Met Ala Gln Pro Gln Ser Asp Ser
385                 390                 395                 400

Val Ala Gln Pro Gln Ala Asp Thr Asn Val Gln Thr Pro Ala Pro Ala
                405                 410                 415

Ala Ser Ser Val Pro Ser Pro Cys Asp Glu Ala Ser Pro Thr Pro Ser
            420                 425                 430

Ser His Pro Thr Pro Gly Ala Leu Glu Asp Pro Ala Thr Pro Pro Ala
        435                 440                 445

Ser Glu Gly Glu Ser Pro Ser Ser Thr Pro Pro Glu Ala Ala Pro Gly
    450                 455                 460

Ala Gly Pro Thr
465


<210> SEQ ID NO 11
<211> LENGTH: 1248
<212> TYPE: DNA
<213> ORGANISM: Homo sapiens

<400> SEQUENCE: 11

atgtcaggga tggaaaaact tcagaatgct tcctggatct accagcagaa actagaagat      60

ccattccaga aacacctgaa cagcaccgag gagtatctgg ccttcctctg cggacctcgg     120

cgcagccact tcttcctccc cgtgtctgtg gtgtatgtgc caatttttgt ggtgggggtc     180

attggcaatg tcctggtgtg cctggtgatt ctgcagcacc aggctatgaa gacgcccacc     240

aactactacc tcttcagcct ggcggtctct gacctcctgg tcctgctcct tggaatgccc     300

ctggaggtct atgagatgtg gcgcaactac cctttcttgt tcgggcccgt gggctgctac     360

ttcaagacgg ccctctttga gaccgtgtgc ttcgcctcca tcctcagcat caccaccgtc     420

agcgtggagc gctacgtggc catcctacac ccgttccgcg ccaaactgca gagcacccgg     480

cgccgggccc tcaggatcct cggcatcgtc tggggcttct ccgtgctctt ctccctgccc     540

aacaccagca tccatggcat caagttccac tacttcccca atgggtccct ggtcccaggt     600
```

-continued

```
tcggccacct gtacggtcat caagcccatg tggatctaca atttcatcat ccaggtcacc    660

tccttcctat tctacctcct ccccatgact gtcatcagtg tcctctacta cctcatggca    720

ctcagactaa agaaagacaa atctcttgag gcagatgaag ggaatgcaaa tattcaaaga    780

ccctgcagaa aatcagtcaa caagatgctg tttgtcttgg tcttagtgtt tgctatctgt    840

tgggccccgt tccacattga ccgactcttc ttcagctttg tggaggagtg gagtgaatcc    900

ctggctgctg tgttcaacct cgtccatgtg gtgtcaggtg tcttcttcta cctgagctca    960

gctgtcaacc ccattatcta taacctactg tctcgccgct tccaggcagc attccagaat   1020

gtgatctctt ctttccacaa acagtggcac tcccagcatg acccacagtt gccacctgcc   1080

cagcggaaca tcttcctgac agaatgccac tttgtggagc tgaccgaaga tataggtccc   1140

caattcccat gtcagtcatc catgcacaac tctcacctcc caacagccct ctctagtgaa   1200

cagatgtcaa gaacaaacta tcaaagcttc cactttaaca aaacctga                1248


<210> SEQ ID NO 12
<211> LENGTH: 415
<212> TYPE: PRT
<213> ORGANISM: Homo sapiens

<400> SEQUENCE: 12

Met Ser Gly Met Glu Lys Leu Gln Asn Ala Ser Trp Ile Tyr Gln Gln
  1               5                  10                  15

Lys Leu Glu Asp Pro Phe Gln Lys His Leu Asn Ser Thr Glu Glu Tyr
             20                  25                  30

Leu Ala Phe Leu Cys Gly Pro Arg Arg Ser His Phe Phe Leu Pro Val
         35                  40                  45

Ser Val Val Tyr Val Pro Ile Phe Val Val Gly Val Ile Gly Asn Val
     50                  55                  60

Leu Val Cys Leu Val Ile Leu Gln His Gln Ala Met Lys Thr Pro Thr
 65                  70                  75                  80

Asn Tyr Tyr Leu Phe Ser Leu Ala Val Ser Asp Leu Leu Val Leu Leu
                 85                  90                  95

Leu Gly Met Pro Leu Glu Val Tyr Glu Met Trp Arg Asn Tyr Pro Phe
            100                 105                 110

Leu Phe Gly Pro Val Gly Cys Tyr Phe Lys Thr Ala Leu Phe Glu Thr
        115                 120                 125

Val Cys Phe Ala Ser Ile Leu Ser Ile Thr Thr Val Ser Val Glu Arg
    130                 135                 140

Tyr Val Ala Ile Leu His Pro Phe Arg Ala Lys Leu Gln Ser Thr Arg
145                 150                 155                 160

Arg Arg Ala Leu Arg Ile Leu Gly Ile Val Trp Gly Phe Ser Val Leu
                165                 170                 175

Phe Ser Leu Pro Asn Thr Ser Ile His Gly Ile Lys Phe His Tyr Phe
            180                 185                 190

Pro Asn Gly Ser Leu Val Pro Gly Ser Ala Thr Cys Thr Val Ile Lys
        195                 200                 205

Pro Met Trp Ile Tyr Asn Phe Ile Ile Gln Val Thr Ser Phe Leu Phe
    210                 215                 220

Tyr Leu Leu Pro Met Thr Val Ile Ser Val Leu Tyr Tyr Leu Met Ala
225                 230                 235                 240

Leu Arg Leu Lys Lys Asp Lys Ser Leu Glu Ala Asp Glu Gly Asn Ala
                245                 250                 255

Asn Ile Gln Arg Pro Cys Arg Lys Ser Val Asn Lys Met Leu Phe Val
```

-continued

```
            260                 265                 270

Leu Val Leu Val Phe Ala Ile Cys Trp Ala Pro Phe His Ile Asp Arg
        275                 280                 285

Leu Phe Phe Ser Phe Val Glu Glu Trp Ser Glu Ser Leu Ala Ala Val
    290                 295                 300

Phe Asn Leu Val His Val Val Ser Gly Val Phe Phe Tyr Leu Ser Ser
305                 310                 315                 320

Ala Val Asn Pro Ile Ile Tyr Asn Leu Leu Ser Arg Arg Phe Gln Ala
                325                 330                 335

Ala Phe Gln Asn Val Ile Ser Ser Phe His Lys Gln Trp His Ser Gln
            340                 345                 350

His Asp Pro Gln Leu Pro Pro Ala Gln Arg Asn Ile Phe Leu Thr Glu
        355                 360                 365

Cys His Phe Val Glu Leu Thr Glu Asp Ile Gly Pro Gln Phe Pro Cys
    370                 375                 380

Gln Ser Ser Met His Asn Ser His Leu Pro Thr Ala Leu Ser Ser Glu
385                 390                 395                 400

Gln Met Ser Arg Thr Asn Tyr Gln Ser Phe His Phe Asn Lys Thr
                405                 410                 415


<210> SEQ ID NO 13
<211> LENGTH: 1173
<212> TYPE: DNA
<213> ORGANISM: Homo sapiens

<400> SEQUENCE: 13

atgccagata ctaatagcac aatcaattta tcactaagca ctcgtgttac tttagcattt     60

tttatgtcct tagtagcttt tgctataatg ctaggaaatg ctttggtcat tttagctttt    120

gtggtggaca aaaaccttag acatcgaagt agttattttt ttcttaactt ggccatctct    180

gacttctttg tgggtgtgat ctccattcct ttgtacatcc ctcacacgct gttcgaatgg    240

gattttggaa aggaaatctg tgtattttgg ctcactactg actatctgtt atgtacagca    300

tctgtatata acattgtcct catcagctat gatcgatacc tgtcagtctc aaatgctgtg    360

tcttatagaa ctcaacatac tggggtcttg aagattgtta ctctgatggt ggccgtttgg    420

gtgctggcct tcttagtgaa tgggccaatg attctagttt cagagtcttg gaaggatgaa    480

ggtagtgaat gtgaacctgg attttttcg gaatggtaca tccttgccat cacatcattc    540

ttggaattcg tgatcccagt catcttagtc gcttatttca acatgaatat ttattggagc    600

ctgtggaagc gtgatcatct cagtaggtgc caaagccatc ctggactgac tgctgtctct    660

tccaacatct gtggacactc attcagaggt agactatctt caaggagatc tctttctgca    720

tcgacagaag ttcctgcatc ctttcattca gagagacaga ggagaaagag tagtctcatg    780

ttttcctcaa gaaccaagat gaatagcaat acaattgctt ccaaaatggg ttccttctcc    840

caatcagatt ctgtagctct tcaccaaagg gaacatgttg aactgcttag agccaggaga    900

ttagccaagt cactggccat tctcttaggg gtttttgctg tttgctgggc tccatattct    960

ctgttcacaa ttgtcctttc attttattcc tcagcaacag gtcctaaatc agtttggtat   1020

agaattgcat tttggcttca gtggttcaat tcctttgtca atcctctttt gtatccattg   1080

tgtcacaagc gctttcaaaa ggctttcttg aaaatatttt gtataaaaaa gcaacctcta   1140

ccatcacaac acagtcggtc agtatcttct taa                                1173


<210> SEQ ID NO 14
```

-continued

<211> LENGTH: 390
<212> TYPE: PRT
<213> ORGANISM: Homo sapiens

<400> SEQUENCE: 14

Met Pro Asp Thr Asn Ser Thr Ile Asn Leu Ser Leu Ser Thr Arg Val
1 5 10 15

Thr Leu Ala Phe Phe Met Ser Leu Val Ala Phe Ala Ile Met Leu Gly
20 25 30

Asn Ala Leu Val Ile Leu Ala Phe Val Val Asp Lys Asn Leu Arg His
35 40 45

Arg Ser Ser Tyr Phe Phe Leu Asn Leu Ala Ile Ser Asp Phe Phe Val
50 55 60

Gly Val Ile Ser Ile Pro Leu Tyr Ile Pro His Thr Leu Phe Glu Trp
65 70 75 80

Asp Phe Gly Lys Glu Ile Cys Val Phe Trp Leu Thr Thr Asp Tyr Leu
85 90 95

Leu Cys Thr Ala Ser Val Tyr Asn Ile Val Leu Ile Ser Tyr Asp Arg
100 105 110

Tyr Leu Ser Val Ser Asn Ala Val Ser Tyr Arg Thr Gln His Thr Gly
115 120 125

Val Leu Lys Ile Val Thr Leu Met Val Ala Val Trp Val Leu Ala Phe
130 135 140

Leu Val Asn Gly Pro Met Ile Leu Val Ser Glu Ser Trp Lys Asp Glu
145 150 155 160

Gly Ser Glu Cys Glu Pro Gly Phe Phe Ser Glu Trp Tyr Ile Leu Ala
165 170 175

Ile Thr Ser Phe Leu Glu Phe Val Ile Pro Val Ile Leu Val Ala Tyr
180 185 190

Phe Asn Met Asn Ile Tyr Trp Ser Leu Trp Lys Arg Asp His Leu Ser
195 200 205

Arg Cys Gln Ser His Pro Gly Leu Thr Ala Val Ser Ser Asn Ile Cys
210 215 220

Gly His Ser Phe Arg Gly Arg Leu Ser Ser Arg Arg Ser Leu Ser Ala
225 230 235 240

Ser Thr Glu Val Pro Ala Ser Phe His Ser Glu Arg Gln Arg Arg Lys
245 250 255

Ser Ser Leu Met Phe Ser Ser Arg Thr Lys Met Asn Ser Asn Thr Ile
260 265 270

Ala Ser Lys Met Gly Ser Phe Ser Gln Ser Asp Ser Val Ala Leu His
275 280 285

Gln Arg Glu His Val Glu Leu Leu Arg Ala Arg Arg Leu Ala Lys Ser
290 295 300

Leu Ala Ile Leu Leu Gly Val Phe Ala Val Cys Trp Ala Pro Tyr Ser
305 310 315 320

Leu Phe Thr Ile Val Leu Ser Phe Tyr Ser Ser Ala Thr Gly Pro Lys
325 330 335

Ser Val Trp Tyr Arg Ile Ala Phe Trp Leu Gln Trp Phe Asn Ser Phe
340 345 350

Val Asn Pro Leu Leu Tyr Pro Leu Cys His Lys Arg Phe Gln Lys Ala
355 360 365

Phe Leu Lys Ile Phe Cys Ile Lys Lys Gln Pro Leu Pro Ser Gln His
370 375 380

Ser Arg Ser Val Ser Ser

-continued 385 390

<210> SEQ ID NO 15
<211> LENGTH: 1128
<212> TYPE: DNA
<213> ORGANISM: Homo sapiens

<400> SEQUENCE: 15 atggcgaacg cgagcgagcc gggtggcagc ggcggcggcg aggcggccgc cctgggcctc 60 aagctggcca cgctcagcct gctgctgtgc gtgagcctag cgggcaacgt gctgttcgcg 120 ctgctgatcg tgcgggagcg cagcctgcac cgcgccccgt actacctgct gctcgacctg 180 tgcctggccg acgggctgcg cgcgctcgcc tgcctcccgg ccgtcatgct ggcggcgcgg 240 cgtgcggcgg ccgcggcggg ggcgccgccg ggcgcgctgg gctgcaagct gctcgccttc 300 ctggccgcgc tcttctgctt ccacgccgcc ttcctgctgc tgggcgtggg cgtcacccgc 360 tacctggcca tcgcgcacca ccgcttctat gcagagcgcc tggccggctg gccgtgcgcc 420 gccatgctgg tgtgcgccgc ctgggcgctg gcgctggccg cggccttccc gccagtgctg 480 gacggcggtg gcgacgacga ggacgcgccg tgcgccctgg agcagcggcc cgacggcgcc 540 cccggcgcgc tgggcttcct gctgctgctg gccgtggtgg tgggcgccac gcacctcgtc 600 tacctccgcc tgctcttctt catccacgac cgccgcaaga tgcggcccgc gcgcctggtg 660 cccgccgtca gccacgactg gaccttccac ggcccgggcg ccaccggcca ggcggccgcc 720 aactggacgg cgggcttcgg ccgcgggccc acgccgcccg cgcttgtggg catccggccc 780 gcagggccgg gccgcggcgc gcgccgcctc ctcgtgctgg aagaattcaa gacggagaag 840 aggctgtgca agatgttcta cgccgtcacg ctgctcttcc tgctcctctg ggggccctac 900 gtcgtggcca gctacctgcg ggtcctggtg cggcccggcg ccgtccccca ggcctacctg 960 acggcctccg tgtggctgac cttcgcgcag gccggcatca accccgtcgt gtgcttcctc 1020 ttcaacaggg agctgaggga ctgcttcagg gcccagttcc cctgctgcca gagcccccgg 1080 accacccagg cgacccatcc ctgcgacctg aaaggcattg gtttatga 1128

<210> SEQ ID NO 16
<211> LENGTH: 375
<212> TYPE: PRT
<213> ORGANISM: Homo sapiens

<400> SEQUENCE: 16

Met Ala Asn Ala Ser Glu Pro Gly Gly Ser Gly Gly Gly Glu Ala Ala
1 5 10 15

Ala Leu Gly Leu Lys Leu Ala Thr Leu Ser Leu Leu Leu Cys Val Ser
20 25 30

Leu Ala Gly Asn Val Leu Phe Ala Leu Leu Ile Val Arg Glu Arg Ser
35 40 45

Leu His Arg Ala Pro Tyr Tyr Leu Leu Leu Asp Leu Cys Leu Ala Asp
50 55 60

Gly Leu Arg Ala Leu Ala Cys Leu Pro Ala Val Met Leu Ala Ala Arg
65 70 75 80

Arg Ala Ala Ala Ala Ala Gly Ala Pro Pro Gly Ala Leu Gly Cys Lys
85 90 95

Leu Leu Ala Phe Leu Ala Ala Leu Phe Cys Phe His Ala Ala Phe Leu
100 105 110

Leu Leu Gly Val Gly Val Thr Arg Tyr Leu Ala Ile Ala His His Arg
115 120 125

-continued

```
Phe Tyr Ala Glu Arg Leu Ala Gly Trp Pro Cys Ala Ala Met Leu Val
    130                 135                 140

Cys Ala Ala Trp Ala Leu Ala Leu Ala Ala Ala Phe Pro Pro Val Leu
145                 150                 155                 160

Asp Gly Gly Gly Asp Asp Glu Asp Ala Pro Cys Ala Leu Glu Gln Arg
                165                 170                 175

Pro Asp Gly Ala Pro Gly Ala Leu Gly Phe Leu Leu Leu Leu Ala Val
            180                 185                 190

Val Val Gly Ala Thr His Leu Val Tyr Leu Arg Leu Leu Phe Phe Ile
        195                 200                 205

His Asp Arg Arg Lys Met Arg Pro Ala Arg Leu Val Pro Ala Val Ser
    210                 215                 220

His Asp Trp Thr Phe His Gly Pro Gly Ala Thr Gly Gln Ala Ala Ala
225                 230                 235                 240

Asn Trp Thr Ala Gly Phe Gly Arg Gly Pro Thr Pro Pro Ala Leu Val
                245                 250                 255

Gly Ile Arg Pro Ala Gly Pro Gly Arg Gly Ala Arg Arg Leu Leu Val
            260                 265                 270

Leu Glu Glu Phe Lys Thr Glu Lys Arg Leu Cys Lys Met Phe Tyr Ala
        275                 280                 285

Val Thr Leu Leu Phe Leu Leu Leu Trp Gly Pro Tyr Val Val Ala Ser
    290                 295                 300

Tyr Leu Arg Val Leu Val Arg Pro Gly Ala Val Pro Gln Ala Tyr Leu
305                 310                 315                 320

Thr Ala Ser Val Trp Leu Thr Phe Ala Gln Ala Gly Ile Asn Pro Val
                325                 330                 335

Val Cys Phe Leu Phe Asn Arg Glu Leu Arg Asp Cys Phe Arg Ala Gln
            340                 345                 350

Phe Pro Cys Cys Gln Ser Pro Arg Thr Thr Gln Ala Thr His Pro Cys
        355                 360                 365

Asp Leu Lys Gly Ile Gly Leu
    370                 375
```

<210> SEQ ID NO 17
<211> LENGTH: 1002
<212> TYPE: DNA
<213> ORGANISM: Homo sapiens

<400> SEQUENCE: 17

```
atgaacacca cagtgatgca aggcttcaac agatctgagc ggtgccccag agacactcgg     60

atagtacagc tggtattccc agccctctac acagtggttt tcttgaccgg catcctgctg    120

aatactttgg ctctgtgggt gtttgttcac atccccagct cctccacctt catcatctac    180

ctcaaaaaca ctttggtggc cgacttgata atgacactca tgcttccttt caaaatcctc    240

tctgactcac acctggcacc ctggcagctc agagcttttg tgtgtcgttt ttcttcggtg    300

atattttatg agaccatgta tgtgggcatc gtgctgttag ggctcatagc ctttgacaga    360

ttcctcaaga tcatcagacc tttgagaaat atttttctaa aaaaacctgt ttttgcaaaa    420

acggtctcaa tcttcatctg gttctttttg ttcttcatct ccctgccaaa tacgatcttg    480

agcaacaagg aagcaacacc atcgtctgtg aaaaagtgtg cttccttaaa ggggcctctg    540

gggctgaaat ggcatcaaat ggtaaataac atatgccagt ttattttctg gactgttttt    600

atcctaatgc ttgtgtttta tgtggttatt gcaaaaaaag tatatgattc ttatagaaag    660
```

-continued

```
tccaaaagta aggacagaaa aaacaacaaa aagctggaag gcaaagtatt tgttgtcgtg    720

gctgtcttct ttgtgtgttt tgctccattt cattttgcca gagttccata tactcacagt    780

caaaccaaca ataagactga ctgtagactg caaaatcaac tgtttattgc taaagaaaca    840

actctctttt tggcagcaac taacatttgt atggatccct taatatacat attcttatgt    900

aaaaaattca cagaaaagct accatgtatg caagggagaa agaccacagc atcaagccaa    960

gaaaatcata gcagtcagac agacaacata accttaggct ga                      1002


<210> SEQ ID NO 18
<211> LENGTH: 333
<212> TYPE: PRT
<213> ORGANISM: Homo sapiens

<400> SEQUENCE: 18

Met Asn Thr Thr Val Met Gln Gly Phe Asn Arg Ser Glu Arg Cys Pro
  1               5                  10                  15

Arg Asp Thr Arg Ile Val Gln Leu Val Phe Pro Ala Leu Tyr Thr Val
             20                  25                  30

Val Phe Leu Thr Gly Ile Leu Leu Asn Thr Leu Ala Leu Trp Val Phe
         35                  40                  45

Val His Ile Pro Ser Ser Ser Thr Phe Ile Ile Tyr Leu Lys Asn Thr
     50                  55                  60

Leu Val Ala Asp Leu Ile Met Thr Leu Met Leu Pro Phe Lys Ile Leu
 65                  70                  75                  80

Ser Asp Ser His Leu Ala Pro Trp Gln Leu Arg Ala Phe Val Cys Arg
                 85                  90                  95

Phe Ser Ser Val Ile Phe Tyr Glu Thr Met Tyr Val Gly Ile Val Leu
            100                 105                 110

Leu Gly Leu Ile Ala Phe Asp Arg Phe Leu Lys Ile Ile Arg Pro Leu
        115                 120                 125

Arg Asn Ile Phe Leu Lys Lys Pro Val Phe Ala Lys Thr Val Ser Ile
    130                 135                 140

Phe Ile Trp Phe Phe Leu Phe Phe Ile Ser Leu Pro Asn Thr Ile Leu
145                 150                 155                 160

Ser Asn Lys Glu Ala Thr Pro Ser Ser Val Lys Lys Cys Ala Ser Leu
                165                 170                 175

Lys Gly Pro Leu Gly Leu Lys Trp His Gln Met Val Asn Asn Ile Cys
            180                 185                 190

Gln Phe Ile Phe Trp Thr Val Phe Ile Leu Met Leu Val Phe Tyr Val
        195                 200                 205

Val Ile Ala Lys Lys Val Tyr Asp Ser Tyr Arg Lys Ser Lys Ser Lys
    210                 215                 220

Asp Arg Lys Asn Asn Lys Lys Leu Glu Gly Lys Val Phe Val Val Val
225                 230                 235                 240

Ala Val Phe Phe Val Cys Phe Ala Pro Phe His Phe Ala Arg Val Pro
                245                 250                 255

Tyr Thr His Ser Gln Thr Asn Asn Lys Thr Asp Cys Arg Leu Gln Asn
            260                 265                 270

Gln Leu Phe Ile Ala Lys Glu Thr Thr Leu Phe Leu Ala Ala Thr Asn
        275                 280                 285

Ile Cys Met Asp Pro Leu Ile Tyr Ile Phe Leu Cys Lys Lys Phe Thr
    290                 295                 300

Glu Lys Leu Pro Cys Met Gln Gly Arg Lys Thr Thr Ala Ser Ser Gln
305                 310                 315                 320
```

```
Glu Asn His Ser Ser Gln Thr Asp Asn Ile Thr Leu Gly
                325                 330


<210> SEQ ID NO 19
<211> LENGTH: 1122
<212> TYPE: DNA
<213> ORGANISM: Homo sapiens

<400> SEQUENCE: 19

atggccaaca ctaccggaga gcctgaggag gtgagcggcg ctctgtcccc accgtccgca     60

tcagcttatg tgaagctggt actgctggga ctgattatgt gcgtgagcct ggcgggtaac    120

gccatcttgt ccctgctggt gctcaaggag cgtgccctgc acaaggctcc ttactacttc    180

ctgctggacc tgtgcctggc cgatggcata cgctctgccg tctgcttccc ctttgtgctg    240

gcttctgtgc gccacggctc ttcatggacc ttcagtgcac tcagctgcaa gattgtggcc    300

tttatggccg tgctcttttg cttccatgcg gccttcatgc tgttctgcat cagcgtcacc    360

cgctacatgg ccatcgccca ccaccgcttc tacgccaagc gcatgacact ctggacatgc    420

gcggctgtca tctgcatggc ctggaccctg tctgtggcca tggccttccc acctgtcttt    480

gacgtgggca cctacaagtt tattcgggag gaggaccagt gcatctttga gcatcgctac    540

ttcaaggcca atgacacgct gggcttcatg cttatgttgg ctgtgctcat ggcagctacc    600

catgctgtct acggcaagct gctcctcttc gagtatcgtc accgcaagat gaagccagtg    660

cagatggtgc cagccatcag ccagaactgg acattccatg gtcccggggc caccggccag    720

gctgctgcca actggatcgc cggctttggc cgtgggccca tgccaccaac cctgctgggt    780

atccggcaga atgggcatgc agccagccgg cggctactgg gcatggacga ggtcaagggt    840

gaaaagcagc tgggccgcat gttctacgcg atcacactgc tctttctgct cctctggtca    900

ccctacatcg tggcctgcta ctggcgagtg tttgtgaaag cctgtgctgt gccccaccgc    960

tacctggcca ctgctgtttg gatgagcttc gcccaggctg ccgtcaaccc aattgtctgc   1020

ttcctgctca acaaggacct caagaagtgc ctgaccactc acgccccctg ctggggcaca   1080

ggaggtgccc cggctcccag agaaccctac tgtgtcatgt ga                      1122


<210> SEQ ID NO 20
<211> LENGTH: 373
<212> TYPE: PRT
<213> ORGANISM: Homo sapiens

<400> SEQUENCE: 20

Met Ala Asn Thr Thr Gly Glu Pro Glu Glu Val Ser Gly Ala Leu Ser
  1               5                  10                  15

Pro Pro Ser Ala Ser Ala Tyr Val Lys Leu Val Leu Leu Gly Leu Ile
             20                  25                  30

Met Cys Val Ser Leu Ala Gly Asn Ala Ile Leu Ser Leu Leu Val Leu
         35                  40                  45

Lys Glu Arg Ala Leu His Lys Ala Pro Tyr Tyr Phe Leu Leu Asp Leu
     50                  55                  60

Cys Leu Ala Asp Gly Ile Arg Ser Ala Val Cys Phe Pro Phe Val Leu
 65                  70                  75                  80

Ala Ser Val Arg His Gly Ser Ser Trp Thr Phe Ser Ala Leu Ser Cys
                 85                  90                  95

Lys Ile Val Ala Phe Met Ala Val Leu Phe Cys Phe His Ala Ala Phe
            100                 105                 110
```

-continued

```
Met Leu Phe Cys Ile Ser Val Thr Arg Tyr Met Ala Ile Ala His His
        115                 120                 125

Arg Phe Tyr Ala Lys Arg Met Thr Leu Trp Thr Cys Ala Ala Val Ile
    130                 135                 140

Cys Met Ala Trp Thr Leu Ser Val Ala Met Ala Phe Pro Pro Val Phe
145                 150                 155                 160

Asp Val Gly Thr Tyr Lys Phe Ile Arg Glu Glu Asp Gln Cys Ile Phe
                165                 170                 175

Glu His Arg Tyr Phe Lys Ala Asn Asp Thr Leu Gly Phe Met Leu Met
            180                 185                 190

Leu Ala Val Leu Met Ala Ala Thr His Ala Val Tyr Gly Lys Leu Leu
        195                 200                 205

Leu Phe Glu Tyr Arg His Arg Lys Met Lys Pro Val Gln Met Val Pro
    210                 215                 220

Ala Ile Ser Gln Asn Trp Thr Phe His Gly Pro Gly Ala Thr Gly Gln
225                 230                 235                 240

Ala Ala Ala Asn Trp Ile Ala Gly Phe Gly Arg Gly Pro Met Pro Pro
                245                 250                 255

Thr Leu Leu Gly Ile Arg Gln Asn Gly His Ala Ala Ser Arg Arg Leu
            260                 265                 270

Leu Gly Met Asp Glu Val Lys Gly Glu Lys Gln Leu Gly Arg Met Phe
        275                 280                 285

Tyr Ala Ile Thr Leu Leu Phe Leu Leu Leu Trp Ser Pro Tyr Ile Val
    290                 295                 300

Ala Cys Tyr Trp Arg Val Phe Val Lys Ala Cys Ala Val Pro His Arg
305                 310                 315                 320

Tyr Leu Ala Thr Ala Val Trp Met Ser Phe Ala Gln Ala Ala Val Asn
                325                 330                 335

Pro Ile Val Cys Phe Leu Leu Asn Lys Asp Leu Lys Lys Cys Leu Thr
            340                 345                 350

Thr His Ala Pro Cys Trp Gly Thr Gly Gly Ala Pro Ala Pro Arg Glu
        355                 360                 365

Pro Tyr Cys Val Met
    370


<210> SEQ ID NO 21
<211> LENGTH: 1053
<212> TYPE: DNA
<213> ORGANISM: Homo sapiens

<400> SEQUENCE: 21

atggctttgg aacagaacca gtcaacagat tattattatg aggaaaatga aatgaatggc     60

acttatgact acagtcaata tgaattgatc tgtatcaaag aagatgtcag agaatttgca    120

aaagttttcc tccctgtatt cctcacaata gctttcgtca ttggacttgc aggcaattcc    180

atggtagtgg caatttatgc ctattacaag aaacagagaa ccaaaacaga tgtgtacatc    240

ctgaatttgg ctgtagcaga tttactcctt ctattcactc tgccttttg ggctgttaat    300

gcagttcatg ggtgggtttt agggaaaata atgtgcaaaa taacttcagc cttgtacaca    360

ctaaactttg tctctggaat gcagtttctg gcttgcatca gcatagacag atatgtggca    420

gtaactaatg tccccagcca atcaggagtg ggaaaaccat gctggatcat ctgtttctgt    480

gtctggatgg ctgccatctt gctgagcata ccccagctgg ttttttatac agtaaatgac    540

aatgctaggt gcattcccat tttcccccgc tacctaggaa catcaatgaa agcattgatt    600
```

-continued

```
caaatgctag agatctgcat tggatttgta gtacccttc ttattatggg ggtgtgctac    660

tttatcacgg caaggacact catgaagatg ccaaacatta aaatatctcg acccctaaaa    720

gttctgctca cagtcgttat agttttcatt gtcactcaac tgccttataa cattgtcaag    780

ttctgccgag ccatagacat catctactcc ctgatcacca gctgcaacat gagcaaacgc    840

atggacatcg ccatccaagt cacagaaagc attgcactct ttcacagctg cctcaaccca    900

atcctttatg tttttatggg agcatctttc aaaaactacg ttatgaaagt ggccaagaaa    960

tatgggtcct ggagaagaca gagacaaagt gtggaggagt ttccttttga ttctgagggt   1020

cctacagagc caaccagtac ttttagcatt taa                                1053
```

<210> SEQ ID NO 22
<211> LENGTH: 350
<212> TYPE: PRT
<213> ORGANISM: Homo sapiens

<400> SEQUENCE: 22

```
Met Ala Leu Glu Gln Asn Gln Ser Thr Asp Tyr Tyr Tyr Glu Glu Asn
  1               5                  10                  15

Glu Met Asn Gly Thr Tyr Asp Tyr Ser Gln Tyr Glu Leu Ile Cys Ile
             20                  25                  30

Lys Glu Asp Val Arg Glu Phe Ala Lys Val Phe Leu Pro Val Phe Leu
         35                  40                  45

Thr Ile Ala Phe Val Ile Gly Leu Ala Gly Asn Ser Met Val Val Ala
     50                  55                  60

Ile Tyr Ala Tyr Tyr Lys Lys Gln Arg Thr Lys Thr Asp Val Tyr Ile
 65                  70                  75                  80

Leu Asn Leu Ala Val Ala Asp Leu Leu Leu Leu Phe Thr Leu Pro Phe
                 85                  90                  95

Trp Ala Val Asn Ala Val His Gly Trp Val Leu Gly Lys Ile Met Cys
            100                 105                 110

Lys Ile Thr Ser Ala Leu Tyr Thr Leu Asn Phe Val Ser Gly Met Gln
        115                 120                 125

Phe Leu Ala Cys Ile Ser Ile Asp Arg Tyr Val Ala Val Thr Asn Val
    130                 135                 140

Pro Ser Gln Ser Gly Val Gly Lys Pro Cys Trp Ile Ile Cys Phe Cys
145                 150                 155                 160

Val Trp Met Ala Ala Ile Leu Leu Ser Ile Pro Gln Leu Val Phe Tyr
                165                 170                 175

Thr Val Asn Asp Asn Ala Arg Cys Ile Pro Ile Phe Pro Arg Tyr Leu
            180                 185                 190

Gly Thr Ser Met Lys Ala Leu Ile Gln Met Leu Glu Ile Cys Ile Gly
        195                 200                 205

Phe Val Val Pro Phe Leu Ile Met Gly Val Cys Tyr Phe Ile Thr Ala
    210                 215                 220

Arg Thr Leu Met Lys Met Pro Asn Ile Lys Ile Ser Arg Pro Leu Lys
225                 230                 235                 240

Val Leu Leu Thr Val Val Ile Val Phe Ile Val Thr Gln Leu Pro Tyr
                245                 250                 255

Asn Ile Val Lys Phe Cys Arg Ala Ile Asp Ile Ile Tyr Ser Leu Ile
            260                 265                 270

Thr Ser Cys Asn Met Ser Lys Arg Met Asp Ile Ala Ile Gln Val Thr
        275                 280                 285

Glu Ser Ile Ala Leu Phe His Ser Cys Leu Asn Pro Ile Leu Tyr Val
```

-continued

```
    290                 295                 300

Phe Met Gly Ala Ser Phe Lys Asn Tyr Val Met Lys Val Ala Lys Lys
305                 310                 315                 320

Tyr Gly Ser Trp Arg Arg Gln Arg Gln Ser Val Glu Glu Phe Pro Phe
                325                 330                 335

Asp Ser Glu Gly Pro Thr Glu Pro Thr Ser Thr Phe Ser Ile
            340                 345                 350


<210> SEQ ID NO 23
<211> LENGTH: 1116
<212> TYPE: DNA
<213> ORGANISM: Homo sapiens

<400> SEQUENCE: 23

atgccaggaa acgccacccc agtgaccacc actgccccgt gggcctccct gggcctctcc     60

gccaagacct gcaacaacgt gtccttcgaa gagagcagga tagtcctggt cgtggtgtac    120

agcgcggtgt gcacgctggg ggtgccggcc aactgcctga ctgcgtggct ggcgctgctg    180

caggtactgc agggcaacgt gctggccgtc tacctgctct gcctggcact ctgcgaactg    240

ctgtacacag gcacgctgcc actctgggtc atctatatcc gcaaccagca ccgctggacc    300

ctaggcctgc tggcctcgaa ggtgaccgcc tacatcttct tctgcaacat ctacgtcagc    360

atcctcttcc tgtgctgcat ctcctgcgac cgcttcgtgg ccgtggtgta cgcgctggag    420

agtcggggcc gccgccgccg gaggaccgcc atcctcatct ccgcctgcat cttcatcctc    480

gtcgggatcg ttcactaccc ggtgttccag acggaagaca aggagacctg ctttgacatg    540

ctgcagatgg acagcaggat tgccgggtac tactacgcca ggttcaccgt tggctttgcc    600

atccctctct ccatcatcgc cttcaccaac caccggattt tcaggagcat caagcagagc    660

atgggcttaa gcgctgccca gaaggccaag gtgaagcact cggccatcgc ggtggttgtc    720

atcttcctag tctgcttcgc cccgtaccac ctggttctcc tcgtcaaagc cgctgccttt    780

tcctactaca gaggagacag gaacgccatg tgcggcttgg aggaaaggct gtacacagcc    840

tctgtggtgt ttctgtgcct gtccacggtg aacggcgtgg ctgaccccat tatctacgtg    900

ctggccacgg accattcccg ccaagaagtg tccagaatcc ataaggggtg gaaagagtgg    960

tccatgaaga cagacgtcac caggctcacc cacagcaggg acaccgagga gctgcagtcg   1020

cccgtggccc ttgcagacca ctacaccttc tccaggcccg tgcacccacc agggtcacca   1080

tgccctgcaa agaggctgat tgaggagtcc tgctga                             1116


<210> SEQ ID NO 24
<211> LENGTH: 371
<212> TYPE: PRT
<213> ORGANISM: Homo sapiens

<400> SEQUENCE: 24

Met Pro Gly Asn Ala Thr Pro Val Thr Thr Thr Ala Pro Trp Ala Ser
  1               5                  10                  15

Leu Gly Leu Ser Ala Lys Thr Cys Asn Asn Val Ser Phe Glu Glu Ser
             20                  25                  30

Arg Ile Val Leu Val Val Val Tyr Ser Ala Val Cys Thr Leu Gly Val
         35                  40                  45

Pro Ala Asn Cys Leu Thr Ala Trp Leu Ala Leu Leu Gln Val Leu Gln
     50                  55                  60

Gly Asn Val Leu Ala Val Tyr Leu Leu Cys Leu Ala Leu Cys Glu Leu
 65                  70                  75                  80
```

-continued

```
Leu Tyr Thr Gly Thr Leu Pro Leu Trp Val Ile Tyr Ile Arg Asn Gln
                85                  90                  95

His Arg Trp Thr Leu Gly Leu Leu Ala Ser Lys Val Thr Ala Tyr Ile
            100                 105                 110

Phe Phe Cys Asn Ile Tyr Val Ser Ile Leu Phe Leu Cys Cys Ile Ser
        115                 120                 125

Cys Asp Arg Phe Val Ala Val Val Tyr Ala Leu Glu Ser Arg Gly Arg
    130                 135                 140

Arg Arg Arg Arg Thr Ala Ile Leu Ile Ser Ala Cys Ile Phe Ile Leu
145                 150                 155                 160

Val Gly Ile Val His Tyr Pro Val Phe Gln Thr Glu Asp Lys Glu Thr
                165                 170                 175

Cys Phe Asp Met Leu Gln Met Asp Ser Arg Ile Ala Gly Tyr Tyr Tyr
            180                 185                 190

Ala Arg Phe Thr Val Gly Phe Ala Ile Pro Leu Ser Ile Ile Ala Phe
        195                 200                 205

Thr Asn His Arg Ile Phe Arg Ser Ile Lys Gln Ser Met Gly Leu Ser
    210                 215                 220

Ala Ala Gln Lys Ala Lys Val Lys His Ser Ala Ile Ala Val Val Val
225                 230                 235                 240

Ile Phe Leu Val Cys Phe Ala Pro Tyr His Leu Val Leu Leu Val Lys
                245                 250                 255

Ala Ala Ala Phe Ser Tyr Tyr Arg Gly Asp Arg Asn Ala Met Cys Gly
            260                 265                 270

Leu Glu Glu Arg Leu Tyr Thr Ala Ser Val Val Phe Leu Cys Leu Ser
        275                 280                 285

Thr Val Asn Gly Val Ala Asp Pro Ile Ile Tyr Val Leu Ala Thr Asp
    290                 295                 300

His Ser Arg Gln Glu Val Ser Arg Ile His Lys Gly Trp Lys Glu Trp
305                 310                 315                 320

Ser Met Lys Thr Asp Val Thr Arg Leu Thr His Ser Arg Asp Thr Glu
                325                 330                 335

Glu Leu Gln Ser Pro Val Ala Leu Ala Asp His Tyr Thr Phe Ser Arg
            340                 345                 350

Pro Val His Pro Pro Gly Ser Pro Cys Pro Ala Lys Arg Leu Ile Glu
        355                 360                 365

Glu Ser Cys
    370


<210> SEQ ID NO 25
<211> LENGTH: 1113
<212> TYPE: DNA
<213> ORGANISM: Homo sapiens

<400> SEQUENCE: 25

atggcgaact atagccatgc agctgacaac attttgcaaa atctctcgcc tctaacagcc      60

tttctgaaac tgacttcctt gggtttcata ataggagtca gcgtggtggg caacctcctg     120

atctccattt tgctagtgaa agataagacc ttgcatagag caccttacta cttcctgttg     180

gatctttgct gttcagatat cctcagatct gcaatttgtt tcccatttgt gttcaactct     240

gtcaaaaatg gctctacctg gacttatggg actctgactt gcaaagtgat tgcctttctg     300

ggggttttgt cctgtttcca cactgctttc atgctcttct gcatcagtgt caccagatac     360

ttagctatcg cccatcaccg cttctataca aagaggctga ccttttggac gtgtctggct     420
```

-continued

```
gtgatctgta tggtgtggac tctgtctgtg gccatggcat ttcccccggt tttagacgtg    480

ggcacttact cattcattag ggaggaagat caatgcacct tccaacaccg ctccttcagg    540

gctaatgatt ccttaggatt tatgctgctt cttgctctca tcctcctagc cacacagctt    600

gtctacctca agctgatatt tttcgtccac gatcgaagaa aaatgaagcc agtccagttt    660

gtagcagcag tcagccagaa ctggactttt catggtcctg gagccagtgg ccaggcagct    720

gccaattggc tagcaggatt tggaaggggt cccacaccac ccaccttgct gggcatcagg    780

caaaatgcaa acaccacagg cagaagaagg ctattggtct tagacgagtt caaaatggag    840

aaaagaatca gcagaatgtt ctatataatg acttttctgt ttctaacctt gtggggcccc    900

tacctggtgg cctgttattg gagagttttt gcaagagggc ctgtagtacc agggggattt    960

ctaacagctg ctgtctggat gagttttgcc caagcaggaa tcaatccttt tgtctgcatt   1020

ttctcaaaca gggagctgag gcgctgtttc agcacaaccc ttctttactg cagaaaatcc   1080

aggttaccaa gggaacctta ctgtgttata tga                                1113
```

<210> SEQ ID NO 26
<211> LENGTH: 370
<212> TYPE: PRT
<213> ORGANISM: Homo sapiens

<400> SEQUENCE: 26

```
Met Ala Asn Tyr Ser His Ala Ala Asp Asn Ile Leu Gln Asn Leu Ser
  1               5                  10                  15

Pro Leu Thr Ala Phe Leu Lys Leu Thr Ser Leu Gly Phe Ile Ile Gly
             20                  25                  30

Val Ser Val Val Gly Asn Leu Leu Ile Ser Ile Leu Leu Val Lys Asp
         35                  40                  45

Lys Thr Leu His Arg Ala Pro Tyr Tyr Phe Leu Leu Asp Leu Cys Cys
     50                  55                  60

Ser Asp Ile Leu Arg Ser Ala Ile Cys Phe Pro Phe Val Phe Asn Ser
 65                  70                  75                  80

Val Lys Asn Gly Ser Thr Trp Thr Tyr Gly Thr Leu Thr Cys Lys Val
                 85                  90                  95

Ile Ala Phe Leu Gly Val Leu Ser Cys Phe His Thr Ala Phe Met Leu
            100                 105                 110

Phe Cys Ile Ser Val Thr Arg Tyr Leu Ala Ile Ala His His Arg Phe
        115                 120                 125

Tyr Thr Lys Arg Leu Thr Phe Trp Thr Cys Leu Ala Val Ile Cys Met
    130                 135                 140

Val Trp Thr Leu Ser Val Ala Met Ala Phe Pro Pro Val Leu Asp Val
145                 150                 155                 160

Gly Thr Tyr Ser Phe Ile Arg Glu Glu Asp Gln Cys Thr Phe Gln His
                165                 170                 175

Arg Ser Phe Arg Ala Asn Asp Ser Leu Gly Phe Met Leu Leu Leu Ala
            180                 185                 190

Leu Ile Leu Leu Ala Thr Gln Leu Val Tyr Leu Lys Leu Ile Phe Phe
        195                 200                 205

Val His Asp Arg Arg Lys Met Lys Pro Val Gln Phe Val Ala Ala Val
    210                 215                 220

Ser Gln Asn Trp Thr Phe His Gly Pro Gly Ala Ser Gly Gln Ala Ala
225                 230                 235                 240

Ala Asn Trp Leu Ala Gly Phe Gly Arg Gly Pro Thr Pro Pro Thr Leu
```

-continued

```
                245                 250                 255

Leu Gly Ile Arg Gln Asn Ala Asn Thr Thr Gly Arg Arg Arg Leu Leu
            260                 265                 270

Val Leu Asp Glu Phe Lys Met Glu Lys Arg Ile Ser Arg Met Phe Tyr
        275                 280                 285

Ile Met Thr Phe Leu Phe Leu Thr Leu Trp Gly Pro Tyr Leu Val Ala
    290                 295                 300

Cys Tyr Trp Arg Val Phe Ala Arg Gly Pro Val Val Pro Gly Gly Phe
305                 310                 315                 320

Leu Thr Ala Ala Val Trp Met Ser Phe Ala Gln Ala Gly Ile Asn Pro
                325                 330                 335

Phe Val Cys Ile Phe Ser Asn Arg Glu Leu Arg Arg Cys Phe Ser Thr
            340                 345                 350

Thr Leu Leu Tyr Cys Arg Lys Ser Arg Leu Pro Arg Glu Pro Tyr Cys
        355                 360                 365

Val Ile
    370


<210> SEQ ID NO 27
<211> LENGTH: 1080
<212> TYPE: DNA
<213> ORGANISM: Homo sapiens

<400> SEQUENCE: 27

atgcaggtcc cgaacagcac cggcccggac aacgcgacgc tgcagatgct gcggaacccg     60

gcgatcgcgg tggccctgcc cgtggtgtac tcgctggtgg cggcggtcag catcccgggc    120

aacctcttct ctctgtgggt gctgtgccgg cgcatggggc ccagatcccc gtcggtcatc    180

ttcatgatca acctgagcgt cacggacctg atgctggcca gcgtgttgcc tttccaaatc    240

tactaccatt gcaaccgcca ccactgggta ttcggggtgc tgctttgcaa cgtggtgacc    300

gtggcctttt acgcaaacat gtattccagc atcctcacca tgacctgtat cagcgtggag    360

cgcttcctgg gggtcctgta cccgctcagc tccaagcgct ggcgccgccg tcgttacgcg    420

gtggccgcgt gtgcagggac ctggctgctg ctcctgaccg ccctgtgccc gctggcgcgc    480

accgatctca cctacccggt gcacgccctg ggcatcatca cctgcttcga cgtcctcaag    540

tggacgatgc tccccagcgt ggccatgtgg gccgtgttcc tcttcaccat cttcatcctg    600

ctgttcctca tcccgttcgt gatcaccgtg gcttgttaca cggccaccat cctcaagctg    660

ttgcgcacgg aggaggcgca cggccgggag cagcggaggc gcgcggtggg cctggccgcg    720

gtggtcttgc tggcctttgt cacctgcttc gcccccaaca acttcgtgct cctggcgcac    780

atcgtgagcc gcctgttcta cggcaagagc tactaccacg tgtacaagct cacgctgtgt    840

ctcagctgcc tcaacaactg tctggacccg tttgtttatt actttgcgtc ccgggaattc    900

cagctgcgcc tgcgggaata tttgggctgc cgccgggtgc ccagagacac cctggacacg    960

cgccgcgaga gcctcttctc cgccaggacc acgtccgtgc gctccgaggc cggtgcgcac   1020

cctgaaggga tggagggagc caccaggccc ggcctccaga ggcaggagag tgtgttctga   1080


<210> SEQ ID NO 28
<211> LENGTH: 359
<212> TYPE: PRT
<213> ORGANISM: Homo sapiens

<400> SEQUENCE: 28

Met Gln Val Pro Asn Ser Thr Gly Pro Asp Asn Ala Thr Leu Gln Met
```

-continued

```
  1               5                  10                  15

Leu Arg Asn Pro Ala Ile Ala Val Ala Leu Pro Val Val Tyr Ser Leu
            20                  25                  30

Val Ala Ala Val Ser Ile Pro Gly Asn Leu Phe Ser Leu Trp Val Leu
        35                  40                  45

Cys Arg Arg Met Gly Pro Arg Ser Pro Ser Val Ile Phe Met Ile Asn
    50                  55                  60

Leu Ser Val Thr Asp Leu Met Leu Ala Ser Val Leu Pro Phe Gln Ile
65                  70                  75                  80

Tyr Tyr His Cys Asn Arg His His Trp Val Phe Gly Val Leu Leu Cys
                85                  90                  95

Asn Val Val Thr Val Ala Phe Tyr Ala Asn Met Tyr Ser Ser Ile Leu
            100                 105                 110

Thr Met Thr Cys Ile Ser Val Glu Arg Phe Leu Gly Val Leu Tyr Pro
        115                 120                 125

Leu Ser Ser Lys Arg Trp Arg Arg Arg Arg Tyr Ala Val Ala Ala Cys
    130                 135                 140

Ala Gly Thr Trp Leu Leu Leu Leu Thr Ala Leu Cys Pro Leu Ala Arg
145                 150                 155                 160

Thr Asp Leu Thr Tyr Pro Val His Ala Leu Gly Ile Ile Thr Cys Phe
                165                 170                 175

Asp Val Leu Lys Trp Thr Met Leu Pro Ser Val Ala Met Trp Ala Val
            180                 185                 190

Phe Leu Phe Thr Ile Phe Ile Leu Leu Phe Leu Ile Pro Phe Val Ile
        195                 200                 205

Thr Val Ala Cys Tyr Thr Ala Thr Ile Leu Lys Leu Leu Arg Thr Glu
    210                 215                 220

Glu Ala His Gly Arg Glu Gln Arg Arg Arg Ala Val Gly Leu Ala Ala
225                 230                 235                 240

Val Val Leu Leu Ala Phe Val Thr Cys Phe Ala Pro Asn Asn Phe Val
                245                 250                 255

Leu Leu Ala His Ile Val Ser Arg Leu Phe Tyr Gly Lys Ser Tyr Tyr
            260                 265                 270

His Val Tyr Lys Leu Thr Leu Cys Leu Ser Cys Leu Asn Asn Cys Leu
        275                 280                 285

Asp Pro Phe Val Tyr Tyr Phe Ala Ser Arg Glu Phe Gln Leu Arg Leu
    290                 295                 300

Arg Glu Tyr Leu Gly Cys Arg Arg Val Pro Arg Asp Thr Leu Asp Thr
305                 310                 315                 320

Arg Arg Glu Ser Leu Phe Ser Ala Arg Thr Thr Ser Val Arg Ser Glu
                325                 330                 335

Ala Gly Ala His Pro Glu Gly Met Glu Gly Ala Thr Arg Pro Gly Leu
            340                 345                 350

Gln Arg Gln Glu Ser Val Phe
        355


<210> SEQ ID NO 29
<211> LENGTH: 1503
<212> TYPE: DNA
<213> ORGANISM: Homo sapiens

<400> SEQUENCE: 29

atggagcgtc cctgggagga cagcccaggc ccggaggggg cagctgaggg ctcgcctgtg      60

ccagtcgccg ccggggcgcg ctccggtgcc gcggcgagtg gcacaggctg gcagccatgg     120
```

-continued

```
gctgagtgcc cgggacccaa ggggaggggg caactgctgg cgaccgccgg ccctttgcgt    180

cgctggcccg ccccctcgcc tgccagctcc agccccgccc ccggagcggc gtccgctcac    240

tcggttcaag gcagcgcgac tgcgggtggc gcacgaccag ggcgcagacc ttggggcgcg    300

cggcccatgg agtcggggct gctgcggccg gcgccggtga gcgaggtcat cgtcctgcat    360

tacaactaca ccggcaagct ccgcggtgcg agctaccagc cgggtgccgg cctgcgcgcc    420

gacgccgtgg tgtgcctggc ggtgtgcgcc ttcatcgtgc tagagaatct agccgtgttg    480

ttggtgctcg gacgccaccc gcgcttccac gctcccatgt tcctgctcct gggcagcctc    540

acgttgtcgg atctgctggc aggcgccgcc tacgccgcca acatcctact gtcggggccg    600

ctcacgctga aactgtcccc cgcgctctgg ttcgcacggg agggaggcgt cttcgtggca    660

ctcactgcgt ccgtgctgag cctcctggcc atcgcgctgg agcgcagcct caccatggcg    720

cgcagggggc ccgcgcccgt ctccagtcgg gggcgcacgc tggcgatggc agccgcggcc    780

tggggcgtgt cgctgctcct cgggctcctg ccagcgctgg gctggaattg cctgggtcgc    840

ctggacgctt gctccactgt cttgccgctc tacgccaagg cctacgtgct cttctgcgtg    900

ctcgccttcg tgggcatcct ggccgcgatc tgtgcactct acgcgcgcat ctactgccag    960

gtacgcgcca acgcgcggcg cctgccggca cggcccggga ctgcggggac cacctcgacc   1020

cgggcgcgtc gcaagccgcg ctctctggcc ttgctgcgca cgctcagcgt ggtgctcctg   1080

gcctttgtgg catgttgggg ccccctcttc ctgctgctgt tgctcgacgt ggcgtgcccg   1140

gcgcgcacct gtcctgtact cctgcaggcc gatcccttcc tgggactggc catggccaac   1200

tcacttctga accccatcat ctacacgctc accaaccgcg acctgcgcca cgcgctcctg   1260

cgcctggtct gctgcggacg ccactcctgc ggcagagacc cgagtggctc ccagcagtcg   1320

gcgagcgcgg ctgaggcttc cgggggcctg cgccgctgcc tgcccccggg ccttgatggg   1380

agcttcagcg gctcggagcg ctcatcgccc cagcgcgacg ggctggacac cagcggctcc   1440

acaggcagcc ccggtgcacc cacagccgcc cggactctgg tatcagaacc ggctgcagac   1500

tga                                                                 1503
```

<210> SEQ ID NO 30
<211> LENGTH: 500
<212> TYPE: PRT
<213> ORGANISM: Homo sapiens

<400> SEQUENCE: 30

```
Met Glu Arg Pro Trp Glu Asp Ser Pro Gly Pro Glu Gly Ala Ala Glu
  1               5                  10                  15

Gly Ser Pro Val Pro Val Ala Ala Gly Ala Arg Ser Gly Ala Ala Ala
             20                  25                  30

Ser Gly Thr Gly Trp Gln Pro Trp Ala Glu Cys Pro Gly Pro Lys Gly
         35                  40                  45

Arg Gly Gln Leu Leu Ala Thr Ala Gly Pro Leu Arg Arg Trp Pro Ala
     50                  55                  60

Pro Ser Pro Ala Ser Ser Ser Pro Ala Pro Gly Ala Ala Ser Ala His
 65                  70                  75                  80

Ser Val Gln Gly Ser Ala Thr Ala Gly Gly Ala Arg Pro Gly Arg Arg
                 85                  90                  95

Pro Trp Gly Ala Arg Pro Met Glu Ser Gly Leu Leu Arg Pro Ala Pro
            100                 105                 110

Val Ser Glu Val Ile Val Leu His Tyr Asn Tyr Thr Gly Lys Leu Arg
```

-continued

```
        115                 120                 125

Gly Ala Ser Tyr Gln Pro Gly Ala Gly Leu Arg Ala Asp Ala Val Val
    130                 135                 140

Cys Leu Ala Val Cys Ala Phe Ile Val Leu Glu Asn Leu Ala Val Leu
145                 150                 155                 160

Leu Val Leu Gly Arg His Pro Arg Phe His Ala Pro Met Phe Leu Leu
                165                 170                 175

Leu Gly Ser Leu Thr Leu Ser Asp Leu Leu Ala Gly Ala Ala Tyr Ala
            180                 185                 190

Ala Asn Ile Leu Leu Ser Gly Pro Leu Thr Leu Lys Leu Ser Pro Ala
        195                 200                 205

Leu Trp Phe Ala Arg Glu Gly Gly Val Phe Val Ala Leu Thr Ala Ser
    210                 215                 220

Val Leu Ser Leu Leu Ala Ile Ala Leu Glu Arg Ser Leu Thr Met Ala
225                 230                 235                 240

Arg Arg Gly Pro Ala Pro Val Ser Ser Arg Gly Arg Thr Leu Ala Met
                245                 250                 255

Ala Ala Ala Ala Trp Gly Val Ser Leu Leu Leu Gly Leu Leu Pro Ala
            260                 265                 270

Leu Gly Trp Asn Cys Leu Gly Arg Leu Asp Ala Cys Ser Thr Val Leu
        275                 280                 285

Pro Leu Tyr Ala Lys Ala Tyr Val Leu Phe Cys Val Leu Ala Phe Val
    290                 295                 300

Gly Ile Leu Ala Ala Ile Cys Ala Leu Tyr Ala Arg Ile Tyr Cys Gln
305                 310                 315                 320

Val Arg Ala Asn Ala Arg Arg Leu Pro Ala Arg Pro Gly Thr Ala Gly
                325                 330                 335

Thr Thr Ser Thr Arg Ala Arg Arg Lys Pro Arg Ser Leu Ala Leu Leu
            340                 345                 350

Arg Thr Leu Ser Val Val Leu Leu Ala Phe Val Ala Cys Trp Gly Pro
        355                 360                 365

Leu Phe Leu Leu Leu Leu Leu Asp Val Ala Cys Pro Ala Arg Thr Cys
    370                 375                 380

Pro Val Leu Leu Gln Ala Asp Pro Phe Leu Gly Leu Ala Met Ala Asn
385                 390                 395                 400

Ser Leu Leu Asn Pro Ile Ile Tyr Thr Leu Thr Asn Arg Asp Leu Arg
                405                 410                 415

His Ala Leu Leu Arg Leu Val Cys Cys Gly Arg His Ser Cys Gly Arg
            420                 425                 430

Asp Pro Ser Gly Ser Gln Gln Ser Ala Ser Ala Ala Glu Ala Ser Gly
        435                 440                 445

Gly Leu Arg Arg Cys Leu Pro Pro Gly Leu Asp Gly Ser Phe Ser Gly
    450                 455                 460

Ser Glu Arg Ser Ser Pro Gln Arg Asp Gly Leu Asp Thr Ser Gly Ser
465                 470                 475                 480

Thr Gly Ser Pro Gly Ala Pro Thr Ala Ala Arg Thr Leu Val Ser Glu
                485                 490                 495

Pro Ala Ala Asp
            500
```

<210> SEQ ID NO 31
<211> LENGTH: 1029
<212> TYPE: DNA
<213> ORGANISM: Homo sapiens -continued

<400> SEQUENCE: 31 atgcaagccg tcgacaatct cacctctgcg cctgggaaca ccagtctgtg caccagagac 60 tacaaaatca cccaggtcct cttcccactg ctctacactg tcctgttttt tgttggactt 120 atcacaaatg gcctggcgat gaggattttc tttcaaatcc ggagtaaatc aaactttatt 180 atttttctta agaacacagt catttctgat cttctcatga ttctgacttt tccattcaaa 240 attcttagtg atgccaaact gggaacagga ccactgagaa cttttgtgtg tcaagttacc 300 tccgtcatat tttatttcac aatgtatatc agtatttcat tcctgggact gataactatc 360 gatcgctacc agaagaccac caggccattt aaaacatcca accccaaaaa tctcttgggg 420 gctaagattc tctctgttgt catctgggca ttcatgttct tactctcttt gcctaacatg 480 attctgacca acaggcagcc gagagacaag aatgtgaaga aatgctcttt ccttaaatca 540 gagttcggtc tagtctggca tgaaatagta aattacatct gtcaagtcat tttctggatt 600 aatttcttaa ttgttattgt atgttataca ctcattacaa aagaactgta ccggtcatac 660 gtaagaacga ggggtgtagg taaagtcccc aggaaaaagg tgaacgtcaa agttttcatt 720 atcattgctg tattctttat ttgttttgtt cctttccatt ttgcccgaat tccttacacc 780 ctgagccaaa cccgggatgt ctttgactgc actgctgaaa atactctgtt ctatgtgaaa 840 gagagcactc tgtggttaac ttccttaaat gcatgcctgg atccgttcat ctatttttc 900 ctttgcaagt ccttcagaaa ttccttgata agtatgctga agtgccccaa ttctgcaaca 960 tctctgtccc aggacaatag gaaaaaagaa caggatggtg gtgacccaaa tgaagagact 1020 ccaatgtaa 1029

<210> SEQ ID NO 32
<211> LENGTH: 342
<212> TYPE: PRT
<213> ORGANISM: Homo sapiens

<400> SEQUENCE: 32

Met Gln Ala Val Asp Asn Leu Thr Ser Ala Pro Gly Asn Thr Ser Leu
1 5 10 15

Cys Thr Arg Asp Tyr Lys Ile Thr Gln Val Leu Phe Pro Leu Leu Tyr
20 25 30

Thr Val Leu Phe Phe Val Gly Leu Ile Thr Asn Gly Leu Ala Met Arg
35 40 45

Ile Phe Phe Gln Ile Arg Ser Lys Ser Asn Phe Ile Ile Phe Leu Lys
50 55 60

Asn Thr Val Ile Ser Asp Leu Leu Met Ile Leu Thr Phe Pro Phe Lys
65 70 75 80

Ile Leu Ser Asp Ala Lys Leu Gly Thr Gly Pro Leu Arg Thr Phe Val
85 90 95

Cys Gln Val Thr Ser Val Ile Phe Tyr Phe Thr Met Tyr Ile Ser Ile
100 105 110

Ser Phe Leu Gly Leu Ile Thr Ile Asp Arg Tyr Gln Lys Thr Thr Arg
115 120 125

Pro Phe Lys Thr Ser Asn Pro Lys Asn Leu Leu Gly Ala Lys Ile Leu
130 135 140

Ser Val Val Ile Trp Ala Phe Met Phe Leu Leu Ser Leu Pro Asn Met
145 150 155 160

Ile Leu Thr Asn Arg Gln Pro Arg Asp Lys Asn Val Lys Lys Cys Ser
165 170 175

-continued

```
Phe Leu Lys Ser Glu Phe Gly Leu Val Trp His Glu Ile Val Asn Tyr
            180                 185                 190

Ile Cys Gln Val Ile Phe Trp Ile Asn Phe Leu Ile Val Ile Val Cys
        195                 200                 205

Tyr Thr Leu Ile Thr Lys Glu Leu Tyr Arg Ser Tyr Val Arg Thr Arg
    210                 215                 220

Gly Val Gly Lys Val Pro Arg Lys Lys Val Asn Val Lys Val Phe Ile
225                 230                 235                 240

Ile Ile Ala Val Phe Phe Ile Cys Phe Val Pro Phe His Phe Ala Arg
                245                 250                 255

Ile Pro Tyr Thr Leu Ser Gln Thr Arg Asp Val Phe Asp Cys Thr Ala
            260                 265                 270

Glu Asn Thr Leu Phe Tyr Val Lys Glu Ser Thr Leu Trp Leu Thr Ser
        275                 280                 285

Leu Asn Ala Cys Leu Asp Pro Phe Ile Tyr Phe Phe Leu Cys Lys Ser
    290                 295                 300

Phe Arg Asn Ser Leu Ile Ser Met Leu Lys Cys Pro Asn Ser Ala Thr
305                 310                 315                 320

Ser Leu Ser Gln Asp Asn Arg Lys Lys Glu Gln Asp Gly Gly Asp Pro
                325                 330                 335

Asn Glu Glu Thr Pro Met
            340


<210> SEQ ID NO 33
<211> LENGTH: 1077
<212> TYPE: DNA
<213> ORGANISM: Homo sapiens

<400> SEQUENCE: 33

atgtcggtct gctaccgtcc cccagggaac gagacactgc tgagctggaa gacttcgcgg     60

gccacaggca cagccttcct gctgctggcg gcgctgctgg ggctgcctgg caacggcttc    120

gtggtgtgga gcttggcggg ctggcggcct gcacgggggc gaccgctggc ggccacgctt    180

gtgctgcacc tggcgctggc cgacggcgcg gtgctgctgc tcacgccgct ctttgtggcc    240

ttcctgaccc ggcaggcctg gccgctgggc caggcgggct gcaaggcggt gtactacgtg    300

tgcgcgctca gcatgtacgc cagcgtgctg ctcaccggcc tgctcagcct gcagcgctgc    360

ctcgcagtca cccgcccctt cctggcgcct cggctgcgca gcccggccct ggcccgccgc    420

ctgctgctgg cggtctggct ggccgccctg ttgctcgccg tcccggccgc cgtctaccgc    480

cacctgtgga gggaccgcgt atgccagctg tgccacccgt cgccggtcca cgccgccgcc    540

cacctgagcc tggagactct gaccgctttc gtgcttcctt tcgggctgat gctcggctgc    600

tacagcgtga cgctggcacg gctgcggggc gcccgctggg gctccgggcg gcacggggcg    660

cgggtgggcc ggctggtgag cgccatcgtg cttgccttcg gcttgctctg ggccccctac    720

cacgcagtca accttctgca ggcggtcgca gcgctggctc caccggaagg ggccttggcg    780

aagctgggcg gagccggcca ggcggcgcga gcgggaacta cggccttggc cttcttcagt    840

tctagcgtca acccggtgct ctacgtcttc accgctggag atctgctgcc ccgggcaggt    900

ccccgtttcc tcacgcggct cttcgaaggc tctggggagg cccgaggggg cggccgctct    960

agggaaggga ccatggagct ccgaactacc cctcagctga aagtggtggg gcagggccgc   1020

ggcaatggag acccgggggg tgggatggag aaggacggtc cggaatggga cctttga      1077
```

-continued

<210> SEQ ID NO 34
<211> LENGTH: 358
<212> TYPE: PRT
<213> ORGANISM: Homo sapiens

<400> SEQUENCE: 34

Met Ser Val Cys Tyr Arg Pro Pro Gly Asn Glu Thr Leu Leu Ser Trp
1 5 10 15

Lys Thr Ser Arg Ala Thr Gly Thr Ala Phe Leu Leu Leu Ala Ala Leu
20 25 30

Leu Gly Leu Pro Gly Asn Gly Phe Val Val Trp Ser Leu Ala Gly Trp
35 40 45

Arg Pro Ala Arg Gly Arg Pro Leu Ala Ala Thr Leu Val Leu His Leu
50 55 60

Ala Leu Ala Asp Gly Ala Val Leu Leu Leu Thr Pro Leu Phe Val Ala
65 70 75 80

Phe Leu Thr Arg Gln Ala Trp Pro Leu Gly Gln Ala Gly Cys Lys Ala
85 90 95

Val Tyr Tyr Val Cys Ala Leu Ser Met Tyr Ala Ser Val Leu Leu Thr
100 105 110

Gly Leu Leu Ser Leu Gln Arg Cys Leu Ala Val Thr Arg Pro Phe Leu
115 120 125

Ala Pro Arg Leu Arg Ser Pro Ala Leu Ala Arg Arg Leu Leu Leu Ala
130 135 140

Val Trp Leu Ala Ala Leu Leu Leu Ala Val Pro Ala Ala Val Tyr Arg
145 150 155 160

His Leu Trp Arg Asp Arg Val Cys Gln Leu Cys His Pro Ser Pro Val
165 170 175

His Ala Ala Ala His Leu Ser Leu Glu Thr Leu Thr Ala Phe Val Leu
180 185 190

Pro Phe Gly Leu Met Leu Gly Cys Tyr Ser Val Thr Leu Ala Arg Leu
195 200 205

Arg Gly Ala Arg Trp Gly Ser Gly Arg His Gly Ala Arg Val Gly Arg
210 215 220

Leu Val Ser Ala Ile Val Leu Ala Phe Gly Leu Leu Trp Ala Pro Tyr
225 230 235 240

His Ala Val Asn Leu Leu Gln Ala Val Ala Ala Leu Ala Pro Pro Glu
245 250 255

Gly Ala Leu Ala Lys Leu Gly Gly Ala Gly Gln Ala Ala Arg Ala Gly
260 265 270

Thr Thr Ala Leu Ala Phe Phe Ser Ser Ser Val Asn Pro Val Leu Tyr
275 280 285

Val Phe Thr Ala Gly Asp Leu Leu Pro Arg Ala Gly Pro Arg Phe Leu
290 295 300

Thr Arg Leu Phe Glu Gly Ser Gly Glu Ala Arg Gly Gly Gly Arg Ser
305 310 315 320

Arg Glu Gly Thr Met Glu Leu Arg Thr Thr Pro Gln Leu Lys Val Val
325 330 335

Gly Gln Gly Arg Gly Asn Gly Asp Pro Gly Gly Gly Met Glu Lys Asp
340 345 350

Gly Pro Glu Trp Asp Leu
355

<210> SEQ ID NO 35
<211> LENGTH: 1005

-continued

<212> TYPE: DNA
<213> ORGANISM: Homo sapiens

<400> SEQUENCE: 35 atgctgggga tcatggcatg gaatgcaact tgcaaaaact ggctggcagc agaggctgcc 60 ctggaaaagt actacctttc catttttat gggattgagt tcgttgtggg agtccttgga 120 aataccattg ttgtttacgg ctacatcttc tctctgaaga actggaacag cagtaatatt 180 tatctcttta acctctctgt ctctgactta gcttttctgt gcaccctccc catgctgata 240 aggagttatg ccaatggaaa ctggatatat ggagacgtgc tctgcataag caaccgatat 300 gtgcttcatg ccaacctcta taccagcatt ctctttctca cttttatcag catagatcga 360 tacttgataa ttaagtatcc tttccgagaa caccttctgc aaaagaaaga gtttgctatt 420 ttaatctcct tggccatttg ggttttagta accttagagt tactacccat acttcccctt 480 ataaatcctg ttataactga caatggcacc acctgtaatg attttgcaag ttctggagac 540 cccaactaca acctcattta cagcatgtgt ctaacactgt tggggttcct tattcctctt 600 tttgtgatgt gtttctttta ttacaagatt gctctcttcc taaagcagag gaataggcag 660 gttgctactg ctctgcccct tgaaaagcct ctcaacttgg tcatcatggc agtggtaatc 720 ttctctgtgc tttttacacc ctatcacgtc atgcggaatg tgaggatcgc ttcacgcctg 780 gggagttgga agcagtatca gtgcactcag gtcgtcatca actcctttta cattgtgaca 840 cggcctttgg cctttctgaa cagtgtcatc aaccctgtct tctattttct tttgggagat 900 cacttcaggg acatgctgat gaatcaactg agacacaact tcaaatccct tacatccttt 960 agcagatggg ctcatgaact cctactttca ttcagagaaa agtga 1005

<210> SEQ ID NO 36
<211> LENGTH: 334
<212> TYPE: PRT
<213> ORGANISM: Homo sapiens

<400> SEQUENCE: 36

Met Leu Gly Ile Met Ala Trp Asn Ala Thr Cys Lys Asn Trp Leu Ala
1 5 10 15

Ala Glu Ala Ala Leu Glu Lys Tyr Tyr Leu Ser Ile Phe Tyr Gly Ile
20 25 30

Glu Phe Val Val Gly Val Leu Gly Asn Thr Ile Val Val Tyr Gly Tyr
35 40 45

Ile Phe Ser Leu Lys Asn Trp Asn Ser Ser Asn Ile Tyr Leu Phe Asn
50 55 60

Leu Ser Val Ser Asp Leu Ala Phe Leu Cys Thr Leu Pro Met Leu Ile
65 70 75 80

Arg Ser Tyr Ala Asn Gly Asn Trp Ile Tyr Gly Asp Val Leu Cys Ile
85 90 95

Ser Asn Arg Tyr Val Leu His Ala Asn Leu Tyr Thr Ser Ile Leu Phe
100 105 110

Leu Thr Phe Ile Ser Ile Asp Arg Tyr Leu Ile Ile Lys Tyr Pro Phe
115 120 125

Arg Glu His Leu Leu Gln Lys Lys Glu Phe Ala Ile Leu Ile Ser Leu
130 135 140

Ala Ile Trp Val Leu Val Thr Leu Glu Leu Leu Pro Ile Leu Pro Leu
145 150 155 160

Ile Asn Pro Val Ile Thr Asp Asn Gly Thr Thr Cys Asn Asp Phe Ala
165 170 175

-continued

```
Ser Ser Gly Asp Pro Asn Tyr Asn Leu Ile Tyr Ser Met Cys Leu Thr
            180                 185                 190

Leu Leu Gly Phe Leu Ile Pro Leu Phe Val Met Cys Phe Phe Tyr Tyr
        195                 200                 205

Lys Ile Ala Leu Phe Leu Lys Gln Arg Asn Arg Gln Val Ala Thr Ala
    210                 215                 220

Leu Pro Leu Glu Lys Pro Leu Asn Leu Val Ile Met Ala Val Val Ile
225                 230                 235                 240

Phe Ser Val Leu Phe Thr Pro Tyr His Val Met Arg Asn Val Arg Ile
                245                 250                 255

Ala Ser Arg Leu Gly Ser Trp Lys Gln Tyr Gln Cys Thr Gln Val Val
            260                 265                 270

Ile Asn Ser Phe Tyr Ile Val Thr Arg Pro Leu Ala Phe Leu Asn Ser
        275                 280                 285

Val Ile Asn Pro Val Phe Tyr Phe Leu Leu Gly Asp His Phe Arg Asp
    290                 295                 300

Met Leu Met Asn Gln Leu Arg His Asn Phe Lys Ser Leu Thr Ser Phe
305                 310                 315                 320

Ser Arg Trp Ala His Glu Leu Leu Leu Ser Phe Arg Glu Lys
                325                 330


<210> SEQ ID NO 37
<211> LENGTH: 1296
<212> TYPE: DNA
<213> ORGANISM: Homo sapiens

<400> SEQUENCE: 37

atgcaggcgc ttaacattac cccggagcag ttctctcggc tgctgcggga ccacaacctg     60

acgcgggagc agttcatcgc tctgtaccgg ctgcgaccgc tcgtctacac cccagagctg    120

ccgggacgcg ccaagctggc cctcgtgctc accggcgtgc tcatcttcgc cctggcgctc    180

tttggcaatg ctctggtgtt ctacgtggtg acccgcagca aggccatgcg caccgtcacc    240

aacatcttta tctgctcctt ggcgctcagt gacctgctca tcaccttctt ctgcattccc    300

gtcaccatgc tccagaacat ttccgacaac tggctggggg gtgctttcat ttgcaagatg    360

gtgccatttg tccagtctac cgctgttgtg acagaaatgc tcactatgac ctgcattgct    420

gtggaaaggc accagggact tgtgcatcct tttaaaatga agtggcaata caccaaccga    480

agggctttca caatgctagg tgtggtctgg ctggtggcag tcatcgtagg atcacccatg    540

tggcacgtgc aacaacttga gatcaaatat gacttcctat atgaaaagga acacatctgc    600

tgcttagaag agtggaccag ccctgtgcac cagaagatct acaccacctt catccttgtc    660

atcctcttcc tcctgcctct tatggtgatg cttattctgt acagtaaaat tggttatgaa    720

ctttggataa agaaaagagt tggggatggt tcagtgcttc gaactattca tggaaaagaa    780

atgtccaaaa tagccaggaa gaagaaacga gctgtcatta tgatggtgac agtggtggct    840

ctctttgctg tgtgctgggc accattccat gttgtccata tgatgattga atacagtaat    900

tttgaaaagg aatatgatga tgtcacaatc aagatgattt ttgctatcgt gcaaattatt    960

ggattttcca actccatctg taatcccatt gtctatgcat ttatgaatga aaacttcaaa   1020

aaaaatgttt tgtctgcagt ttgttattgc atagtaaata aaaccttctc tccagcacaa   1080

aggcatggaa attcaggaat tacaatgatg cggaagaaag caaagttttc cctcagagag   1140

aatccagtgg aggaaaccaa aggagaagca ttcagtgatg gcaacattga agtcaaattg   1200
```

-continued

```
tgtgaacaga cagaggagaa gaaaaagctc aaacgacatc ttgctctctt taggtctgaa   1260

ctggctgaga attctccttt agacagtggg cattaa                             1296


<210> SEQ ID NO 38
<211> LENGTH: 431
<212> TYPE: PRT
<213> ORGANISM: Homo sapiens

<400> SEQUENCE: 38

Met Gln Ala Leu Asn Ile Thr Pro Glu Gln Phe Ser Arg Leu Leu Arg
  1               5                  10                  15

Asp His Asn Leu Thr Arg Glu Gln Phe Ile Ala Leu Tyr Arg Leu Arg
             20                  25                  30

Pro Leu Val Tyr Thr Pro Glu Leu Pro Gly Arg Ala Lys Leu Ala Leu
         35                  40                  45

Val Leu Thr Gly Val Leu Ile Phe Ala Leu Ala Leu Phe Gly Asn Ala
     50                  55                  60

Leu Val Phe Tyr Val Val Thr Arg Ser Lys Ala Met Arg Thr Val Thr
 65                  70                  75                  80

Asn Ile Phe Ile Cys Ser Leu Ala Leu Ser Asp Leu Leu Ile Thr Phe
                 85                  90                  95

Phe Cys Ile Pro Val Thr Met Leu Gln Asn Ile Ser Asp Asn Trp Leu
            100                 105                 110

Gly Gly Ala Phe Ile Cys Lys Met Val Pro Phe Val Gln Ser Thr Ala
        115                 120                 125

Val Val Thr Glu Met Leu Thr Met Thr Cys Ile Ala Val Glu Arg His
    130                 135                 140

Gln Gly Leu Val His Pro Phe Lys Met Lys Trp Gln Tyr Thr Asn Arg
145                 150                 155                 160

Arg Ala Phe Thr Met Leu Gly Val Val Trp Leu Val Ala Val Ile Val
                165                 170                 175

Gly Ser Pro Met Trp His Val Gln Gln Leu Glu Ile Lys Tyr Asp Phe
            180                 185                 190

Leu Tyr Glu Lys Glu His Ile Cys Cys Leu Glu Glu Trp Thr Ser Pro
        195                 200                 205

Val His Gln Lys Ile Tyr Thr Thr Phe Ile Leu Val Ile Leu Phe Leu
    210                 215                 220

Leu Pro Leu Met Val Met Leu Ile Leu Tyr Ser Lys Ile Gly Tyr Glu
225                 230                 235                 240

Leu Trp Ile Lys Lys Arg Val Gly Asp Gly Ser Val Leu Arg Thr Ile
                245                 250                 255

His Gly Lys Glu Met Ser Lys Ile Ala Arg Lys Lys Lys Arg Ala Val
            260                 265                 270

Ile Met Met Val Thr Val Val Ala Leu Phe Ala Val Cys Trp Ala Pro
        275                 280                 285

Phe His Val Val His Met Met Ile Glu Tyr Ser Asn Phe Glu Lys Glu
    290                 295                 300

Tyr Asp Asp Val Thr Ile Lys Met Ile Phe Ala Ile Val Gln Ile Ile
305                 310                 315                 320

Gly Phe Ser Asn Ser Ile Cys Asn Pro Ile Val Tyr Ala Phe Met Asn
                325                 330                 335

Glu Asn Phe Lys Lys Asn Val Leu Ser Ala Val Cys Tyr Cys Ile Val
            340                 345                 350

Asn Lys Thr Phe Ser Pro Ala Gln Arg His Gly Asn Ser Gly Ile Thr
```

-continued

```
        355                 360                 365

Met Met Arg Lys Lys Ala Lys Phe Ser Leu Arg Glu Asn Pro Val Glu
    370                 375                 380

Glu Thr Lys Gly Glu Ala Phe Ser Asp Gly Asn Ile Glu Val Lys Leu
385                 390                 395                 400

Cys Glu Gln Thr Glu Glu Lys Lys Lys Leu Lys Arg His Leu Ala Leu
                405                 410                 415

Phe Arg Ser Glu Leu Ala Glu Asn Ser Pro Leu Asp Ser Gly His
            420                 425                 430


<210> SEQ ID NO 39
<211> LENGTH: 24
<212> TYPE: DNA
<213> ORGANISM: Homo sapiens

<400> SEQUENCE: 39

ctgtgtacag cagttcgcag agtg                                          24


<210> SEQ ID NO 40
<211> LENGTH: 24
<212> TYPE: DNA
<213> ORGANISM: Homo sapiens

<400> SEQUENCE: 40

gagtgccagg cagagcaggt agac                                          24


<210> SEQ ID NO 41
<211> LENGTH: 31
<212> TYPE: DNA
<213> ORGANISM: Homo sapiens

<400> SEQUENCE: 41

cccgaattcc tgcttgctcc cagcttggcc c                                  31


<210> SEQ ID NO 42
<211> LENGTH: 32
<212> TYPE: DNA
<213> ORGANISM: Homo sapiens

<400> SEQUENCE: 42

tgtggatcct gctgtcaaag gtcccattcc gg                                 32


<210> SEQ ID NO 43
<211> LENGTH: 20
<212> TYPE: DNA
<213> ORGANISM: Homo sapiens

<400> SEQUENCE: 43

tcacaatgct aggtgtggtc                                               20


<210> SEQ ID NO 44
<211> LENGTH: 22
<212> TYPE: DNA
<213> ORGANISM: Homo sapiens

<400> SEQUENCE: 44

tgcatagaca atgggattac ag                                            22


<210> SEQ ID NO 45
<211> LENGTH: 511
<212> TYPE: DNA
<213> ORGANISM: Homo sapiens
```

<400> SEQUENCE: 45 tcacaatgct aggtgtggtc tggctggtgg cagtcatcgt aggatcaccc atgtggcacg 60 tgcaacaact tgagatcaaa tatgacttcc tatatgaaaa ggaacacatc tgctgcttag 120 aagagtggac cagccctgtg caccagaaga tctacaccac cttcatcctt gtcatcctct 180 tcctcctgcc tcttatggtg atgcttattc tgtacgtaaa attggttatg aactttggat 240 aaagaaaaga gttggggatg gttcagtgct tcgaactatt catggaaaag aaatgtccaa 300 aatagccagg aagaagaaac gagctgtcat tatgatggtg acagtggtgg ctctctttgc 360 tgtgtgctgg gcaccattcc atgttgtcca tatgatgatt gaatacagta attttgaaaa 420 ggaatatgat gatgtcacaa tcaagatgat ttttgctatc gtgcaaatta ttggattttc 480 caactccatc tgtaatccca ttgtctatgc a 511

<210> SEQ ID NO 46
<211> LENGTH: 21
<212> TYPE: DNA
<213> ORGANISM: Homo sapiens

<400> SEQUENCE: 46 ctgcttagaa gagtggacca g 21

<210> SEQ ID NO 47
<211> LENGTH: 22
<212> TYPE: DNA
<213> ORGANISM: Homo sapiens

<400> SEQUENCE: 47 ctgtgcacca gaagatctac ac 22

<210> SEQ ID NO 48
<211> LENGTH: 21
<212> TYPE: DNA
<213> ORGANISM: Homo sapiens

<400> SEQUENCE: 48 caaggatgaa ggtggtgtag a 21

<210> SEQ ID NO 49
<211> LENGTH: 23
<212> TYPE: DNA
<213> ORGANISM: Homo sapiens

<400> SEQUENCE: 49 gtgtagatct tctggtgcac agg 23

<210> SEQ ID NO 50
<211> LENGTH: 21
<212> TYPE: DNA
<213> ORGANISM: Homo sapiens

<400> SEQUENCE: 50 gcaatgcagg tcatagtgag c 21

<210> SEQ ID NO 51
<211> LENGTH: 27
<212> TYPE: DNA
<213> ORGANISM: Homo sapiens

<400> SEQUENCE: 51

-continued tggagcatgg tgacgggaat gcagaag 27

<210> SEQ ID NO 52
<211> LENGTH: 27
<212> TYPE: DNA
<213> ORGANISM: Homo sapiens

<400> SEQUENCE: 52 gtgatgagca ggtcactgag cgccaag 27

<210> SEQ ID NO 53
<211> LENGTH: 23
<212> TYPE: DNA
<213> ORGANISM: Homo sapiens

<400> SEQUENCE: 53 gcaatgcagg cgcttaacat tac 23

<210> SEQ ID NO 54
<211> LENGTH: 22
<212> TYPE: DNA
<213> ORGANISM: Homo sapiens

<400> SEQUENCE: 54 ttgggttaca atctgaaggg ca 22

<210> SEQ ID NO 55
<211> LENGTH: 23
<212> TYPE: DNA
<213> ORGANISM: Homo sapiens

<400> SEQUENCE: 55 actccgtgtc cagcaggact ctg 23

<210> SEQ ID NO 56
<211> LENGTH: 24
<212> TYPE: DNA
<213> ORGANISM: Homo sapiens

<400> SEQUENCE: 56 tgcgtgttcc tggaccctca cgtg 24

<210> SEQ ID NO 57
<211> LENGTH: 29
<212> TYPE: DNA
<213> ORGANISM: Homo sapiens

<400> SEQUENCE: 57 caggccttgg attttaatgt cagggatgg 29

<210> SEQ ID NO 58
<211> LENGTH: 27
<212> TYPE: DNA
<213> ORGANISM: Homo sapiens

<400> SEQUENCE: 58 ggagagtcag ctctgaaaga attcagg 27

<210> SEQ ID NO 59
<211> LENGTH: 27
<212> TYPE: DNA
<213> ORGANISM: Homo sapiens

<400> SEQUENCE: 59

-continued tgatgtgatg ccagatacta atagcac 27

<210> SEQ ID NO 60
<211> LENGTH: 27
<212> TYPE: DNA
<213> ORGANISM: Homo sapiens

<400> SEQUENCE: 60 cctgattcat ttaggtgaga ttgagac 27

<210> SEQ ID NO 61
<211> LENGTH: 21
<212> TYPE: DNA
<213> ORGANISM: Homo sapiens

<400> SEQUENCE: 61 gacaggtacc ttgccatcaa g 21

<210> SEQ ID NO 62
<211> LENGTH: 22
<212> TYPE: DNA
<213> ORGANISM: Homo sapiens

<400> SEQUENCE: 62 ctgcacaatg ccagtgataa gg 22

<210> SEQ ID NO 63
<211> LENGTH: 27
<212> TYPE: DNA
<213> ORGANISM: Homo sapiens

<400> SEQUENCE: 63 ctgacttctt gttcctggca gcagcgg 27

<210> SEQ ID NO 64
<211> LENGTH: 27
<212> TYPE: DNA
<213> ORGANISM: Homo sapiens

<400> SEQUENCE: 64 agaccagcca gggcacgctg aagagtg 27

<210> SEQ ID NO 65
<211> LENGTH: 32
<212> TYPE: DNA
<213> ORGANISM: Homo sapiens

<400> SEQUENCE: 65 gatcaagctt ccatcctact gaaaccatgg tc 32

<210> SEQ ID NO 66
<211> LENGTH: 35
<212> TYPE: DNA
<213> ORGANISM: Homo sapiens

<400> SEQUENCE: 66 gatcagatct cagttccaat attcacacca ccgtc 35

<210> SEQ ID NO 67
<211> LENGTH: 22
<212> TYPE: DNA
<213> ORGANISM: Homo sapiens -continued

<400> SEQUENCE: 67 ctggtgtgct ccatggcatc cc 22

<210> SEQ ID NO 68
<211> LENGTH: 22
<212> TYPE: DNA
<213> ORGANISM: Homo sapiens

<400> SEQUENCE: 68 gtaagcctcc cagaacgaga gg 22

<210> SEQ ID NO 69
<211> LENGTH: 24
<212> TYPE: DNA
<213> ORGANISM: Homo sapiens

<400> SEQUENCE: 69 cagcgcaggg tgaagcctga gagc 24

<210> SEQ ID NO 70
<211> LENGTH: 24
<212> TYPE: DNA
<213> ORGANISM: Homo sapiens

<400> SEQUENCE: 70 ggcacctgct gtgacctgtg cagg 24

<210> SEQ ID NO 71
<211> LENGTH: 22
<212> TYPE: DNA
<213> ORGANISM: Homo sapiens

<400> SEQUENCE: 71 gtcctgccac ttcgagacat gg 22

<210> SEQ ID NO 72
<211> LENGTH: 23
<212> TYPE: DNA
<213> ORGANISM: Homo sapiens

<400> SEQUENCE: 72 gaaacttctc tgcccttacc gtc 23

<210> SEQ ID NO 73
<211> LENGTH: 26
<212> TYPE: DNA
<213> ORGANISM: Homo sapiens

<400> SEQUENCE: 73 ccaacaccag catccatggc atcaag 26

<210> SEQ ID NO 74
<211> LENGTH: 27
<212> TYPE: DNA
<213> ORGANISM: Homo sapiens

<400> SEQUENCE: 74 ggagagtcag ctctgaaaga attcagg 27

What is claimed is:

1. A method for identifying a compound for regulating insulin concentration in the blood of a mammal comprising the steps of:

contacting one or more candidate compounds with a host cell that expresses a receptor comprising the amino acid sequence of SEQ ID NO: 8; and measuring the ability of the compound or compounds to inhibit or stimulate said receptor, wherein said inhibition or stimulation of said receptor is indicative of a compound for regulating insulin concentration in the blood of a mammal.

2. The method of claim 1 wherein said compound for regulating insulin concentration in the blood of a mammal is a therapeutic for treating diabetes.

3. The method of claim 1 wherein the compound for regulating insulin concentration in the blood of a mammal is selected from agonist, partial agonist, and inverse agonist of the receptor.

4. The method of claim 1 wherein said host cell comprises an expression vector, said expression vector comprising a polynucleotide, said polynucleotide comprising a nucleotide sequence encoding a polypeptide comprising the amino acid sequence of SEQ ID NO: 8.

5. The method of claim 1 where said host cell is produced by a method comprising:

transfecting a cell with an expression vector, said expression vector comprising a polynucleotide, said polynucleotide comprising a nucleotide sequence encoding a polypeptide comprising the amino acid sequence of SEQ ID NO: 8;

wherein said host cell, under appropriate culture conditions, produces a polypeptide comprising said amino acid sequence of SEQ ID NO: 8.

6. A method for identifying a compound for regulating glucose concentration in the blood of a mammal comprising the steps of:

contacting one or more candidate compounds with a host cell that expresses a receptor comprising the amino acid sequence of SEQ ID NO: 8; and measuring the ability of the compound or compounds to inhibit or stimulate said receptor, wherein said inhibition or stimulation of said receptor is indicative of a compound for regulating glucose concentration in the blood of a mammal.

7. The method of claim 6 wherein said host cell comprises an expression vector, said expression vector comprising a polynucleotide, said polynucleotide comprising a nucleotide sequence encoding a polypeptide comprising the amino acid sequence of SEQ ID NO: 8.

8. The method of claim 6 where said host cell is produced by a method comprising:

transfecting a cell with an expression vector, said expression vector comprising a polynucleotide, said polynucleotide comprising a nucleotide sequence encoding a polypeptide comprising the amino acid sequence of SEQ ID NO: 8;

wherein said host cell, under appropriate culture conditions, produces a polypeptide comprising said amino acid sequence of SEQ ID NO: 8.

9. A method for identifying a compound for regulating glucagon concentration in the blood of a mammal comprising the steps of:

contacting one or more candidate compounds with a host cell that expresses a receptor comprising the amino acid sequence of SEQ ID NO: 8; and measuring the ability of the compound or compounds to inhibit or stimulate said receptor, wherein said inhibition or stimulation of said receptor is indicative of a compound for regulating glucagon concentration in the blood of a mammal.

10. The method of claim 9 wherein said host cell comprises an expression vector, said expression vector comprising a polynucleotide, said polynucleotide comprising a nucleotide sequence encoding a polypeptide comprising the amino acid sequence of SEQ ID NO: 8.

11. The method of claim 9 where said host cell is produced by a method comprising:

transfecting a cell with an expression vector, said expression vector comprising a polynucleotide, said polynucleotide comprising a nucleotide sequence encoding a polypeptide comprising the amino acid sequence of SEQ ID NO: 8;

wherein said host cell, under appropriate culture conditions, produces a polypeptide comprising said amino acid sequence of SEQ ID NO: 8.

*12. A method for identifying a compound for inhibiting or stimulating a receptor comprising:*

*a) the amino acid sequence of SEQ ID NO: 8;*

*b) a mutant of SEQ ID NO: 8, wherein lysine is substituted for leucine at amino acid residue 224;*

*c) an amino acid sequence encoded by a nucleotide sequence that hybridizes to the complete complement of SEQ ID NO:7 at 42° C., followed by washing in 0.1× SSC at 65° C.;*

*d) an amino sequence encoded by the nucleotide sequence of SEQ ID NO: 7;*

*e) a G protein-coupled receptor having at least 95% identity to the amino acid sequence of SEQ ID NO: 8, wherein said G protein-coupled receptor is capable of modulating insulin or glucagon levels; or*

*f) a G protein-coupled receptor encoded by a nucleotide sequence having at least 95% identity to the nucleotide sequence of SEQ ID NO:7, wherein said G protein-coupled receptor is capable of modulating insulin or glucagon levels,*

*comprising the steps of:*

*i) contacting one or more candidate compounds with a host cell or membrane thereof,*

*wherein said host cell or membrane expresses a receptor comprising:*

*a) the amino acid sequence of SEQ ID NO: 8;*

*b) a mutant of SEQ ID NO: 8, wherein lysine is substituted for leucine at amino acid residue 224;*

*c) an amino acid sequence encoded by a nucleotide sequence that hybridizes to the complete complement of SEQ ID NO:7 at 42° C., followed by washing in 0.1× SSC at 65° C.;*

*d) an amino sequence encoded by the nucleotide sequence of SEQ ID NO: 7;*

*e) a G protein-coupled receptor having at least 95% identity to the amino acid sequence of SEQ ID NO: 8, wherein said G protein-coupled receptor is capable of modulating insulin or glucagon levels; or*

*f) a G protein-coupled receptor encoded by a nucleotide sequence having at least 95% identity to the nucleotide sequence of SEQ ID NO:7, wherein said G protein-coupled receptor is capable of modulating insulin or glucagon levels; and*

*ii) measuring the ability of the compound or compounds to inhibit or stimulate said receptor.*

13. The method of claim 12, wherein the compound is selected from agonist, partial agonist, and inverse agonist of the receptor.

14. The method of claim 13, wherein the compound is an agonist of the receptor.

15. The method of claim 13, wherein the compound is a partial agonist of the receptor.

16. The method of claim 13, wherein the compound is an inverse agonist of the receptor.

17. The method of claim 12, wherein said host cell comprises an expression vector, said expression vector comprising a polynucleotide, said polynucleotide comprising:

a) a nucleotide sequence encoding a polypeptide comprising the amino acid sequence of SEQ ID NO: 8;

b) a nucleotide sequence encoding a polypeptide comprising a mutant of SEQ ID NO: 8, wherein lysine is substituted for leucine at amino acid residue 224;

c) a nucleotide sequence that hybridizes to the complete complement of SEQ ID NO:7 at 42° C., followed by washing in 0.1×SSC at 65° C.;

d) the nucleotide sequence of SEQ ID NO: 7;

e) a nucleotide sequence encoding a G protein-coupled receptor having at least 95% identity to the amino acid sequence of SEQ ID NO: 8, wherein said G protein-coupled receptor is capable of modulating insulin or glucagon levels; or f) a nucleotide sequence having at least 95% identity to the nucleotide sequence of SEQ ID NO: 7, wherein said nucleotide sequence encodes a G protein-coupled receptor capable of modulating insulin or glucagon levels.

18. The method of claim 12, wherein said host cell is produced by a method comprising:

transfecting a cell with an expression vector, said expression vector comprising a polynucleotide, said polynucleotide comprising:

a) a nucleotide sequence encoding a polypeptide comprising the amino acid sequence of SEQ ID NO: 8;

b) a nucleotide sequence encoding a polypeptide comprising a mutant of SEQ ID NO: 8, wherein lysine is substituted for leucine at amino acid residue 224;

c) a nucleotide sequence that hybridizes to the complete complement of SEQ ID NO:7 at 42° C., followed by washing in 0.1×SSC at 65° C.;

d) the nucleotide sequence of SEQ ID NO: 7;

e) a nucleotide sequence encoding a G protein-coupled receptor having at least 95% identity to the amino acid sequence of SEQ ID NO: 8, wherein said G protein-coupled receptor is capable of modulating insulin or glucagon levels; or f) a nucleotide sequence having at least 95% identity to the nucleotide sequence of SEQ ID NO: 7, wherein said nucleotide sequence encodes a G protein-coupled receptor capable of modulating insulin or glucagon levels, wherein said host cell, under appropriate culture conditions, produces a polypeptide comprising:

a) the amino acid sequence of SEQ ID NO: 8;

b) a mutant of SEQ ID NO: 8, wherein lysine is substituted for leucine at amino acid residue 224;

c) an amino acid sequence encoded by a nucleotide sequence that hybridizes to the complete complement of SEQ ID NO:7 at 42° C., followed by washing in 0.1×SSC at 65° C.;

d) an amino sequence encoded by the nucleotide sequence of SEQ ID NO: 7;

e) a G protein-coupled receptor having at least 95% identity to the amino acid sequence of SEQ ID NO: 8, wherein said G protein-coupled receptor is capable of modulating insulin or glucagon levels; or f) a G protein-coupled receptor encoded by a nucleotide sequence having at least 95% identity to the nucleotide sequence of SEQ ID NO:7, wherein said G protein-coupled receptor is capable of modulating insulin or glucagon levels.

19. The method of claim 12, wherein the receptor comprises the amino acid sequence of SEQ ID NO: 8.

20. The method of claim 12, wherein the receptor is a mutant of SEQ ID NO: 8, wherein lysine is substituted for leucine at amino acid residue 224.

21. The method of claim 12, wherein the ability of the compound or compounds to inhibit or stimulate said receptor is measured by measuring the activity of a second messenger.

22. The method of claim 21, wherein the second messenger is selected from the group consisting of adenyl cyclase and phospholipase C.

23. The method of claim 12, wherein the ability of the compound or compounds to inhibit or stimulate said receptor is measured by measuring the level of a second messenger.

24. The method of claim 23, wherein the second messenger is selected from the group consisting of cAMP, diacyl glycerol, and inositol 1,4,5-triphosphate.

25. The method of claim 12, wherein the ability of the compound or compounds to inhibit or stimulate said receptor is measured by measuring the binding of GTPγS to a membrane comprising said G protein-coupled receptor.

26. The method of claim 12, wherein the host cell is a mammalian host cell.

27. The method of claim 12, wherein the host cell is a yeast host cell.

28. The method of claim 12, wherein the host cell comprises a reporter system comprising multiple cAMP responsive elements operably linked to a reporter gene.

29. The method of claim 12, wherein said receptor is a constitutively activated receptor.

30. The method according to claim 12, wherein said method comprises identifying a compound for inhibiting or stimulating a receptor comprising:

a) a G protein-coupled receptor having at least 98% identity to the amino acid sequence of SEQ ID NO: 8, wherein said G protein-coupled receptor is capable of modulating insulin or glucagon levels; or b) a G protein-coupled receptor encoded by a nucleotide sequence having at least 98% identity to the nucleotide sequence of SEQ ID NO:7, wherein said G protein-coupled receptor is capable of modulating insulin or glucagon levels, comprising the steps of:

contacting one or more candidate compounds with a host cell or membrane thereof, wherein said host cell or membrane expresses a receptor comprising:

a) a G protein-coupled receptor having at least 98% identity to the amino acid sequence of SEQ ID NO: 8, wherein said G protein-coupled receptor is capable of modulating insulin or glucagon levels; or b) a G protein-coupled receptor encoded by a nucleotide sequence having at least 98% identity to the nucleotide sequence of SEQ ID NO:7, wherein said G protein-coupled receptor is capable of modulating insulin or glucagon levels, and measuring the ability of the compound or compounds to inhibit or stimulate said receptor.

*31. The method of claim 17, wherein said host cell comprises an expression vector, said expression vector comprising a polynucleotide, said polynucleotide comprising:*

*a) a nucleotide sequence encoding a G protein-coupled receptor having at least 98% identity to the amino acid sequence of SEQ ID NO: 8, wherein said G protein-coupled receptor is capable of modulating insulin or glucagon levels; or*

*b) a nucleotide sequence having at least 98% identity to the nucleotide sequence of SEQ ID NO: 7, wherein said nucleotide sequence encodes a G protein-coupled receptor capable of modulating insulin or glucagon levels.*

*32. The method of claim 18, wherein said host cell is produced by a method comprising:*

*transfecting a cell with an expression vector, said expression vector comprising a polynucleotide, said polynucleotide comprising:*

*a) a nucleotide sequence encoding a G protein-coupled receptor having at least 98% identity to the amino acid sequence of SEQ ID NO: 8, wherein said G protein-coupled receptor is capable of modulating insulin or glucagon levels; or*

*b) a nucleotide sequence having at least 98% identity to the nucleotide sequence of SEQ ID NO: 7, wherein said nucleotide sequence encodes a G protein-coupled receptor capable of modulating insulin or glucagon levels,*

*wherein said host cell, under appropriate culture conditions, produces a polypeptide comprising:*

*a) a G protein-coupled receptor having at least 98% identity to the amino acid sequence of SEQ ID NO: 8, wherein said G protein-coupled receptor is capable of modulating insulin or glucagon levels; or*

*b) a G protein-coupled receptor encoded by a nucleotide sequence having at least 98% identity to the nucleotide sequence of SEQ ID NO:7, wherein said G protein-coupled receptor is capable of modulating insulin or glucagon levels.*

* * * * *